United States Patent
Badylak et al.

(10) Patent No.: US 12,161,778 B2
(45) Date of Patent: Dec. 10, 2024

(54) MATRIX BOUND NANOVESICLES AND THEIR USE

(71) Applicant: University of Pittsburgh—Of the Commonwealth System of Higher Education, Pittsburgh, PA (US)

(72) Inventors: Stephen Francis Badylak, West Lafayette, IN (US); Luai Huleihel, Baltimore, MD (US); George S. Hussey, Cranberry Township, PA (US); Juan Diego Naranjo Gutierrez, Manizales (CO)

(73) Assignee: University of Pittsburgh—Of the Commonwealth System of Higher Education

( * ) Notice: Subject to any disclaimer, the term of this patent is extended or adjusted under 35 U.S.C. 154(b) by 388 days.

(21) Appl. No.: 17/072,651

(22) Filed: Oct. 16, 2020

(65) Prior Publication Data

US 2021/0260246 A1 Aug. 26, 2021

Related U.S. Application Data

(63) Continuation of application No. 16/081,847, filed as application No. PCT/US2017/020360 on Mar. 2, 2017, now abandoned.

(60) Provisional application No. 62/302,626, filed on Mar. 2, 2016.

(51) Int. Cl.
| | |
|---|---|
| *A61L 27/36* | (2006.01) |
| *A61K 31/7088* | (2006.01) |
| *A61K 31/7105* | (2006.01) |
| *A61K 35/22* | (2015.01) |
| *A61K 35/36* | (2015.01) |
| *A61K 35/38* | (2015.01) |
| *A61L 27/38* | (2006.01) |
| *A61L 27/54* | (2006.01) |
| *A61P 35/00* | (2006.01) |
| *C12N 15/115* | (2010.01) |

(52) U.S. Cl.
CPC ...... *A61L 27/3633* (2013.01); *A61K 31/7088* (2013.01); *A61K 31/7105* (2013.01); *A61K 35/22* (2013.01); *A61K 35/36* (2013.01); *A61K 35/38* (2013.01); *A61L 27/362* (2013.01); *A61L 27/3629* (2013.01); *A61L 27/3687* (2013.01); *A61L 27/3691* (2013.01); *A61L 27/3834* (2013.01); *A61L 27/54* (2013.01); *A61P 35/00* (2018.01); *C12N 15/115* (2013.01); *A61L 2300/252* (2013.01); *A61L 2300/254* (2013.01); *A61L 2300/414* (2013.01); *C12N 2310/141* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 4,978,668 A | 12/1990 | Babbs et al. |
| 5,007,927 A | 4/1991 | Badylak et al. |
| 5,275,826 A | 1/1994 | Badylak et al. |
| 5,281,422 A | 1/1994 | Badylak et al. |
| 5,352,463 A | 10/1994 | Badylak et al. |
| 5,354,274 A | 10/1994 | Demeter et al. |
| 5,372,821 A | 12/1994 | Badylak et al. |
| 5,445,833 A | 8/1995 | Badylak et al. |
| 5,516,533 A | 5/1996 | Badylak et al. |
| 5,554,389 A | 9/1996 | Badylak et al. |
| 5,573,784 A | 11/1996 | Badylak et al. |
| 5,641,518 A | 6/1997 | Badylak et al. |
| 5,645,860 A | 7/1997 | Knapp, Jr. et al. |
| 5,695,998 A | 12/1997 | Badylak et al. |
| 5,700,486 A | 12/1997 | Canal et al. |
| 5,711,969 A | 1/1998 | Patel et al. |
| 5,753,267 A | 5/1998 | Badylak et al. |
| 5,755,791 A | 5/1998 | Whitson et al. |
| 5,762,966 A | 6/1998 | Knapp, Jr. et al. |
| 5,771,969 A | 6/1998 | Garay |
| 5,866,414 A | 2/1999 | Badylak et al. |
| 5,885,619 A | 3/1999 | Patel et al. |
| 5,955,110 A | 9/1999 | Patel et al. |
| 5,968,096 A | 10/1999 | Whitson et al. |
| 5,997,575 A | 12/1999 | Whitson et al. |
| 6,087,157 A | 6/2000 | Badylak et al. |
| 6,096,347 A | 8/2000 | Geddes et al. |

(Continued)

FOREIGN PATENT DOCUMENTS

| | | |
|---|---|---|
| WO | WO-96/24365 | 8/1996 |
| WO | WO-00/032209 | 6/2000 |

(Continued)

OTHER PUBLICATIONS

Wolf et al., "Immunomodulatory extracellular matrix nanoparticles," *Tissue Engineering* Part A, 21(Supplement 1): S-52 (Sep. 8-1, 2015)(Abstract).

(Continued)

*Primary Examiner* — Teresa E Knight

(74) *Attorney, Agent, or Firm* — Klarquist Sparkman, LLP; Susan Alpert Siegel; Gregory K. Scott

(57) ABSTRACT

A composition is disclosed herein that includes isolated ECM-derived nanovesicles and a pharmaceutically acceptable carrier. Methods are producing the ECM-derived nanovesicles are also disclosed. These ECM-derived nanovesicles can be included in pharmaceutical compositions, bioscaffolds, and devices. Methods for using these ECM-derived nanovesicles are provided.

27 Claims, 39 Drawing Sheets

Specification includes a Sequence Listing.

(56) References Cited

U.S. PATENT DOCUMENTS

| | | |
|---|---|---|
| 6,099,567 A | 8/2000 | Badylak et al. |
| 6,126,686 A | 10/2000 | Badylak et al. |
| 6,187,039 B1 | 2/2001 | Hiles et al. |
| 6,241,981 B1 | 6/2001 | Cobb et al. |
| 6,331,319 B1 | 12/2001 | Badylak et al. |
| 6,375,989 B1 | 4/2002 | Badylak et al. |
| 6,379,710 B1 | 4/2002 | Badylak |
| 6,475,232 B1 | 11/2002 | Babbs et al. |
| 6,485,723 B1 | 11/2002 | Badylak et al. |
| 6,576,265 B1 | 6/2003 | Spievack |
| 6,579,538 B1 | 6/2003 | Spievack |
| 6,653,291 B1 | 11/2003 | Badylak et al. |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,918,396 B1 | 7/2005 | Badylak et al. |
| 7,175,841 B2 | 2/2007 | Badylak et al. |
| 7,482,025 B2 | 1/2009 | Badylak |
| 7,771,717 B2 | 8/2010 | Badylak et al. |
| 7,776,596 B2 | 8/2010 | Badylak |
| 7,795,022 B2 | 9/2010 | Badylak |
| 7,815,686 B2 | 10/2010 | Badylak |
| 7,820,634 B2 | 10/2010 | Badylak et al. |
| 7,919,121 B2 | 4/2011 | Badylak et al. |
| 8,003,131 B2 | 8/2011 | Badylak |
| 8,029,774 B2 | 10/2011 | Beckman et al. |
| 8,084,048 B2 | 12/2011 | Badylak |
| 8,361,503 B2 | 1/2013 | Badylak et al. |
| 8,409,625 B2 | 4/2013 | Badylak |
| 8,535,719 B2 | 9/2013 | Badylak et al. |
| 8,647,677 B2 | 2/2014 | Badylak et al. |
| 8,691,276 B2 | 4/2014 | Badylak et al. |
| 8,716,438 B2 | 5/2014 | Agrawal et al. |
| 8,927,003 B2 | 1/2015 | Badylak et al. |
| 9,277,999 B2 | 3/2016 | Badylak et al. |
| 9,314,340 B2 | 4/2016 | Badylak et al. |
| 9,340,602 B2 | 5/2016 | Agrawal et al. |
| 9,421,307 B2 | 8/2016 | Amoroso et al. |
| 9,480,776 B2 | 11/2016 | Badylak et al. |
| 9,814,744 B2 | 11/2017 | Badylak et al. |
| 9,848,987 B2 | 12/2017 | Badylak et al. |
| 9,861,662 B2 | 1/2018 | Badylak et al. |
| 10,004,827 B2 | 6/2018 | Badylak et al. |
| 10,092,676 B2 | 10/2018 | Amoroso et al. |
| 10,213,526 B2 | 2/2019 | Badylak et al. |
| 10,286,119 B2 | 5/2019 | Badylak et al. |
| 10,729,813 B2 | 8/2020 | Badylak et al. |
| 10,736,991 B2 | 8/2020 | Badylak et al. |
| 11,213,545 B2 | 1/2022 | Badylak et al. |
| 11,291,688 B2 | 4/2022 | Badylak et al. |
| 11,389,566 B2 | 7/2022 | Ramer et al. |
| 11,389,569 B2 | 7/2022 | Badylak et al. |
| 11,406,736 B2 | 8/2022 | Badylak et al. |
| 11,413,375 B2 | 8/2022 | Badylak et al. |
| 11,707,485 B2 | 7/2023 | Badylak et al. |
| 2003/0065379 A1 | 4/2003 | Babbs et al. |
| 2004/0043006 A1 | 3/2004 | Badylak et al. |
| 2004/0078076 A1 | 4/2004 | Badylak et al. |
| 2004/0175366 A1 | 9/2004 | Badylak |
| 2004/0176855 A1 | 9/2004 | Badylak |
| 2004/0187877 A1 | 9/2004 | Badylak et al. |
| 2004/0191226 A1 | 9/2004 | Badylak |
| 2006/0292227 A1 | 12/2006 | McPherson |
| 2007/0135906 A1 | 6/2007 | Badylak et al. |
| 2009/0053279 A1 | 2/2009 | Badylak et al. |
| 2011/0184439 A1 | 7/2011 | Anderson et al. |
| 2014/0031256 A1 | 1/2014 | Lim |
| 2015/0216899 A1 | 8/2015 | Pusic et al. |
| 2016/0045552 A1 | 2/2016 | Ramer et al. |
| 2017/0049932 A1 | 2/2017 | Badylak et al. |
| 2018/0200405 A1 | 7/2018 | Badylak et al. |
| 2018/0243473 A1 | 8/2018 | Badylak et al. |
| 2020/0261624 A1 | 8/2020 | Crapo et al. |
| 2022/0143265 A1 | 5/2022 | Badylak et al. |

FOREIGN PATENT DOCUMENTS

| | | |
|---|---|---|
| WO | WO-2003/059221 | 7/2003 |
| WO | WO-2003/059284 | 7/2003 |
| WO | WO 2012/108842 A1 | 8/2012 |
| WO | WO-2013/009595 | 1/2013 |
| WO | WO 2015/179227 A1 | 11/2015 |
| WO | WO-2018/187286 | 10/2018 |

OTHER PUBLICATIONS

"Fractionation of Cells," From: *Molecular Biology of the Cell 4th edition* (2002), print-out from on-line edition available at: https://www.ncbi.nlm.nih.gov/books/NBK26936/ (3 pages).

Ali et al., "Isolation and characterization of calcifying matrix vesicles from epiphyseal cartilage," *PNAS* 67(3): 1513-1520 (Nov. 1970).

Ali, "Analysis of matrix vesicles and their role in the calcification of epiphyseal cartilage," *Federation Proceedings* 35(2): 135-42 (1976).

Ali, "Matrix vesicles and apatite nodules in arthritic cartilage," Chapter 15 in: *Perspectives in Inflammation: Future Trends in Inflammation*, Willoughby et al., (eds), University Park Press, Baltimore, MD, pp. 211-233 (1977).

Bab et al., "Ultrastructural and biochemical study of extracellular vesicles in normal alveolar bone of rats," *J. Cell Tissue Res.* 202: 1-7 (1979).

De Jong et al., "Extracellular vesicles: potential roles in regenerative medicine," *Frontiers in Immunology* 5(608): pp. 1-13 (Dec. 2014).

Deutsch et al., "Purification and further characterization of isolated matrix vesicles from rat alveolar bone," *Metabolic Bone Disease and Related Research* 3(3): 209-214 (1981)(Abstract only).

Deutsch et al., "Purification and further characterization of isolated matrix vesicles from rat alveolar bone," *Metabolic Bone Disease and Related Research* 3(3): 209-214 (1981).

Gibson et al., "Tissue extracellular matrix nanoparticle presentation in electrospun nanofibers," *BioMed Research International* 2014(Article ID 469120): pp. 1-13 (May 29, 2014).

Gohr et al., "Calcific tendonitis: A model," *Connective Tissue Research* 48(6): 286-291 (2007) (Abstract only).

Gohr et al., "Calcific tendonitis: A model," *Connective Tissue Research* 48(6): 286-291 (2007).

Greening et al., "A protocol for exosome isolation and characterization: Evaluation of ultracentrifugation, density-gradient separation, and immunoaffinity capture methods," *Proteomic Profiling: Methods and Protocols* 1295: 179-210 (2015).

Hirschman et al., "Neutral peptidase activities in matrix vesicles from bovine fetal alveolar bone and dog osteosarcoma," *Calcified Tissue International* 35(6):791-797 (Sep. 1983).

International Search Report from PCT Application No. PCT/US2017/020360, 6 pages (mailed May 8, 2017).

Kapustin et al., "Vascular smooth muscle cell calcification is mediated by regulated exosome secretion," *Circulation Research* 116(8): 1312-1323 (ePub Feb. 23, 2015).

Malda et al., "Extracellular vesicles—new tool for joint repair and regeneration," *Nature Reviews* 12: 244-249 (Apr. 2016).

Martin et al., "Isolation and purification of extracellular matrix vesicles from blood vessels," *Preparative Biochemistry* 22(2): 87-103 (1992) (Abstract only).

Martin et al., "Isolation and purification of extracellular matrix vesicles from blood vessels," *Preparative Biochemistry* 22(2): 87-103 (1992).

Mu et al., "Host matrix modulation by tumor exosomes promotes motility and invasiveness," *Neoplasia* 15(8): 875-887 (Aug. 2013).

(56) References Cited

OTHER PUBLICATIONS

Muhlrad et al., "Occurrence of actin-like protein in extracellular matrix vesicles," *Calcif. Tissue Int.* 34(4): 376-381 (1982).
Narita et al., "Immune responses in patients with esophageal cancer treated with SARTI peptide-pulsed dendritic cell vaccine," International Journal of Oncology vol. 46(4): 1699-1709, (published online Jan. 23, 2015).
Rutnam et al., "miRNAs regulate expression and function of extracellular matrix Molecules," *Matrix Biol.* 32(2): 74-85 (Mar. 11, 2013).
Sabin and Kikyo, "Microvesicles as mediators of tissue regeneration," *Translational Research* 1-10 (2013).
Schurgers et al., "Initiation and propagation of vascular calcification is regulated by a concert of platelet- and smooth muscle cell-derived extracellular vesicles," Frontiers in Cardiovascular Medicine 5(36): 13 pages (Apr. 2018).
Sela et al., "Ultrastructural and biochemical characterization of extracellular matrix vesicles in healing alveolar bone sockets: preliminary indications for the presence of contractile proteins," *Metab. Bone Dis. and Rel. Res.* 1(3): 185-191 (1978).
Shapiro et al., "Matrix Vesicles: Are they anchored exosomes?," *Bone* 79: 29-36 (Oct. 2015).
Thouverey et al., "Proteomic characterization of biogenesis and functions of matrix vesicles released from mineralizing human osteoblast-like cells," *Journal of Proteomics* 74: 1123-1134—(2011).
Tian et al., "A doxorubicin delivery platform using engineered natural membrane vesicle exosomes for targeted tumor therapy," Biomaterials 35(7): 2383-2390 (e-Pub Dec. 15, 2013).
Väänänen et al., "Matrix vesicles in chicken epiphyseal cartilage. Separation from lysosomes and the distribution of inorganic pyrophosphatase activity," *Calcif. Tissue Int.* 28(1): 65-72 (1979).
Wang et al., "Comparison of in vivo adipogenic capabilities of two different extracellular matrix microparticle scaffolds," *Plastic and Reconstructive Surgery* 131(2):174e-187e (Feb. 2013).
Written Opinion from PCT Application No. PCT/US2017/020360, 5 pages (mailed May 8, 2017).
Wuthier et al., "Non-enzymatic isolation of matrix vesicles: characterization and initial studies on 45Ca and 32P-orthophosphate metabolism," *Metab. Bone Dis. and Rel. Res.*, 1(2): 125-136 (1978).
Zhou et al., "Label-free quantification proteomics reveals novel calcium binding proteins in matrix vesicles isolated from mineralizing Saos-2 cells," *BioScience Trends* 7(3): 144-151 (2013).
Alicuben, E T, and S R DeMeester. "Onlay ventral hernia repairs using porcine non-cross-linked dermal biologic mesh." *Hernia : The Journal of Hernias and Abdominal Wall Surgery* vol. 18,5 (2014): 705-12.
Anderson, H C. "Molecular biology of matrix vesicles." *Clinical Orthopaedics and Related Research* 314(1995): 266-80.
Anderson, H C. "Vesicles associated with calcification in the matrix of epiphyseal cartilage." *The Journal of cell biology* vol. 41,1 (1969): 59-72.
Anderson, H C. "Matrix vesicles and calcification." *Current Rheumatology Reports* vol. 5,3 (2003): 222-6.
Badylak, Stephen F et al. "Esophageal preservation in five male patients after endoscopic inner-layer circumferential resection in the setting of superficial cancer: a regenerative medicine approach with a biologic scaffold." *Tissue Engineering*. Part A vol. 17,11-12 (2011): 1643-50,.
Badylak, Stephen F et al. "Extracellular matrix as a biological scaffold material: Structure and function." *Acta Biomaterialia* vol. 5,1 (2009): 1-13.
Badylak, Stephen F. "Decellularized allogeneic and xenogeneic tissue as a bioscaffold for regenerative medicine: factors that influence the host response." *Annals of Biomedical Engineering* vol. 42,7 (2014): 1517-27.
Banerjee, Sami et al. "miR-125a-5p regulates differential activation of macrophages and inflammation." *The Journal of Biological Chemistry* vol. 288,49 (2013): 35428- 36.

Bejjani, Ghassan K et al. "Safety and efficacy of the porcine small intestinal submucosa dural substitute: results of a prospective multicenter study and literature review." *Journal of Neurosurgery* vol. 106,6 (2007): 1028-33.
Ben-Dov, Iddo Z et al. "Cell and Microvesicle Urine microRNA Deep Sequencing Profiles from Healthy Individuals: Observations with Potential Impact on Biomarker Studies." *PloS One* vol. 11,1 e0147249 (2016).
Bobrie, Angélique et al. "Exosome secretion: molecular mechanisms and roles in immune responses." *Traffic (Copenhagen, Denmark)* vol. 12,12 (2011): 1659-68.
Brown, Bryan N et al. "Macrophage phenotype as a predictor of constructive remodeling following the implantation of biologically derived surgical mesh materials." *Acta Biomaterialia* vol. 8,3 (2012): 978-87.
Chaudhuri, Aadel A et al. "MicroRNA-125b potentiates macrophage activation." *Journal of Immunology (Baltimore, Md.: 1950)* vol. 187,10 (2011): 5062-8.
Cortiella, Joaquin et al. "Influence of acellular natural lung matrix on murine embryonic stem cell differentiation and tissue formation." *Tissue Engineering*. Part A vol. 16,8 (2010): 2565-80.
Crapo, Peter M et al. "An overview of tissue and whole organ decellularization processes." *Biomaterials* vol. 32,12 (2011): 3233-43.
Daigneault, Marc et al. "The identification of markers of macrophage differentiation in PMA-stimulated THP-1 cells and monocyte-derived macrophages." *PloS One* vol. 5,1 e8668 (2010).
Deatherage, Brooke L, and Brad T Cookson. "Membrane vesicle release in bacteria, eukaryotes, and archaea: a conserved yet underappreciated aspect of microbial life." *Infection and immunity* vol. 80,6 (2012): 1948-57.
Escola, J M et al. "Selective enrichment of tetraspan proteins on the internal vesicles of multivesicular endosomes and on exosomes secreted by human B-lymphocytes." *The Journal of Biological Chemistry* vol. 273,32 (1998): 20121-7.
Gilbert, Thomas W et al. "Production and characterization of ECM powder: implications for tissue engineering applications." *Biomaterials* vol. 26,12 (2005): 1431-5.
Hargett, Leslie A, and Natalie N Bauer. "On the origin of microparticles: From "platelet dust" to mediators of intercellular communication." *Pulmonary Circulation* vol. 3,2 (2013): 329-40.
Huang, Xiaoyi et al. "Characterization of human plasma-derived exosomal RNAs by deep sequencing." *BMC Genomics* vol. 14, 319 (2013).
Huleihel, Luai et al. "Matrix-bound nanovesicles within ECM bioscaffolds." *Science Advances* vol. 2,6 e1600502 (2016).
Ji, Hong et al. "Deep sequencing of RNA from three different extracellular vesicle (EV) subtypes released from the human LIM1863 colon cancer cell line uncovers distinct miRNA-enrichment signatures." *PloS One* vol. 9,10 e110314 (2014).
Kalajzic, Zana et al. "Use of an alpha-smooth muscle actin GFP reporter to identify an osteoprogenitor population." *Bone* vol. 43,3 (2008): 501-10.
Keane, Timothy J et al. "Preparation and characterization of a biologic scaffold from esophageal mucosa." *Biomaterials* vol. 34,28 (2013): 6729-37.
Koga, Yoshikatsu et al. "Exosome can prevent RNase from degrading microRNA in feces." *Journal of Gastrointestinal Oncology* vol. 2,4 (2011): 215-22.
Kuchen, Stefan et al. "Regulation of microRNA expression and abundance during lymphopoiesis." *Immunity* vol. 32,6 (2010): 828-39.
Lamichhane, Tek N et al. "Emerging roles for extracellular vesicles in tissue engineering and regenerative medicine." *Tissue Engineering*. Part B, Reviews vol. 21,1 (2015): 45-54.
Lasner et al., "Structure-functional effects of a series of alcohols on acetylcholinesterase-associated membrane vesicles: elucidation of factors contributing to the alcohol action." *Arch. Biochem. Biophys.*, vol. 317, 2 (1995): 391-396.
Londono, Ricardo, and Stephen F Badylak. "Biologic scaffolds for regenerative medicine: mechanisms of in vivo remodeling." *Annals of Biomedical engineering* vol. 43,3 (2015): 577-92.

(56) References Cited

OTHER PUBLICATIONS

Longo, Umile Giuseppe et al. "Scaffolds in tendon tissue engineering." *Stem Cells International* vol. 2012 (2012): 517165.
Mase, Vincent J Jr et al. "Clinical application of an acellular biologic scaffold for surgical repair of a large, traumatic quadriceps femoris muscle defect." *Orthopedics* vol. 33,7 511 (2010).
Nawaz, Muhammad et al. "The emerging role of extracellular vesicles as biomarkers for urogenital cancers." *Nature Reviews. Urology* vol. 11,12 (2014): 688-701.
Salzberg, C Andrew. "Nonexpansive immediate breast reconstruction using human acellular tissue matrix graft (AlloDerm)," *Annals of plastic surgery* vol. 57,1 (2006): 1-5.
Sellaro, Tiffany L et al. "Maintenance of hepatic sinusoidal endothelial cell phenotype in vitro using organ-specific extracellular matrix scaffolds." *Tissue Engineering* vol. 13,9 (2007): 2301-10.
Sicari, Brian M et al. "A murine model of volumetric muscle loss and a regenerative medicine approach for tissue replacement." *Tissue Engineering.* Part A vol. 18,19-20 (2012): 1941-8.
Sicari, Brian M et al. "The promotion of a constructive macrophage phenotype by solubilized extracellular matrix." *Biomaterials* vol. 35,30 (2014): 8605-12.
Stevanato, Lara et al. "Investigation of Content, Stoichiometry and Transfer of miRNA from Human Neural Stem Cell Line Derived Exosomes." *PloS One* vol. 11,1 e0146353 (2016).
Théry, C et al. "Molecular characterization of dendritic cell-derived exosomes, Selective accumulation of the heat shock protein hsc73." *The Journal of Cell Biology* vol. 147,3 (1999): 599-610.
Théry, C et al. "Proteomic analysis of dendritic cell-derived exosomes: a secreted subcellular compartment distinct from apoptotic vesicles." *Journal of Immunology (Baltimore, Md. : 1950)* vol. 166,12 (2001): 7309-18.
Thornton, F J, and A Barbul. "Healing in the gastrointestinal tract." *The Surgical Clinics of North America* vol. 77,3 (1997): 549-73.
Valentin, Jolene E et al. "Extracellular matrix bioscaffolds for orthopaedic applications. A comparative histologic study." *The Journal of Bone and Joint Surgery. American volume* vol. 88,12 (2006): 2673-86.
van der Pol, Edwin et al. "Classification, functions, and clinical relevance of extracellular vesicles." *Pharmacological Reviews* vol. 64,3 (2012): 676-705.
Wolf, Matthew T et al. "A hydrogel derived from decellularized dermal extracellular matrix." *Biomaterials* vol. 33,29 (2012): 7028-38.
Wolf, P. "The nature and significance of platelet products in human plasma." *British Journal of Haematology* vol. 13,3 (1967): 269-88.
Yáñez-Mó, María et al. "Biological properties of extracellular vesicles and their physiological functions." *Journal of Extracellular Vesicles* vol. 4, 27066 (2015).
Yokota, Takafumi et al. "Bone marrow lacks a transplantable progenitor for smooth muscle type alpha-actin-expressing cells." *Stem Cells* (Dayton, Ohio) vol. 24,1 (2006): 13-22.
Zhang, Yingying et al. "Expression profiles of miRNAs in polarized macrophages." *International Journal of Molecular Medicine* vol. 31,4 (2013): 797-802.

FIG. 4A

| Product / Description | BARD XENMATRIX™ | Dermis | ACELL® MATRISTEM® | UBM | COOK® Biotech | SIS |
|---|---|---|---|---|---|---|
| miRNA count | 46 | 33 | 223 | 240 | 62 | 53 |
| % of mutual miRNAs | 56.52174% | | 77.5% | | 58.06452% | |

FIG. 4B

| Product / Molecular and Cellular Functions | BARD XENMATRIX™ | Dermis | ACELL® MATRISTEM® | UBM | COOK® Biotech | SIS |
|---|---|---|---|---|---|---|
| Cellular Development | 26 | 18 | 50 | 74 | 30 | 30 |
| Cellular Growth and Proliferation | 27 | 19 | 48 | 73 | 30 | 29 |
| Cell Death and Survival | 21 | 14 | 36 | 64 | 22 | 23 |
| Cellular Movement | 17 | 12 | 32 | 58 | 22 | 20 |
| Cell Cycle | 10 | 7 | 19 | 37 | 11 | 10 |

FIG. 4C

| Product / Physiological System Development and Function | BARD XENMATRIX™ | Dermis | ACELL® MATRISTEM® | UBM | COOK® Biotech | SIS |
|---|---|---|---|---|---|---|
| Connective Tissue Development and Function | 7 | 6 | 12 | 0 | 7 | 4 |
| Organismal Development | 12 | 0 | 17 | 33 | 0 | 14 |
| Organ Development | 0 | 9 | 13 | 32 | 11 | 11 |

UBM MVs (no cells)     Control     UBM MVs

Neurite extension N1E-115 cells

PVSC scratch assay

PVSC cell count (96 hrs)

FIG. 6

| Reference | Source of miRNA | mir-145-5p (RPM) | let-7b-5p present |
|---|---|---|---|
| Huang et al., 2013 | Exosomes from Plasma | 19 | Yes |
| Ben-dov et al., 2016 | Exosome from Urine | 28 | Yes |
| Ji et al., 2014 | Exosomes from cell media | 0 | Yes |
| | Cells | 0 | Yes |
| Stevanato et al., 2016 | Exosomes from cell media | 0 | Yes |
| | Cells | 0 | Yes |
| Kuchen et al., 2010 | Cells | 3 | Yes |
| | Macrophages | 474 | Yes |
| | Embrionic Stem Cells | 73 | Yes |
| | Fibroblasts | 1218 | Yes |
| | Tissue (Average) | 163 | Yes |
| | Heart | 13.2 | Yes |
| | Brain | 25.7 | Yes |
| | Lung | 184.1 | Yes |
| | Liver | 7.7 | Yes |
| | Kidney | 75.2 | Yes |
| | Pancreas | 133.8 | Yes |
| | Skin | 150.9 | Yes |
| | Muscle | 14.9 | Yes |
| | S. Glands | 47.7 | Yes |
| | Testes | 300.9 | Yes |
| | Ovaries | 834.7 | Yes |
| Lab data | Exosomes from commercial UBM | 21390 | Yes |
| | Exosomes from commercial Dermis | 173 | Yes |
| | Exosomes from commercial SIS | 765 | Yes |
| | Exosomes from lab-made Dermis | 52 | Yes |
| | Exosomes from lab made SIS | 366 | Yes |
| | Exosomes from lab-made UBM | 32966 | Yes |

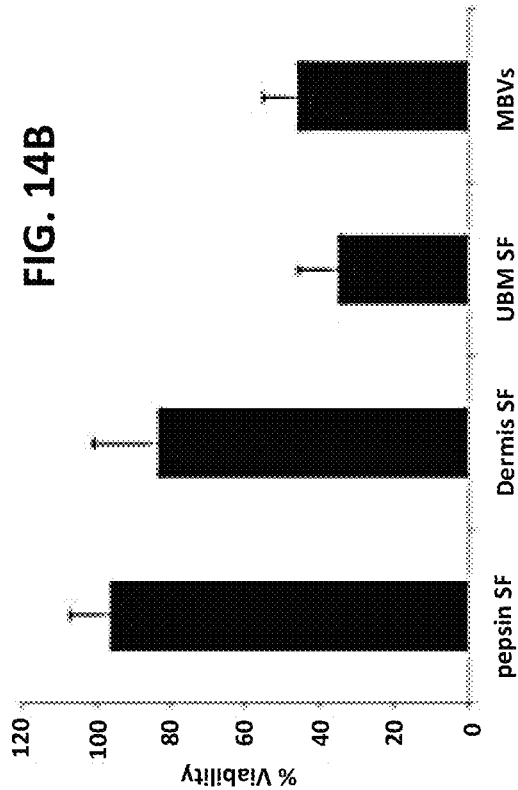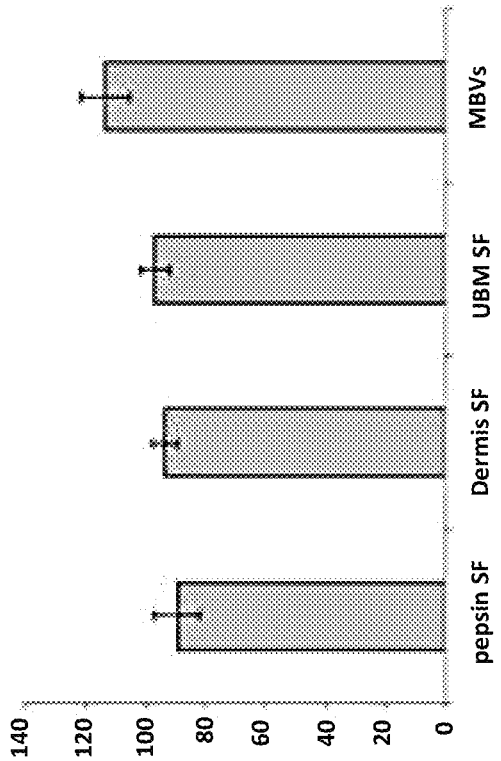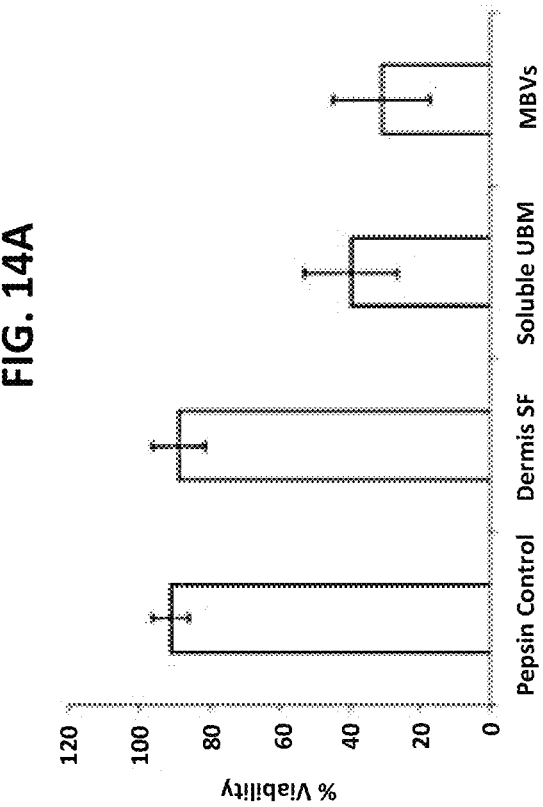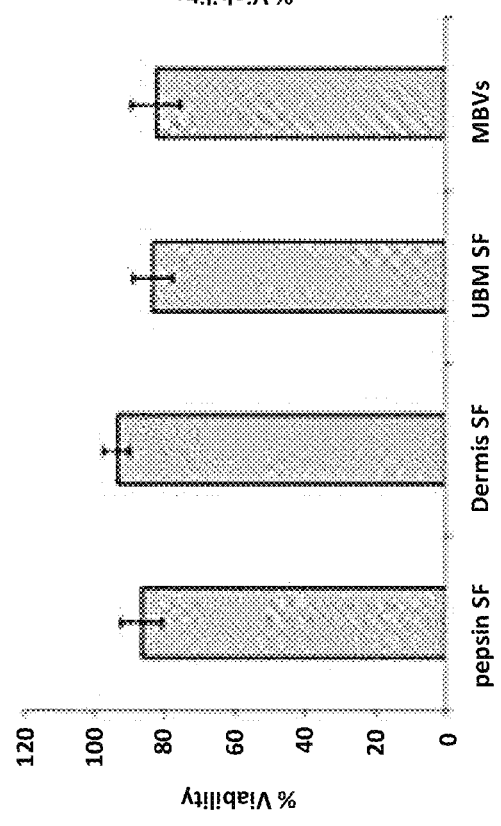

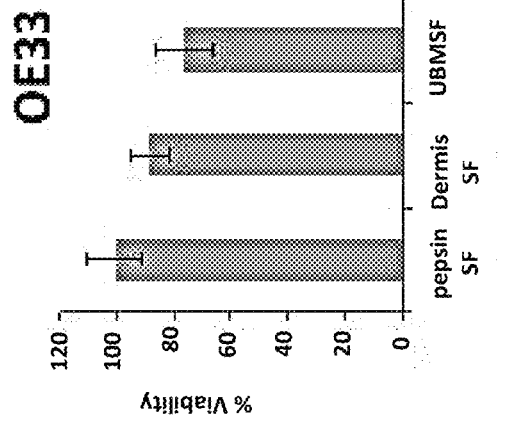
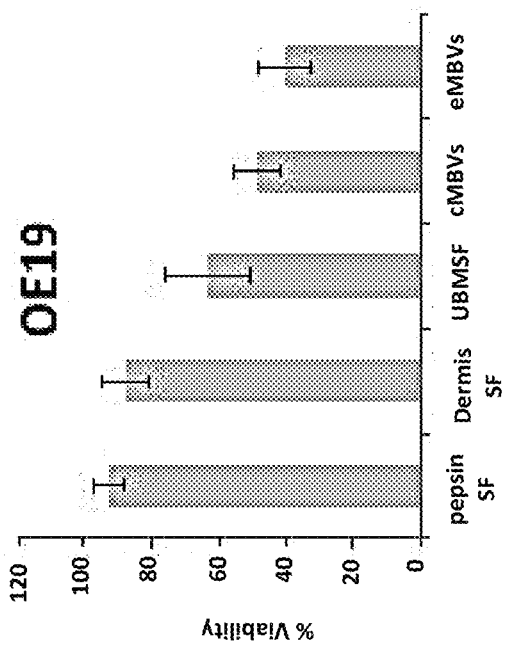
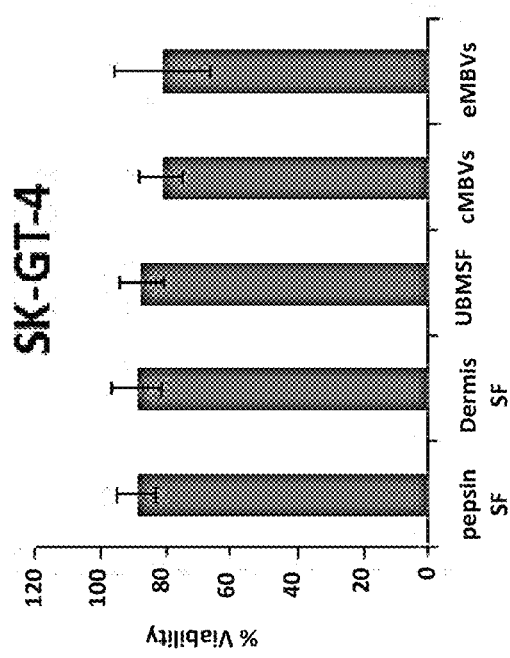
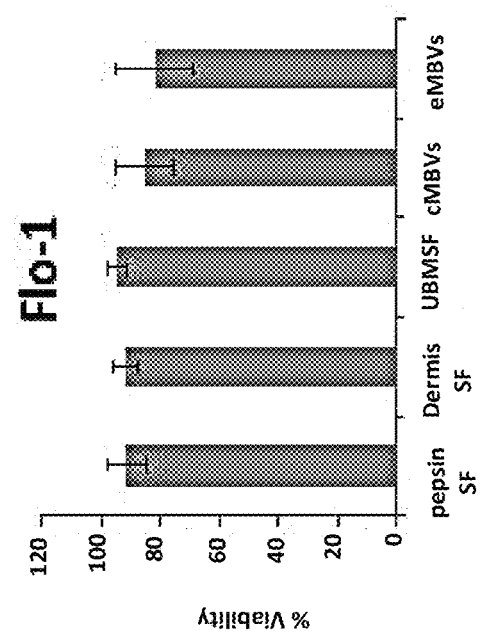
SF = soluble fraction
cMBVs = collagenase MBVs
eMBVs = elastase MBVs
FIG. 15

FIG. 17

FIG. 18A
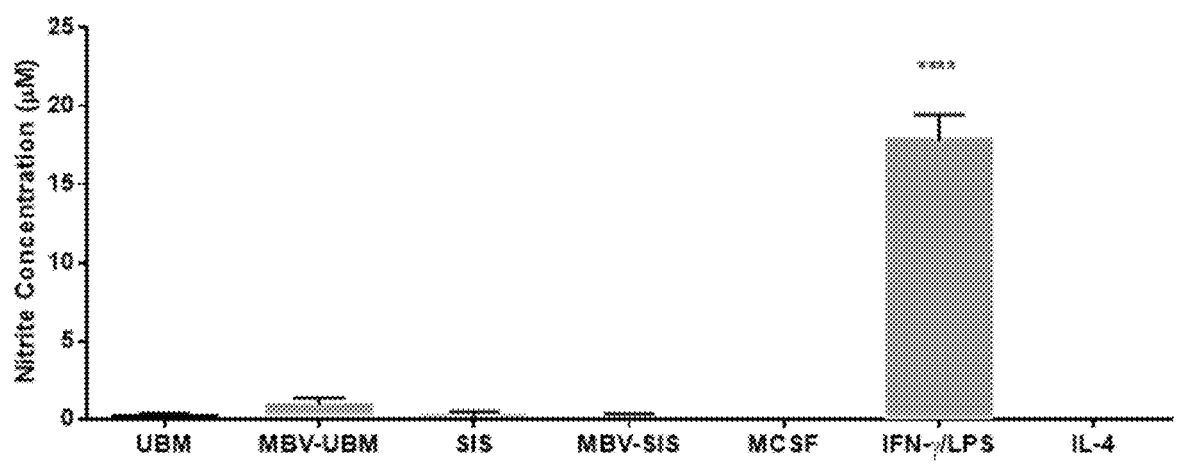
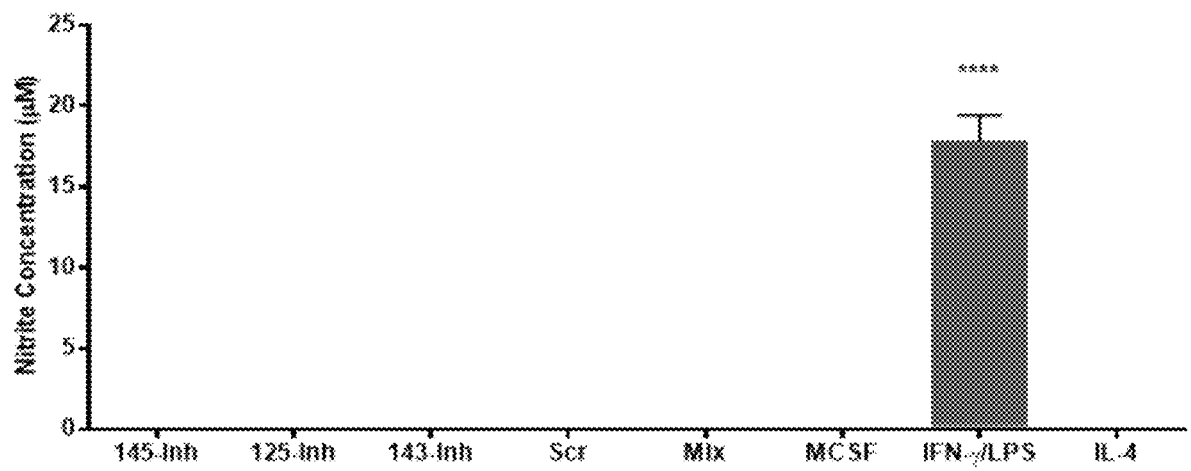

FIG. 18B
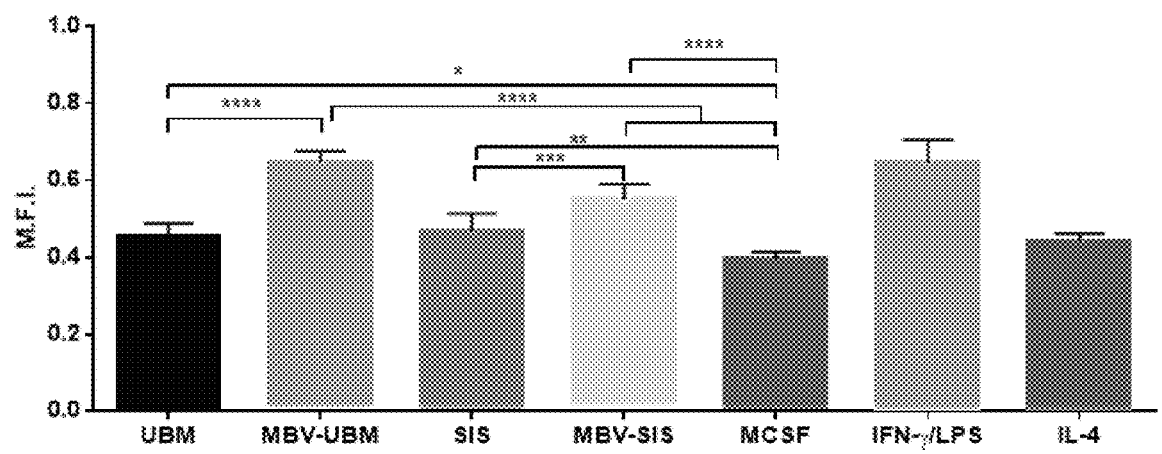
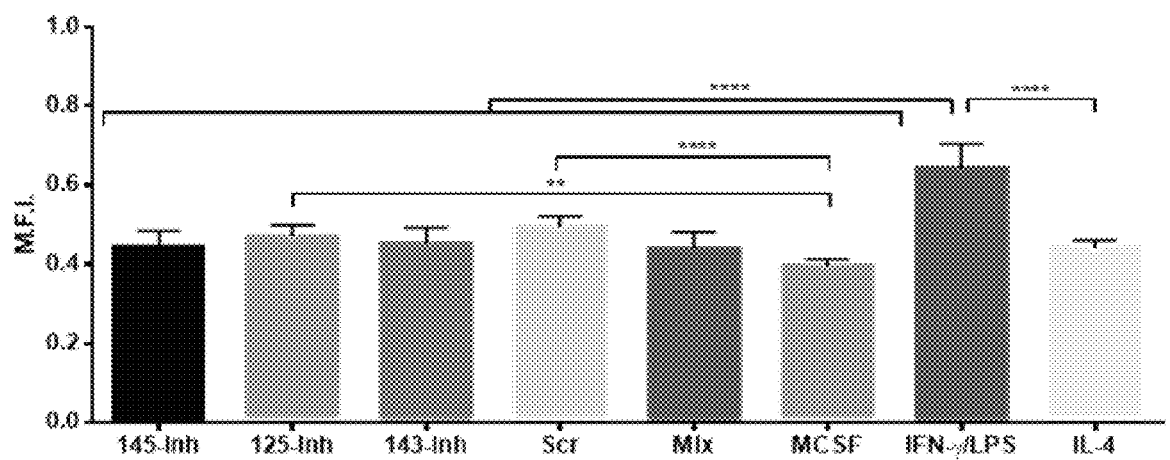

FIG. 18C
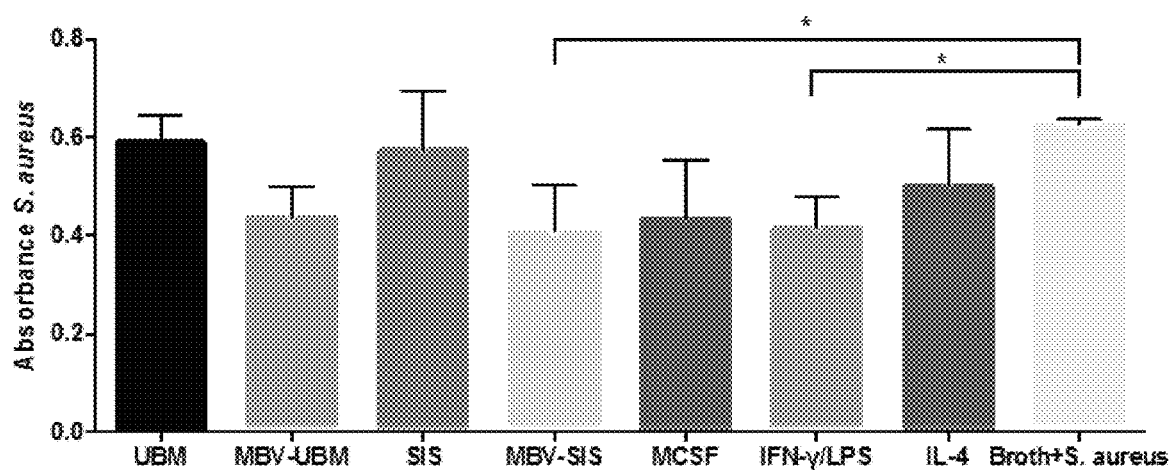
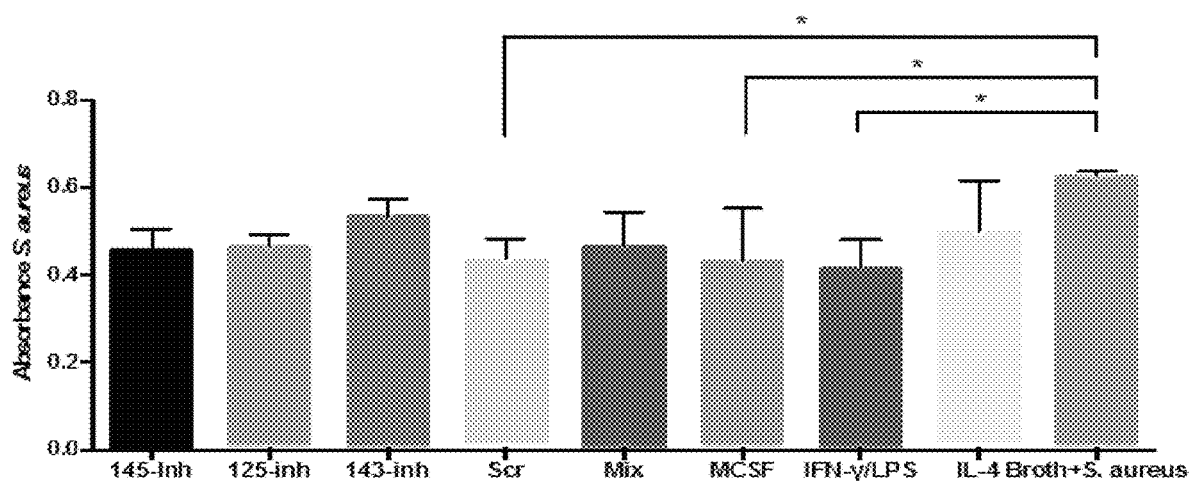

MATRIX BOUND NANOVESICLES AND THEIR USE

CROSS REFERENCE TO RELATED APPLICATIONS

This is a continuation of U.S. patent application Ser. No. 16/081,847, filed on Aug. 31, 2018, which is a § 371 U.S. national stage of International Application No. PCT/US2017/020360, filed Mar. 2, 2017, and which claims the benefit of U.S. Provisional Application No. 62/302,626, filed Mar. 2, 2016. The prior applications are all incorporated by reference herein.

FIELD

This relates to the field of biological scaffolds, specifically to nanovesicles derived from the extracellular matrix (ECM) and their use.

BACKGROUND

Biologic scaffolds composed of extracellular matrix (ECM) have been developed as surgical mesh materials and allowed for use in a large number of clinical applications including ventral hernia repair (Alicuban et al., Hernia. 2014; 18(5):705-712), musculoskeletal reconstruction (Mase et al., Orthopedics. 2010; 33(7):511), esophageal reconstruction (Badylak et al., Tissue Eng Part A. 2011; 17(11-12):1643-50), dura mater replacement (Bejjani et al., J Neurosurg. 2007; 106(6):1028-1033), tendon repair (Longo et al., Stem Cells Int. 2012; 2012:517165), breast reconstruction (Salzber, Ann Plast Surg. 2006; 57(1): 1-5), amongst others (Badylak et al., Acta Biomater. 2009; 5(1): 1-13). The use of these biomaterials is typically associated with at least partial restoration of functional, site-appropriate tissue; a process referred to as "constructive remodeling." These ECM-based materials are most commonly xenogeneic in origin (e.g., porcine for use in human hosts), and are prepared by the decellularization of source tissue such as dermis, urinary bladder (UBM) and small intestinal submucosa (SIS), amongst others. These xenogeneic scaffolds do not elicit an adverse innate or adaptive immune response (Badylak et al., Ann Biomed Eng. 2014; 42(7): 1517-1527).

The factors which determine outcome in clinical applications are numerous and include surgical technique, appropriateness of the selected bioscaffold for the clinical condition, age of the allogeneic or xenogeneic tissue source donor, and patient co-morbidities, among others (Badylak et al., Ann Biomed Eng. 2014; 42(7): 1517-1527). Perhaps the major determinant of outcome is the method by which these bioscaffolds are processed including decellularization techniques, terminal sterilization, and state of hydration (Badylak et al., Ann Biomed Eng. 2014; 42(7): 1517-1527). Inadequate decellularization, the use of chemical crosslinking agents, and the lack of appropriate mechanical loading following in vivo placement have been shown to contribute to poor results (Badylak et al., Ann Biomed Eng. 2014; 42(7): 1517-1527; Crapo et al., Biomaterials. 2011; 32(12): 3233-43).

The outcome of using a particular bioscaffold is dictated by the host tissue response to the final product (i.e. post processing) following implantation. Among the varied components of the host response that have been associated with the ECM induced, site-appropriate constructive and functional tissue remodeling are angiogenesis, innervation, stem cell recruitment, antimicrobial activity, and modulation of the innate immune response (Londono and Badylak, Ann Biomed Eng. 2015; 43(3):577-592) In addition, there are clear differences between homologous and heterologous applications. For example, ECM bioscaffolds composed of liver ECM support the hepatic sinusoidal endothelial cell phenotype whereas ECMs harvested from heterologous tissue and organs do not (Sellaro et al., Tissue Eng. 2007; 13(9):2301-2310). Similarly, lung ECM promotes site appropriate stem cell differentiation (Coriella et al., Tissue Eng Part A. 2010; 16(8):2565-2580). There is clear "cross-talk" between cells and ECM, however, the mechanisms by which ECM signals and directs cell behavior and vice versa are largely unknown. A need remains to identify the components and mechanisms for these effects, and to harness these effects so that ECM can be biologically manipulated for specific applications. Once these components and mechanisms are identified, they can be manipulated for use in medical devices and implemented in such a manner to affect cell proliferation, survival and differentiation

SUMMARY

It is disclosed herein that nanovesicles are embedded within the fibrillar network of the ECM. These matrix bound nanoparticles shield their cargo from degradation and denaturation during the ECM-scaffold manufacturing process. Microvesicles previously have been identified almost exclusively in body fluids and cell culture supernatant. Thus, the presence of matrix bound nanovesicles was surprising. These nanovesicles differ from other microvesicles, as they are resistant to detergent and/or enzymatic digestion, contain a cluster of different microRNAs, and are enriched in miR-145. The disclosed nanvesicles do not have characteristic surface proteins found in other microvesicles. The nanovesicles provide unique biological properties that can be utilized in bioscaffolds and devices.

A composition is disclosed herein that includes isolated nanovesicles derived from an ECM and a pharmaceutically acceptable carrier. In some embodiments, the nanovesicles do not express CD63 and/or CD81, or are $CD63^{lo}CD81^{lo}$.

In additional embodiments, methods are disclosed for isolating nanovesicles bound to an extracellular matrix. These methods include, but are not limited to, digesting the extracellular matrix with an enzyme to produce digested extracellular matrix, centrifuging the digested extracellular matrix to remove collagen fibril remnants and thus to produce a fibril-free supernatant, centrifuging the fibril-free supernatant to isolate the solid materials; suspending the solid materials in a buffer, and the use of various salts in order to isolate nanovesicles from the extracellular matrix.

In further embodiments, methods are disclosed for inducing cell proliferation, migration and/or differentiation on an extracellular matrix of interest. These methods utilize the disclosed nanovesicles. The methods can include introducing isolated nanovesicles derived from a second extracellular matrix into an extracellular matrix of interest.

In yet other embodiments, bioscaffolds are disclosed that include isolated nanovesicles derived from an extracellular matrix. In further embodiments, disclosed are medical devices including and/or coated with isolated nanovesicles derived from an extracellular matrix.

The foregoing and other objects, features, and advantages of the invention will become more apparent from the following detailed description, which proceeds with reference to the accompanying figures.

BRIEF DESCRIPTION OF THE DRAWINGS

FIGS. 4A-4C. Small RNA sequencing data reveals miRNA presence within nanovesicles as well as mutual miRNAs between commercial products and parallel lab made products (A). Ingenuity pathway analysis (IPA) reveals different cell function pathways (i.e cell cycle, cell death and cell growth) are included within the identified miRNAs are associated with (B).

FIG. 6. Table showing reads of mir-145p in deep sequencing on different sources. Mir-145-5p is not highly expressed in exosomes from plasma, urine, Cell media, or cells, except in those associated with Extracellular matrix (Fibroblasts). It is expressed in all tissues in different proportions as well as in the exosomes isolated from Extracellular matrix Scaffolds. Let-7b-5p presence was used as a control. References are Huang et al. BMC Genomics. 2013; 14:319. doi: 10.1186/1471-2164-14-319; Ben-Dov et al., PLOS ONE. 2016; 11(1):e0147249. doi: 10.1371/journal.pone.0147249; Ji et al., PLOS ONE. 2014; 9(10):e110314. doi: 10.1371/journal.pone.0110314; Stevanato et al., PLOS ONE. 2016; 11(1):e0146353. doi: 10.1371/journal.pone.0146353; Kuchen et al., Immunity. 2010; 32(6):828-839. doi:10.1016/j.immuni.2010.05.009.

FIGS. 14A-14D. MBVs derived from ECM bioscaffolds inhibit glioma cell viability. Effect of ECM soluble fraction or MBVs on cell viability was determined by MTT assay after 24 hrs of treatment. High grade primary human glioma cells (A), low grade primary human glioma cells (B), human microglia cells (C), and neural progenitor cells (D).

FIG. 15. Soluble fraction of ECM bioscaffolds and MBVs derived from ECM bioscaffolds inhibit esophageal cancer cell viability. The MTT assay assessed cancer cell viability.

FIG. 17. Bone marrow derived macrophages were harvested from C57bl/6 mice and allowed to mature to macrophages. The cells were then treated with one of the following conditions: (1) 20 ng/ml IFNγ and 100 ng/ml LPS to promote an $M_{IFNg+LPS}$ phenotype (M1-like), (2) 20 ng/ml IL-4 to promote an $M_{IL-4}$ phenotype (M2-like), (3) 250 ug/ml of UBM-ECM, or SIS-ECM to promote an MECM phenotype, or (4) 25 ug/ml of UBM-MBVs, or SIS-MBVs to promote an $M_{MBV}$ phenotype. Pepsin (1 mg/ml) and Collagenase (0.1 mg/ml) were used as baseline controls for ECM and MBVs, respectively. Cells were then washed with PBS and fixed with 2% paraformaldehyde for 45 minutes. Using murine-specific primary antibodies and fluorophore conjugated secondary antibodies, target protein expression could be evaluated qualitatively. F4/80 was used as a pan-macrophage marker, TNFα and iNOS were used as M1-like markers, and Fizz1 and Arginase1 were used as M2-like markers. Exposure times were established using isotype and appropriate cytokine controls and maintained constant throughout.

FIG. 18A-18C. MBV treatment exceeds ECM effects on BMDM functional assays. Macrophages were exposed for 24 h to MCSF control, 250 mg/ml ECM, 25 mg/ml MBVs, or the cytokine controls IFNg+LPS or IL-4. (A) Macrophage supernatants were mixed with 1% sulfanilamide in 5% phosphoric acid for 10 minutes, followed by addition of 0.1% N-1-napthylethylenediamine (NED) dihydrochloride in water. The solutions were read in a spectrophotometer at 540 nm and compared to the standard curve of sodium nitrite to assess nitric oxide production levels. (B) Treated macrophages were incubated with Vybrant Phagocytosis Kit FITC-labeled E. coli beads for 2 hours. Cells were fixed and stained with DAPI. Using fluorescence microscopy, the cells were visualized and quantified for mean fluorescence intensity of the cells using Cell Profiler software. (C) Macrophages were treated for 18 hours with 250 mg/ml ECM, 25 mg/ml MBVs, or the cytokine controls IFNγ+LPS or IL4. All treated macrophages were washed with PBS and incubated with serum-free, antibiotic-free medium for 5 hours. Medium containing the secreted products of macrophages was collected and used at a 1:10 ratio with tryptic soy broth and $1\times10^4$ CFU/ml of S. aureus. Bacterial growth was evaluated by measuring absorbance at 570 nm. (Values: Mean absorbance±Standard deviation, N=4, *p<0.05).

SEQUENCE LISTING

Figure 1A:
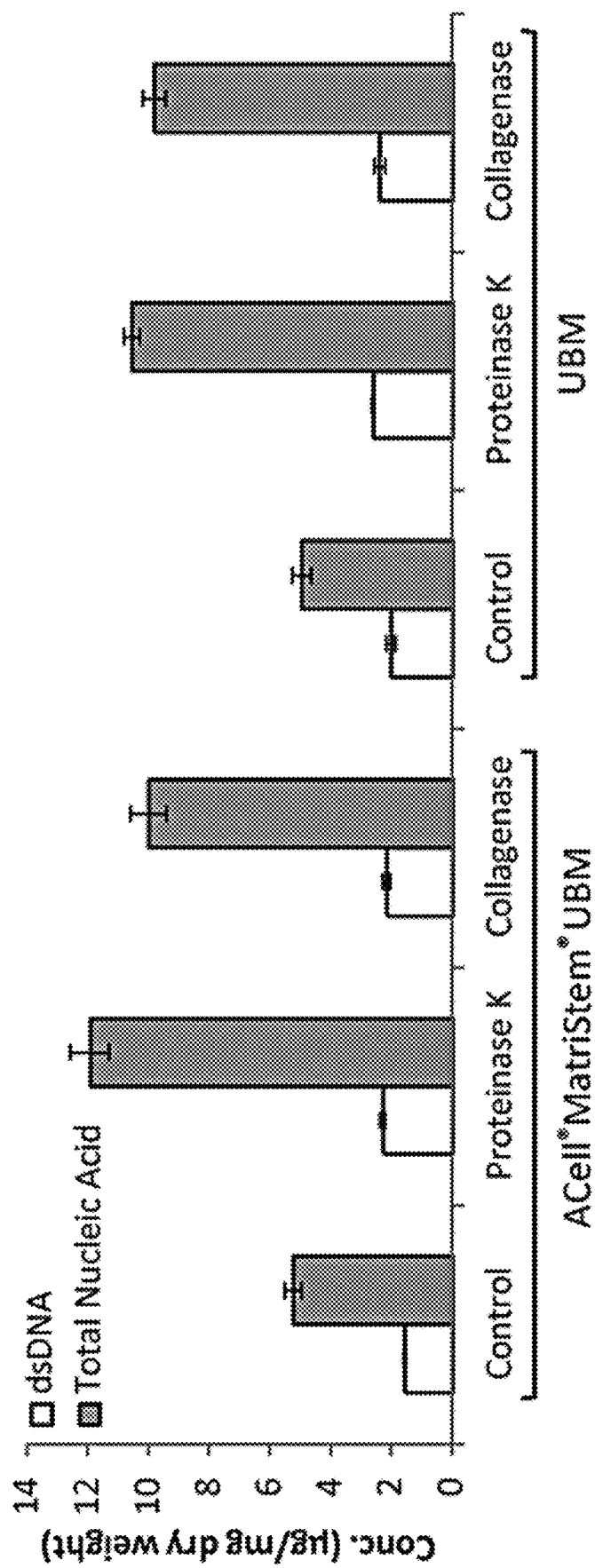
FIGS. 1A-1C. Comparison of nucleic acid concentration from UBM, SIS, or Dermis, and commercially available equivalents. Concentration of total nucleic acid and dsDNA per mg dry weight ECM scaffold from undigested and Proteinase K or Collagenase digested samples of (A) UBM, (B) SIS, and (C) Dermis samples. Total nucleic acid concentration was assessed by UV absorbance at 260 nm. The dsDNA concentration was assessed by picogreen dsDNA quantification reagent. Variability from isolation to isolation is depicted by standard deviation. Data are presented as means±s.d., n=3 isolations per sample.

The nucleic and amino acid sequences listed are shown using standard letter abbreviations for nucleotide bases and for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-96454-11_Sequence_Listing.txt, Jun. 28, 2022, 1.15 KB], which is incorporated by reference herein.

DETAILED DESCRIPTION

First identified by electron microscopy in 1967 as a product of platelets (Wolf, Br J Haematol. 1967; 13:269-288; Hargett et al., Pulm Circ. 2013; 3(2):329-40) extracellular vesicles (EV) are potent vehicles of intercellular communication due to their ability to transfer RNA, proteins, enzymes, and lipids, thereby affecting various physiological and pathological processes. Production and release of EVs is evolutionarily conserved in both prokaryotic and eukaryotic organisms, thus underscoring the importance of vesicle mediated processes in cell physiology (Deatherage and Cookson, Infect Immun. 2012 June; 80(6): 1948-1957). EVs are nanosized, matrix bound vesicles with diameters ranging from 50-1,000 nm and are categorized into three main groups: nanovesicles, exosomes, and apoptotic bodies, based upon their size, origin, and mode of release (Nawaz et al., Nat Rev Urol. 2014; 11(12):688-701; van der Pol et al., Pharmacol Rev. 2012; 64(3):676-705).

EVs are secreted by a variety of different cell types under various physiologic conditions and have been identified in biological fluids including saliva, urine, nasal and bronchial lavage fluid, amniotic fluid, breast milk, plasma, serum and seminal fluid (Yanez-Mo et al., J Extracell Vesicles. 2015; 4:27066). Although EVs have been identified in body fluids and cell culture supernatants, EVs are capable of anchoring to ECM constituents through the presence of adhesion molecules such as ICAM-1 and integrins, such as αM integrin and B2 integrins (Escola et al., J. Biol. Chem. 1998; 273 20121-20127; Thery et al., J. Cell Biol. 1999; 147:599-610; Thery et al., J. Immunol. 2001; 166: 7309-7318).

"Matrix vesicles" also have been shown to anchor selectively to the matrix of bone, cartilage and predentin (Anderson, J Cell Biol. 1969; 41:59-72; Anderson, Curr Rheumatol Rep. 2003; 5:222-226). More appropriately described as calcification vesicles, these membrane nanoparticles are the product of chondrocytes, osteoblasts and odontoblasts, and have been shown to serve as the initial site of calcification in all skeletal tissues (Anderson, Clin Orthop Relat Res. 1995; (314):266-80). However, it is still uncertain if matrix vesicles participate in intercellular signaling similar to exosomes and microvesicles (Sharpiro et al., Bone. 2015; 79:29-36). Disclosed herein is the surprising finding of nanovesicles tightly bound within the interstitial matrix of soft tissue, and specifically within the matrix of acellular bioscaffolds, namely the extracelluar matrix (ECM). These bioscaffolds are prepared by the removal of cells (decellularization) of source tissues such as urinary bladder, dermis, and small intestinal submucosa using methods specifically designed to lyse/rupture cell membranes and subsequently remove the cell debris. These nanovesicles can be used in regenerative medicine and tissue engineering strategies (De Jong et al, Front Immunol. 2014; 5:608; Malda et al.; Nat Rev Rheumatol. 2016 (Epub ahead of print); Lamichhane et al., Tissue Eng Part B Rev. 2015; 21(1):45-54). In addition to their potential therapeutic use in tissue repair, the composition, cargo and mechanism of regulated release provide novel implications for their utility as diagnostic and prognostic biomarkers to monitor physiological and pathological processes.

It is disclosed herein that nanovesicles, specifically exosomes, are embedded within, and bound to, laboratory produced ECM bioscaffolds and commercially available ECM bioscaffolds. The content of these nanovesicles was determined, and it was documented that they differentially affect particular target cells. The disclosed studies document that pharmaceutical compositions including these ECM-derived nanovesicles can be used to engineer bioscaffolds and medical devices. These pharmaceutical compositions also can be used to target growth, migration, and other biological properties of specific target cell populations.

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration: The introduction of a composition into a subject by a chosen route. The route can be local or systemic. For example, if the chosen route is intravenous, the composition is administered by introducing the composition into a vein of the subject. If the chosen route is local, the composition can be administered by introducing the composition into the tissue.

Alter: A statistically significant change in an effective amount or property of a substance of interest, such as a cell, polynucleotide or polypeptide. The change can be an increase or a decrease. The alteration can be in vivo or in vitro. In several embodiments, altering an effective amount of a substance is at least about a 50%, 60%, 70%, 80%, 90%, 95%, 96%, 97%, 98%, 99%, or 100% increase or decrease in the effective amount (level) of a substance, the proliferation and/or survival of a cells, or the activity of a proteins such as an enzyme.

Adenocarcinoma: A type of malignant tumor that can occur in several parts of the body. It is a neoplasia of epithelial tissue that has glandular origin, glandular characteristics, or both.

Apoptosis: A process of programmed cell death that occurs in multicellular organisms. Apoptosis includes characteristic cell changes (morphology) and death. These changes include blebbing, cell shrinkage, nuclear fragmentation, chromatin condensation, chromosomal DNA fragmentation, and global mRNA decay.

Biocompatible: Any material, that, when implanted in a mammalian subject, does not provoke an adverse response in the subject. A biocompatible material, when introduced into an individual, is able to perform its' intended function, and is not toxic or injurious to that individual, nor does it induce immunological rejection of the material in the subject.

Bioscaffold: A scaffold, usually a solid support or a gel, that is biocompatible.

Cancer: A benign or malignant tumor that has undergone characteristic anaplasia with loss of differentiation, increase rate of growth, invasion of surrounding tissue, and is capable of metastasis. For example, thyroid cancer is a tumor that arises in or from thyroid tissue, and esophageal cancer is a tumor that arises in or from esophageal tissue. Residual cancer is cancer that remains in a subject after any form of treatment given to the subject to reduce or eradicate the cancer. Metastatic cancer is a tumor at one or more sites in the body other than the site of origin of the original (primary) cancer from which the metastatic cancer is derived. Cancer includes, but is not limited to, solid tumors.

cDNA (complementary DNA): A piece of DNA lacking internal, non-coding segments (introns) and regulatory sequences that determine transcription. cDNA is synthesized in the laboratory by reverse transcription from messenger RNA extracted from cells. cDNA can also contain untranslated regions (UTRs) that are responsible for translational control in the corresponding RNA molecule.

Centrifugation: The process whereby a centrifugal force is applied to a mixture, whereby more-dense components of the mixture migrate away from the axis of the centrifuge relative to other less-dense components in the mixture. The force that is applied to the mixture is a function of the speed of the centrifuge rotor, and the radius of the spin. In most applications, the force of the spin will result in a precipitate (a pellet) to gather at the bottom of the centrifuge tube, where the remaining solution is properly called a "supernate" or "supernatant." In other similar applications, a density-based separation or "gradient centrifugation" technique is used to isolate a particular species from a mixture that contains components that are both more dense and less dense than the desired component.

During the circular motion of a centrifuge rotor, the force that is applied is the product of the radius and the angular velocity of the spin, where the force is traditionally expressed as an acceleration relative to "g," the standard acceleration due to gravity at the Earth's surface. The centrifugal force that is applied is termed the "relative centrifugal force" (RCF), and is expressed in multiples of "g."

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in *Harrison's Principles of Internal Medicine*, 14th edition; Perry et al., *Chemotherapy*, Ch. 17 in Abeloff, *Clinical Oncology* 2nd ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Chemotherapeutic agents include those known by those skilled in the art, including but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cisplatinum and the taxanes, such as taxol. Rapamycin has also been used as a chemotherapeutic.

Contacting: Placement in direct physical association. Includes both in solid and liquid form.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor-$\alpha$, interleukin (IL)-6, IL-10, IL-12, transforming growth factor, and interferon-$\gamma$.

Degenerate variant: A polynucleotide encoding a, polypeptide, such as a PDGF polypeptide, that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

Differentiation: Refers to the process whereby relatively unspecialized cells (e.g., embryonic cells) acquire specialized structural and/or functional features characteristic of mature cells. Similarly, "differentiate" refers to this process. Typically, during differentiation, cellular structure and functional capability alters and tissue-specific proteins and non-protein molecules appear.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Enriched: A process whereby a component of interest, such as a nanovesicle, that is in a mixture has an increased ratio of the amount of that component to the amount of other undesired components in that mixture after the enriching process as compared to before the enriching process. Extracellular matrix (ECM): A complex mixture of structural and functional biomolecules and/or biomacromolecules including, but not limited to, structural proteins, specialized proteins, proteoglycans, glycosaminoglycans, and growth factors that surround and support cells within tissues and, unless otherwise indicated, is acellular. ECM preparations can be considered to be "decellularized" or "acellular", meaning the cells have been removed from the source tissue through processes described herein and known in the art. By "ECM-derived material," such as an "ECM-derived nanovesicle," "Matrix bound nanovesicle" or "nanovesicle derived from an ECM" it is a nanovesicle that is prepared from a natural ECM or from an in vitro source wherein the ECM is produced by cultured cells and comprises one or more polymeric components (constituents). ECM-derived nanovesicles are defined below.

Expressed: The translation of a nucleic acid sequence into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Gel: A state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (for example, the shape is discrete enough to maintain three dimensions on a two dimensional surface). "Gelation time," also referred to as "gel time," refers to the time it takes for a composition to become non-flowable under modest stress.

Glioma: A tumor that arises from glial cells. Gliomas include ependymomas, astrocytomas, oligodendrogliomas, brainstem gliomas, optic nerve gliomas, and mixed gliomas. Gliomas can be characterized by grade. The World Health Organization (WHO) classifies gliomas as grade I-IV. Low-grade gliomas (WHO grade II) are well-differentiated (not anaplastic) that exhibit benign tendencies and generally have a better prognosis. However, they can reoccur and increase in grade over time so they are classified as malignant. High-grade (WHO grade III-IV) gliomas are undifferentiated or anaplastic. High grade gliomas are malignant and have a poor prognosis. Gliomas are supratentorial (above the tentorium, in the cerebrum, and mostly found in adults) inratentorial (below the tentorium, in the cerebellum, and mostly found in children), or pontine (located in the pons of the brainstem). The symptoms of gliomas depend on wherein the tumor is located within the central nervous system is affected. Symptoms of a brain glioma are headaches, vomiting, seizures, and cranial nerve disorders. A symptom of an optic nerve glioma is visual loss. Symptoms of spinal cord gliomas are pain, weakness, or numbness in the extremities. Generally, gliomas spread via the cerebrospinal fluid and can cause "drop metastases" to the spinal cord.

Growth factor: A substance that promotes cell growth, survival, and/or differentiation. Growth factors include molecules that function as growth stimulators (mitogens), molecules that function as growth inhibitors (e.g. negative growth factors) factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are a fibroblast growth factor (such as FGF-2), epidermal growth factor (EGF), ciliary neurotrophic factor (CNTF), and nerve growth factor (NGF), and actvin-A.

Inhibiting (or Treating) a Disease: Inhibiting the full development of a disease or condition or accelerating healing. "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, such as pain, a shortened recovery time or an improvement in the overall health or well-being of the subject, or by other parameters well known in the art that are specific to the particular disease.

Isolated: An "isolated" biological component (such as a nucleic acid, protein cell, or nanovesicle) has been substantially separated or purified away from other biological components in the cell of the organism or the ECM, in which the component naturally occurs. Nucleic acids and proteins that have been "isolated" include nucleic acids and proteins purified by standard purification methods. Nanovesicles that have been isolated are removed from the fibrous materials of the ECM. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, or can be included in a nanovesicle, or attached to a nanovesicle, to facilitate detection. Specific, non-limiting examples of labels include fluorescent tags, enzymatic linkages, and radioactive isotopes.

Macrophage: A type of white blood cell that phagocytoses and degrades cellular debris, foreign substances, microbes, and cancer cells. In addition to their role in phagocytosis, these cells play an important role in development, tissue maintenance and repair, and in both innate and adaptive immunity in that they recruit and influence other cells including immune cells such as lymphocytes. Macrophages can exist in many phenotypes, including phenotypes that have been referred to as M1 and M2. Macrophages that perform primarily pro-inflammatory functions are called M1 macrophages (CD86+/CD68+), whereas macrophages that decrease inflammation and encourage and regulate tissue repair are called M2 macrophages (CD206+/CD68+). The markers that identify the various phenotypes of macrophages vary among species. It should be noted that macrophage phenotype is represented by a spectrum that ranges between the extremes of M1 and M2.

Mammal: This term includes both human and non-human mammals. Similarly, the term "subject" includes both human and veterinary subjects.

Metastasis: Spread of cancer from one location to another in the body. Metastasis occurs by a complex series of steps wherein the cancer cells leave the original tumor site and migrate via the bloodstream, lymphatic system, the cerebral spinal fluid, or by extension.

MicroRNA: A small non-coding RNA that is about 17 to about 25 nucleotide bases in length, that post-transcriptionally regulates gene expression by typically repressing target mRNA translation. A miRNA can function as negative regulators, such that greater amounts of a specific miRNA will correlates with lower levels of target gene expression. There are three forms of miRNAs, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nucleotide overhang at the 3' end. The cleavage product, the premature miRNA (pre-miRNA) is about 60 to about 110 nucleotides long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nucleotides in length.

Nanovesicle: An extracellular vesicle that is a nanoparticle of about 10 to about 1,000 nm in diameter. Nanovesicles are lipid membrane bound particles that carry biologically active signaling molecules (e.g. microRNAs, proteins) among other molecules. Generally, the nanovesicle is limited by a lipid bilayer, and the biological molecules are enclosed and/or can be embedded in the bilayer. Thus, a nanovesicle includes a lumen surrounded by plasma membrane. The different types of vesicles can be distinguished based on diameter, subcellular origin, density, shape, sedimentation rate, lipid composition, protein markers, nucleic acid content and origin, such as from the extracellular matrix or secreted. A nanovesicle can be identified by its origin, such as a matrix bound nanovesicle from an ECM (see above) and/or the miR content.

An "exosome" is a membranous vesicle which is secreted by a cell, and ranges in diameter from 10 to 150 nm. Generally, late endosomes or multivesicular bodies contain intralumenal vesicles which are formed by the inward budding and scission of vesicles from the limited endosomal membrane into these enclosed nanovesicles. These intralumenal vesicles are then released from the multivesicular body lumen into the extracellular environment, typically into a body fluid such as blood, cerebrospinal fluid or saliva, during exocytosis upon fusion with the plasma membrane. An exosome is created intracellularly when a segment of membrane invaginates and is endocytosed. The internalized segments which are broken into smaller vesicles and ultimately expelled from the cell contain proteins and RNA molecules such as mRNA and miRNA. Plasma-derived exosomes largely lack ribosomal RNA. Extra-cellular matrix derived exosomes include specific miRNA and protein components, and have been shown to be present in virtually every body fluid such as blood, urine, saliva, semen, and cerebrospinal fluid.

A "nanovesicle derived from an ECM" "matrix bound nanovesicle" or an "ECM-derived nanovesicle" are membrane bound particles ranging in size from 10 nm-1000 nm, present in the extracellular matrix, which contain biologically active signaling molecules such as protein, lipids, nucleic acid, growth factors and cytokines that influence cell behavior. The terms are interchangeable, and refer to the same vesicles. These nanovesicles are embedded within, and bound to, the ECM and are not just attached to the surface. These nanovesicles are resistant harsh isolation conditions, such as freeze thawing and digestion with proteases such as pepsin, elastase, hyaluronidase, proteinase K, and collagenase, and digestion with detergents. Generally, these nanovesicles are enriched for miR-145 and optionally miR-181, miR-143, and miR-125, amongst others. These nanovesicles do not express CD63 or CD81, or express barely detectable levels of these markers ($CD63^{lo}CD81^{lo}$). The ECM can be an ECM from a tissue, can be produced from cells in culture, or can be purchased from a commercial source.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand." Sequences on a nucleic acid sequence which are located 5' to sequence of interest are referred to as "upstream sequences;" sequences a nucleotide sequence which are located 3' to the sequence of interest are referred to as "downstream sequences."

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together, such as in a wild-type gene. This includes nucleic acid vectors comprising an amplified or assembled nucleic acid which can be used to transform a suitable host cell. In one example, a recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, such as by genetic engineering techniques. A host cell that includes the recombinant nucleic acid is referred to as a "recombinant host cell." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence. Thus, the two sequences are complementary.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, PA, 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymer: Molecules composed of repeating monomer units, including homopolymers, block copolymers, random copolymers, and graft copolymers. "Polymers" also include linear polymers as well as branched polymers, with branched polymers including highly branched, dendritic, and star polymers. A "polymerizing initiator" refers to any substance or stimulus, that can initiate polymerization of monomers or macromers by free radical generation. Exemplary polymerizing initiators include electromagnetic radiation, heat, and chemical compounds.

Polypeptide: Any chain of amino acids, regardless of length or post-translational modification (such as glycosylation or phosphorylation). A "residue" refers to an amino acid or amino acid mimetic incorporated in a polypeptide by an amide bond or amide bond mimetic, the "position" of the residue indicates its place in the amino acid sequence. A polypeptide has an amino terminal (N-terminal) end and a carboxy terminal end.

A conservative substitution in a polypeptide is a modification that involves the substitution of one or more amino acids for amino acids having similar biochemical properties that do not result in change or loss of a biological or biochemical function of the polypeptide are designated "conservative" substitutions. These conservative substitutions are likely to have minimal impact on the activity of the resultant protein. Table 1 shows amino acids that can be substituted for an original amino acid in a protein, and which are regarded as conservative substitutions.

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

One or more conservative changes, or up to ten conservative changes (such as two substituted amino acids, three substituted amino acids, four substituted amino acids, or five substituted amino acids, etc.) can be made in the polypeptide without changing a biochemical function of the protein, such as a growth factor or cytokine.

Preventing or treating a disease: "Preventing" a disease refers to inhibiting the partial or full development of a disease, for example in a person who is known to have a predisposition to a disease such as a cancer. An example of a person with a known predisposition is someone with a history of breast cancer in the family, or who has been exposed to factors that predispose the subject to a condition, such as melanoma. "Treatment" refers to a therapeutic intervention that ameliorates a sign or symptom of a disease or pathological condition after it has begun to develop. In several embodiments, treatment refers to a reduction in size of a tumor, a decrease in the number and/or size of metastases, or a decrease in a symptom of the tumor.

Proliferation: Division of cells such that they increase in number. The process of cell division is called mitosis.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (for example, a metallothionein promoter) or from mammalian viruses (for example, the retrovirus long terminal repeat; the adenovirus late promoter; the vaccinia virus 7.5K promoter). Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Scaffold: A structure, usually comprising a biocompatible material, which provides a surface suitable for adherence and proliferation of cells, and also provides stability and support. A scaffold can be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, and amorphous shapes. Scaffolds can also serve as inductive templates that release bioactive molecules, such as ECM scaffolds that release bioactive molecules during the process of degradation.

Stem cell: A cell that is self-renewing and can generate a fully differentiated functional cell of one or more than one given cell type. The role of stem cells in vivo is to replace cells that die or are destroyed during the normal life of an animal. Generally, stem cells can divide without limit and are totipotent. After division, the stem cell may remain as a stem cell, become a precursor cell, or proceed to terminal differentiation.

Generally, precursor cells can divide and can be pluripotent. After division, a precursor cell can remain a precursor cell, or may proceed to terminal differentiation. A "somatic precursor cell" is a cell that can generate a fully differentiated functional cell of at least one given cell type from the body of an animal, such as a human. A neuronal precursor cell can generate of fully differentiated neuronal cell, such as, but not limited to, and adrenergic or a cholinergic neuron. A hematopoietic stem cell gives rise to cells of the blood.

Therapeutically effective amount: A quantity of a specific substance, such as a nanovesicle, sufficient to achieve a desired effect in a subject being treated. When administered to a subject, a dosage will generally be used that will achieve target tissue concentrations (for example, in bone) that has been shown to achieve a desired in vitro effect.

Transplanting: The placement of a biocompatible substrate, such as a nanovesicle, into a subject in need thereof.

Tumor: An abnormal growth of cells, which can be benign or malignant. A malignant type of tumor, is generally characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In one non-limiting example, a tumor is a glioma.

Ultrafiltration: A type of membrane filtration in which forces (such as pressure or concentration gradients) lead to a separation through a semipermeable membrane. Ultrafiltration membranes are typically characterized by the molecular weight cut off (MWCO) of the membrane. Suspended solids and solutes of higher molecular weight are retained in the retentate, while water and lower molecular weight solutes pass through the membrane in the permeate. Different types of modules can be used for ultrafiltration processes. Examples of such modules are tubular elements that use polymeric membranes cast on the inside of plastic or paper tubes; hollow fiber designs that contain multiple hollow fibers; spiral wound modules in which flat membrane sheets are separated by a thin meshed spacer material that is rolled around a central perforated tube and fitted into a tubular steel pressure vessel casing; and plate and frame assemblies that use a membrane placed on a flat plate separated by a mesh like material through which the filtrate passes.

Vector: A nucleic acid molecule that can be introduced into a host cell, thereby producing a transformed host cell. A vector may include nucleic acid sequences that permit it to replicate in a host cell, such as an origin of replication. A vector may also include one or more selectable marker genes and other genetic elements known in the art. Vectors can be viral vectors, such as adenoviral, retroviral, or lentiviral vectors. Vectors can be non-viral vectors, such as Sleeping Beauty plasmids or Prince Charming plasmids.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, "A or B" is intended to include "A," "B" and "A and B" unless the context clearly indicates otherwise. Unless indicated otherwise, "about" indicates within 5 percent. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification,

Nanovesicles Derived from an Extracellular Matrix (ECM)

It is disclosed herein that nanovesicles are embedded in the extracellular matrix. These nanovesicles can be isolated and are biologically active. Thus, these nanovesicles can be used for therapeutic purposes, either alone or with another ECM. These nanovesicles can be used in biological scaffolds, either alone or with another ECM. These nanovesicles are also of use in vitro, such as to alter the proliferation, differentiation and/or migration of cells.

An extracellular matrix is a complex mixture of structural and functional biomolecules and/or biomacromolecules including, but not limited to, structural proteins, specialized proteins, proteoglycans, glycosaminoglycans, and growth factors that surround and support cells within mammalian tissues and, unless otherwise indicated, is acellular. Generally, the disclosed matrix bound nanovesicles are embedded in any type of extracellular matrix (ECM), and can be isolated from this location. Thus, the disclosed matrix bound nanovesicles are not detachably present on the surface of the ECM.

Extracellular matrices are disclosed, for example and without limitation, in U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666; each of which is incorporated by reference in its entirety). However, an ECM can be produced from any tissue, or from any in vitro source wherein the ECM is produced by cultured cells and comprises one or more polymeric components (constituents) of native ECM. ECM preparations can be considered to be "decellularized" or "acellular", meaning the cells have been removed from the source tissue or culture.

In some embodiments, the ECM is isolated from a vertebrate animal, for example, from a mammalian vertebrate animal including, but not limited to, human, monkey, pig, cow, sheep, etc. The ECM may be derived from any organ or tissue, including without limitation, urinary bladder, intestine, liver, heart, esophagus, spleen, stomach and dermis. In specific non-limiting examples, the extracellular matrix is isolated from esophageal tissue, urinary bladder, small intestinal submucosa, dermis, umbilical cord, pericardium, cardiac tissue, or skeletal muscle. The ECM can comprise any portion or tissue obtained from an organ, including, for example and without limitation, submucosa, epithelial basement membrane, *Tunica propria*, etc. In one non-limiting embodiment, the ECM is isolated from urinary bladder. In some embodiments, the ECM is from tumor tissue.

The ECM may or may not include the basement membrane. In another non-limiting embodiment, the ECM includes at least a portion of the basement membrane. The ECM material may or may not retain some of the cellular elements that comprised the original tissue such as capillary endothelial cells or fibrocytes. In some embodiments, the ECM contains both a basement membrane surface and a non-basement membrane surface.

In one non-limiting embodiment, the ECM is harvested from porcine urinary bladders (also known as urinary bladder matrix or UBM). Briefly, the ECM is prepared by removing the urinary bladder tissue from a mammal, such as a pig, and trimming residual external connective tissues, including adipose tissue. All residual urine is removed by repeated washes with tap water. The tissue is delaminated by first soaking the tissue in a deepithelializing solution, for example and without limitation, hypertonic saline (e.g. 1.0 $N$ saline), for periods of time ranging from ten minutes to four hours. Exposure to hypertonic saline solution removes the epithelial cells from the underlying basement membrane. Optionally, a calcium chelating agent may be added to the saline solution. The tissue remaining after the initial delamination procedure includes the epithelial basement membrane and tissue layers abluminal to the epithelial basement membrane. The relatively fragile epithelial basement membrane is invariably damaged and removed by any mechanical abrasion on the luminal surface. This tissue is next subjected to further treatment to remove most of the abluminal tissues but maintain the epithelial basement membrane and the *Tunica propria*. The outer serosal, adventitial, tunica muscularis mucosa, tunica submucosa and most of the muscularis mucosa are removed from the remaining deepithelialized tissue by mechanical abrasion or by a combination of enzymatic treatment (e.g., using trypsin or collagenase) followed by hydration, and abrasion. Mechanical removal of these tissues is accomplished by removal of mesenteric tissues with, for example and without limitation, Adson-Brown forceps and Metzenbaum scissors and wiping away the tunica muscularis and tunica submucosa using a longitudinal wiping motion with a scalpel handle or other rigid object wrapped in moistened gauze. Automated robotic procedures involving cutting blades, lasers and other methods of tissue separation are also contemplated. After these tissues are removed, the resulting ECM consists mainly of epithelial basement membrane and subjacent *Tunica propria*.

In another embodiment, the ECM is prepared by abrading porcine bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. Care is taken to prevent perforation of the submucosa. After these tissues are removed, the resulting ECM consists mainly of the tunica submucosa (see FIG. 2 of U.S. Pat. No. 9,277,999, which is incorporated herein by reference.

ECM can also prepared as a powder. Such powder can be made according the method of Gilbert et al., Biomaterials 26 (2005) 1431-1435, herein incorporated by reference in its entirety. For example, UBM sheets can be lyophilized and then chopped into small sheets for immersion in liquid nitrogen. The snap frozen material can then be comminuted so that particles are small enough to be placed in a rotary knife mill, where the ECM is powdered. Similarly, by precipitating NaCl within the ECM tissue the material will fracture into uniformly sized particles, which can be snap frozen, lyophilized, and powdered.

In one non-limiting embodiment, the ECM is derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton Mass.). In another non-limiting embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.). In another embodiment, the ECM is derived from urinary bladder. Commercially available preparations include, but are not limited to UBM (ACell Corporation; Jessup, Md.).

Nanovesicles can be derived from (released from) an extracellular matrix using the methods disclosed below. In some embodiments, the ECM is digested with an enzyme, such as pepsin, collagenase, elastase, hyaluronidase, or proteinase K, and the nanovesicles are isolated. In other embodiments, the nanovesicles are released and separated from the ECM by changing the pH with solutions such as glycine HCL, citric acid, ammonium hydroxide, use of chelating agents such as, but not limited to, EDTA, EGTA, by ionic strength and or chaotropic effects with the use of salts such as, but not limited to potassium chloride (KCl), sodium chloride, magnesium chloride, sodium iodide, sodium thiocyanate, or by exposing ECM to denaturing conditions like guanidine HCl or Urea.

In some embodiments, the nanovesicles are not in their natural environment, and thus have properties that differ from naturally occurring nanovesicles. In particular examples, the nanovesicles are prepared following digestion of an ECM with an enzyme, such as pepsin, elastase, hyalunornidase, proteinase K, salt solutions, or collagenase. The ECM can be freeze-thawed, or subject to mechanical degradation.

In some embodiments, expression of CD63 and/or CD81 cannot be detected on the nanovesicles. Thus, the nanovesicles do not express CD63 and/or CD81. In a specific example, CD63 and CD81 cannot be detected on the nanovesicles. In other embodiments, the nanovesicles are express barely detectable levels of CD63 and CD81, such as that detectable by Western blot. These nanovesicles are $CD63^{lo}CD81^{lo}$. One of skill in the art can readily identify nanovesicles that are $CD63^{lo}CD81^{lo}$, using, for example, antibodies that specifically bind CD63 and CD81. A low level of these markers can be established using procedures such as fluorescent activated cell sorting (FACS) and fluorescently labeled antibodies to determine a threshold for low and high amounts of CD63 and CD81. The disclosed nanovesicles differ from nanovesicles that may be transiently attached to the surface of the ECM due to the presence of nanovesicles in biological fluids. In some embodiments, the outer surface of the nanovesicles has been subjected to a decellularization process, which can include the use of enzymes and/or detergents.

In certain embodiments, the nanovesicles comprise one or more miRNA. In specific non-limiting examples, the nanovesicles comprise miR-145 and miR-181. MIR-145 and miR-181 are known in the art. The miR-145 nucleic acid sequence is provided in MiRbase Accession No. MI0000461, incorporated herein by reference. A miR-145 nucleic acid sequence is CACCUUGUCCUCACGGU-CCAGUUUUCCCAGGAAUCCCUUAGAUGC-UAAGAUGGGGA UUCCUGGAAAAUACUGUUC-UUGAGGUCAUGGUU (SEQ ID NO: 1). An miR-181 nucleic acid sequence is provided a miRbase Accession No. MI0000269, incorporated herein by reference. A miR-181 nucleic acid sequence is:

(SEQ ID NO: 2)
AGAAGGGCUAUCAGGCCAGCCUUCAGAGGACUCCAAGGAACAUUCAACGC

UGUCGGUGAGUUUGGGAUUUGAAAAAACCACUGACCGUUGACUGUACCUU

GGGGUCCUUA.

The nanovesicles disclosed herein can be formulated into compositions for pharmaceutical delivery, and used in bioscaffolds and devices, as discussed below. The nanovesicles are of use in a number of methods, which are also disclosed below.

Isolation of Nanovesicles from the ECM

Methods of isolating nanovesicles from an ECM are disclosed herein. In some embodiments, these methods include digesting the ECM with an enzyme to produce digested ECM. In specific embodiments, the ECM is digested with pepsin, elastase, hyaluronidase, collagenase and/or proteinase K. In other embodiments, the ECM is treated with a detergent. In further embodiments, the method does not include the use of enzymes. In specific non-limiting examples, the methods utilizes chaotropic agents or ionic strength to isolate nanovesicles such as salts, such as potassium chloride. In additional embodiments, the ECM can be manipulated to increase nanovesicle content prior to isolation of nanovesicles.

In some embodiments, the ECM is digested with an enzyme. The ECM can be digested with the enzyme for about 12 to about 48 hours, such as about 12 to about 36 hours. The ECM can be digested with the enzyme for about 12, about 24 about 36 or about 48 hours. In one specific non-limiting example, the ECM is digested with the enzyme at room temperature. However, the digestion can occur at about 4° C., or any temperature between about 4° C. and 25° C. Generally, the ECM is digested with the enzyme for any length of time, and at any temperature, sufficient to remove collagen fibrils. The digestion process can be varied depending on the tissue source. Optionally, the ECM is processed by freezing and thawing, either before or after digestion with the enzyme. The ECM can be treated with detergents, including ionic and/or non-ionic detergents.

The digested ECM is then processed, such as by centrifugation, to isolate a fibril-free supernatant. In some embodiments the digested ECM is centrifuged, for example, for a first step at about 300 to about 1000 g. Thus, the digested ECM can be centrifuged at about 400 g to about 750 g, such as at about 400 g, about 450 g, about 500 g or about 600 g. This centrifugation can occur for about 10 to about 15 minutes, such as for about 10 to about 12 minutes, such as for about 10, about 11, about 12, about 14, about 14, or about 15 minutes. The supernatant including the digested ECM is collected.

In some embodiments, digested ECM also can be centrifuged for a second step at about 2000 g to about 3000 g. Thus, the digested ECM can be centrifuged at about 2,500 g to about 3,000 g, such as at about 2,000 g, 2,500 g, 2,750 g or 3,000 g. This centrifugation can occur for about 20 to about 30 minutes, such as for about 20 to about 25 minutes, such as for about 20, about 21, about 22, about 23, about 24, about 25, about 26, about 27, about 28, about 29 or about 30 minutes. The supernatant including the digested ECM is collected.

In additional embodiments, the digested ECM can be centrifuged for a third step at about 10,000 to about 15,000 g. Thus, the digested ECM can be centrifuged at about 10,000 g to about 12,500 g, such as at about 10,000 g, 11,000 g or 12,000 g. This centrifugation can occur for about 25 to about 40 minutes, such as for about 25 to about 30 minutes, for example for about 25, about 26, about 27, about 28, about 29, about 30, about 31, about 32, about 33, about 34, about 35, about 36, about 37, about 38, about 39 or about 40 minutes. The supernatant including the digested ECM is collected.

One, two or all three of these centrifugation steps can be independently utilized. In some embodiments, all three centrifugation steps are utilized. The centrifugation steps can be repeated, such as 2, 3, 4, or 5 times. In one embodiment, all three centrifugation steps are repeated three times.

In some embodiments, the digested ECM is centrifuged at about 500 g for about 10 minutes, centrifuged at about 2,500 g for about 20 minutes, and/or centrifuged at about 10,000 g for about 30 minutes. These step(s), such as all three steps are repeated 2, 3, 4, or 5 times, such as three times. Thus, in one non-limiting example, the digested ECM is centrifuged at about 500 g for about 10 minutes, centrifuged at about 2,500 g for about 20 minutes, and centrifuged at about 10,000 g for about 30 minutes. These three steps are repeated three times. Thus, a fibril-free supernatant is produced.

The fibril-free supernatant is then centrifuged to isolate the nanovesicles. In some embodiments, the fibril-free supernatant is centrifuged at about 100,000 g to about 150,000 g. Thus, the fibril-free supernatant is centrifuged at about 100,000 g to about 125,000 g, such as at about 100,000 g, about 105,000 g, about 110,000 g, about 115,000 g or about 120,000 g. This centrifugation can occur for about 60 to about 90 minutes, such as about 70 to about 80 minutes, for example for about 60, about 65, about 70, about 75, about 80, about 85 or about 90 minutes. In one non-limiting example, the fiber-free supernatant is centrifuged at about 100,000 g for about 70 minutes. The solid material is collected, which is the nanovesicles. These nanovesicles then can be re-suspended in any carrier of interest, such as, but not limited to, a buffer.

In further embodiments the ECM is not digested with an enzyme. In these methods, ECM is suspended in an isotonic saline solution, such as phosphate buffered saline. Salt is then added to the suspension so that the final concentration of the salt is greater than about 0.1 M. The concentration can be, for example, up to about 3 M, for example, about 0.1 M salt to about 3 M, or about 0.1 M to about 2M. The salt can be, for example, about 0.1M, 0.15M, 0.2M, 0.3M, 0.4 M, 0.7 M, 0.6 M, 0.7 M, 0.8M., 0.9M, 1.0 M, 1.1 M, 1.2 M, 1.3 M, 1.4 M, 1.5M, 1.6 M, 1.7 M, 1.8M, 1.9 M, or 2M. In some non-limiting examples, the salt is potassium chloride, sodium chloride or magnesium chloride. In other embodiments, the salt is sodium chloride, magnesium chloride, sodium iodide, sodium thiocyanate, a sodium salt, a lithium salt, a cesium salt or a calcium salt.

In some embodiments, the ECM is suspended in the salt solution for about 10 minutes to about 2 hours, such as about 15 minutes to about 1 hour, about 30 minutes to about 1 hour, or about 45 minutes to about 1 hour. The ECM can be suspended in the salt solution for about 15, 20, 25, 30, 35, 40, 45, 50, 55, 60, 65, 70, 75, 80, 85, 90, 95, 100, 105, 110, 115 or 120 minutes. The ECM can be suspended in the salt solution at temperatures from 4° C. to about 50° C., such as, but not limited to about 4° C. to about 25° C. or about 4° C. to about 37° C. In a specific non-limiting example, the ECM is suspended in the salt solution at about 4° C. In other specific non-limiting examples, the ECM is suspended in the salt solution at about 25° C. (room temperature). In further non-limiting examples, the ECM is suspended in the salt solution at about 37° C.

In some embodiments, the method includes incubating an extracellular matrix at a salt concentration of greater than about 0.4 M; centrifuging the digested extracellular matrix to remove collagen fibril remnants, and isolating the supernatant; centrifuging the supernatant to isolate the solid materials; and suspending the solid materials in a carrier, thereby isolating nanovesicles from the extracellular matrix.

Following incubation in the salt solution, the ECM is centrifuged to remove collagen fibrils. In some embodiments, digested ECM also can be centrifuged at about 2000 g to about 5000 g. Thus, the digested ECM can be centrifuged at about 2,500 g to about 4,500 g, such as at about 2,500 g, about 3,000 g, 3,500, about 4,000 g, or about 4,500 g. In one specific non-limiting example, the centrifugation is at about 3,500 g. This centrifugation can occur for about 20 to about 40 minutes, such as for about 25 to about 35 minutes, such as for about 20, about 21, about 22, about 23, about 24, about 25, about 26, about 27, about 28, about 29, about 30 minutes, about 31, about 32, about 33 about 34 or about 35 minutes. The supernatant is then collected.

In additional embodiments, the supernatant then can be centrifuged for a third step at about 100,000 to about 150,000 g. Thus, the digested ECM can be centrifuged at about 100,000 g to about 125,000 g, such as at about 100,000 g, 110,000 g or 120,000 g. This centrifugation can occur for about 30 minutes to about 2.5 hour, such as for about 1 hour to about 3 hours, for example for about 30 minutes, about 45 minutes, about 60 minutes, about 90 minutes, or about 120 minutes (2 hours). The solid materials are collected and suspended in a solution, such as buffered saline, thereby isolating the nanovesicles.

In yet other embodiments, the ECM is suspended in an isotonic buffered salt solution, such as, but not limited to, phosphate buffered saline. Centrifugation or other methods can be used to remove large particles (see below). Ultrafiltration is then utilized to isolate matrix bound nanovesicles from the ECM, particles between about 10 nm and about 10,000 nm, such as between about 10 and about 1,000 nm, such as between about 10 nm and about 300 nn.

In specific non-limiting examples, the isotonic buffered saline solution has a total salt concentration of about 0.164 mM, and a pH of about 7.2 to about 7.4. In some embodiments, the isotonic buffered saline solution includes 0.002 M KCl to about 0.164 M KCL, such as about 0.0027 M KCl (the concentration of KCL in phosphate buffered saline). This suspension is then processed by ultracentrifugation.

Following incubation in the isotonic buffered salt solution, the ECM is centrifuged to remove collagen fibrils. In some embodiments, digested ECM also can be centrifuged at about 2000 g to about 5000 g. Thus, the digested ECM can be centrifuged at about 2,500 g to about 4,500 g, such as at about 2,500 g, about 3,000 g, 3,500, about 4,000 g, or about 4,500 g. In one specific non-limiting example, the centrifugation is at about 3,500 g. This centrifugation can occur for about 20 to about 40 minutes, such as for about 25 to about 35 minutes, such as for about 20, about 21, about 22, about 23, about 24, about 25, about 26, about 27, about 28, about 29, about 30 minutes, about 31, about 32, about 33 about 34 or about 35 minutes.

Microfiltration and centrifugation can be used and combined to remove large molecular weight materials from the suspension. In one embodiment, large size molecule materials, such as more than 200 nm are removed using microfiltration. In another embodiment, large size materials are removed by the use of centrifugation. In a third embodiment both microfiltration and ultracentrifugation are used to remove large molecular weight materials. Large molecular weight materials are removed from the suspended ECM, such as materials greater than about 10,000 nm, greater than about 1,000 nm, greater than about 500 nm, or greater than about 300 nm. The effluent for microfiltration or the supernatant is then subjected to ultrafiltration. Thus, the effluent, which includes particle of less than about 10,000 nm, less than about 1,000 nm, less than about 500 nm, or less than about 300 nm is collected and utilized. This effluent is then subjected to ultrafiltration with a membrane with a molecular weight cutoff (MWCO) of 3,000 to 100,000. 100,000MWCO was used in the example Methods of Use Nanovesicles, such as exosomes, directionally home to specific target cells, dependent on the physical properties of their membranes. Thus, nanovesicles can be used for the delivery of their contents. In addition, matrix bound nanovesicles can be used to induce cell proliferation, differentiation, and migration of cells. They can also be used to maintain a cell in an undifferentiated state. The effect of the disclosed nanovesicles can be local, regional or systemic. Thus, these nanovesicles are of use both in vitro and in vivo.

Nanovesicles, such as exosmes, are enriched in specific mRNA, miRNA and proteins (Bobrie, et al., 2011). This cargo is protected from degradation by proteases and RNases while the vesicle is in the interstitial space, and retains bioactivity once taken up by a recipient cell. In this way, they facilitate the transfer of interactive signaling and enzymatic activities that would otherwise be restricted to individual cells based on gene expression (Lee, et al., 2011).

ECM-derived nanovesicles can be used to transfer their contents, including but not limited to RNA and DNA, to recipient cells. These molecules can be endogenous, or can be introduced using molecular techniques into the ECM-derived nanovesicle.

In certain embodiments, the ECM-derived nanovesicles can be loaded with therapeutic agents such as nucleic acid molecules or proteins. These can include exogenous nucleic acids, such as promoter operably linked to a nucleic acid encoding a protein. An expression vector can also be incorporated into the ECM-derived nanovesicles. To achieve incorporation of nucleic acid molecules of interest, methods of use include, but are not limited to (see U.S. Published Patent Application No. 2015/0216899, incorporated herein by reference):

(a) Electroporation. By this method, a number of holes are made in nanovesciels by briefly shocking them with an electric field of 100-200 V/cm. The DNA/RNA can enter through the holes made by the electric field.

(b) Lipofection. The method commonly called transfection and can be used to transform nanovesicles with DNA/RNA via very small vesicles containing the desired genetic constructs. The vesicles fuse with the membrane (similar to how two oil spots at the top of a broth will fuse) and the contents of the vesicles and the cells are combined. There are a number of transfection kits in the market, ready for use, e.g. DELIVERX™ siRNA Transfection Kit (cat. No. DX0002) from Panomics, FUGENE® HD Transfection Reagent (Cat. no. 04709691001) from Roche and LIPO-FECTAMINE™ 2000 (Cat. No. 11668-027) from Invitrogen.

(c) Transformation using heat shock. Chilling nanovesicles in the presence of divalent cations such as $Ca^{2+}$ (in $CaCl_2$)) makes their membranes become permeable to RNA or DNA plasmids or fragments. Nanovesicles are incubated with the DNA and then briefly heat shocked (42° C. for 30-120 seconds), which causes the DNA to enter the nanovesicle. This method may work well for condensed circular plasmid DNAs and may work for exosomal or lipid nanovesicle constituents.

In some embodiments the isolated ECM-derived nanovesicles (matrix bound nanovesicles) can be loaded with externally added therapeutic agents, such as nucleic acids or protein molecules. The nucleic acids may be DNA or RNA, such as siRNA, miRNA, or mRNA. In certain aspects, the isolated exosomes may comprise miRNAs. The miRNA can be, for example, additional amounts of miR-145 and/or miR-181. The ECM-derived nanovesicles can be loaded with proteins, growth factors or small molecules.

In some embodiments, the nanovesicles can be engineered to contain RNA/DNA or modified to contain a gene of interest and can be isolated and transferred to the recipient cells, to affect their biological function or survival. Consequently, the nanovesicles can deliver their content into the cytoplasm of the target cells, which in turn leads to translation of mRNA to specific proteins in the target cell. Further, nanovesicles are capable of carrying and transferring small coding and non-coding RNA such as microRNA and siRNA that can regulate translation of a specific gene.

In some embodiments, the nucleic acid encodes a polypeptide. Suitable polypeptides include, but are not limited to, a growth factor, an enzyme, a cytokine or a hormone. Suitable growth factors include human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factors (FGFs) such as FGF-α and FGF-β; prolactin; placental lactogen, a tumor necrosis factor; mullerian-inhibiting substance; mouse gonadotropin-associated peptide; inhibin; activin; vascular endothelial growth factor; integrin; thrombopoietin (TPO); nerve growth factor; platelet-growth factor; transforming growth factors (TGFs) such as TGF-α and TGF-β; insulin-like growth factor-I and —II; erythropoietin (EPO); osteoinductive factors; interferons such as interferon-α, β and γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-10, IL-11, IL-12; IL-13, IL-14, IL-15, IL-16, IL-17, IL-18, LIF, G-CSF, GM-CSF, M-CSF, EPO, kit-ligand, FLT-3 or MDA-7. Examples of hormones include, but are not limited to, growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, .beta.-endorphin, .beta.-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, and thyrotropin releasing hormone. Suitable enzymes include ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, or a reporter gene.

In some embodiments, the ECM-derived nanovesicles can be included in a pharmaceutical composition, such as including a pharmaceutically acceptable carrier, and can be administered to a subject by any method known to those of ordinary skill in the art. Examples include intravenously, nasally, intradermally, intraarterially, intraperitoneally, intralesionally, intracranially, intraarticularly, intraprostatically, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, directly into a heart chamber, directly injected into the organ or portion of organ or diseased site of interest, or by other method or any combination of these methods. Topical administration may be particularly advantageous for the treatment of the skin, such as cancer, to prevent chemotherapy-induced alopecia or other dermal hyperproliferative disorder. Alternatively, administration may be by orthotopic, intradermal, subcutaneous, intramuscular, intraperitoneal or intravenous injection.

For in vivo uses, compositions can be administered as pharmaceutically acceptable compositions that include physiologically acceptable carriers, buffers or other excipients. In some embodiments, the composition is formulated a liquid. In other embodiments, the composition is formulated a gel or a powder. In other embodiments, the composition is formulated as a mist, such as in a nebulizer. The further embodiments, the composition can be formulated as a gel or a time-release capsule. For treatment of conditions of the lungs, aerosol delivery can be used. Volume of an aerosol is generally between about 0.01 ml and about 0.5 ml.

The disclosed methods can include administering a composition to a subject containing about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 445, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg) of nanovesicles, or any range derivable therein. The above numerical values may also be the dosage that is administered to the patient based on the patient's weight, expressed as ng/kg, ug/kg, mg/kg, or g/kg, and any range derivable from those values.

Alternatively, the composition may have a concentration of nanovesicles that are 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 ng/ml, ug/ml, mg/ml, or g/ml, or any range derivable therein. The dose can be varied, depending on the condition to be treated. In some embodiments, the condition is a hernia, a torn or damaged muscle, a torn or damaged tendon, or stroke.

The composition may be administered to (or taken by) the subject 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein. The composition can be administered once daily, twice daily, three times daily, four times daily, five times daily, or six times daily (or any range derivable therein) and/or as needed to the patient. Alternatively, the composition can be administered every 2, 4, 6, 8, 12 or 24 hours (or any range derivable therein) to or by the subject. In some embodiments, the subject is administered the composition for a certain period of time or with a certain number of doses after experiencing symptoms.

The actual dosage amount of a composition administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject. In some embodiments, the condition is a hernia, a torn or damaged muscle, a torn or damaged tendon, or stroke.

The compositions including ECM-derived nanovesicles, for use in the disclosed methods, are suitably contained in a pharmaceutically acceptable carrier. The carrier is non-toxic, biocompatible and is selected so as not to detrimentally affect the biological activity of the nanovesicle. The ECM-derived nanovesicle can be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Local administration of the compositions are appropriate such as by coating medical devices (see below). Additional active ingredients can be added to these compositions, such as, but not limited to, chemotherapeutic agents (see below). The ECM-derived nanovesicles can also be attached to a surface, such as, but not limited to, a polypropylene mesh or any biocompatible material.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). In some embodiments, the composition of use includes a buffer, a hydrogel, a preservative, and/or a stabilizing agent, without limitation. These agents can provide a longer half-life of the ECM-derived nanovesicles in the composition. The composition can also include any additional therapeutic agent of interest, such as, but not limited to, a chemical compound, a nucleic acid molecule, a polypeptide, a growth factor, a cytokine, or a small molecule. In some embodiments, the therapeutic agent is a microRNA or a protein.

Pharmaceutical compositions can include a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms. The composition can be an injectable composition, either as liquid solutions or suspensions. The composition can also be a solid forms suitable for solution in, or suspension in, liquid. The composition can be a gel. These preparations also can be emulsified.

A typical composition includes a pharmaceutically acceptable carrier. For instance, the composition may contain less, than, equal to, or more than 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-fungal agents, anti-oxidants, chelating agents and inert gases. The pH and exact concentration of the various components the pharmaceutical composition are adjusted according to well-known parameters.

Formulations, such as for oral administration, can include typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In a certain embodiment, the composition can be an autologous composition or obtained from the same patient to be treated. Particularly, extracellular matrix from a subject, such as a human, can be harvested and used for the isolation of ECM-derived nanovesicles. The composition can be then administered in a pharmaceutical composition to the same donor (autologous). In another embodiment, the composition may be allogenic, such that the donor organism that provides ECM for the isolation of the ECM-derived nanovesicles, and recipient organism to be treated, are the same species but different individuals (allogenic). In an alternative embodiment, the composition can be xenogenic. Thus nanovesicles are derived from an ECM of a different species, prior to administration to the subject. For this purpose, the ECM is taken from a donor, for example an animal such as a pig, and nanovesicles are isolated from the ECM. The ECM-derived nanovesicles are then administered in a pharmaceutical composition to a subject of a different species. In one non-limiting example, the subject is a human.

There are also in vitro and ex vivo uses of the disclosed compositions. ECM-derived nanovesicles can be added to alter cell proliferation, migration and/or differentiation. In some embodiments, cell proliferation, migration and/or differentiation are induced. In other embodiments, cell proliferation, migration and/or differentiation are inhibited. The nanovesicles can be used with, or without, an extracellular matrix. In some embodiments the cell can be a stem cell, such as, but not limited to, a perivascular stem cell. In other embodiments, the cell can be a macrophage or a monocyte.

In some embodiments, a method is provided for altering cell proliferation, migration and/or differentiation on an extracellular matrix of interest. In certain embodiments, the methods include introducing isolated nanovesicles derived from a second extracellular matrix into the extracellular matrix of interest. The additional of the ECM-derived nanovesicles alters cell proliferation, migration and/or differentiation of cells grown on the ECM. In some embodiments the cell can be a stem cell, such as, but not limited to, a perivascular stem cell. In other embodiments, the cell can be a macrophage or a monocyte.

The extracellular matrix of interest and the ECM-derived nanovesicles can be autologous, allogeneic or xenogeneic. The extracellular matrix of interest and the ECM-derived nanovesicles can be from the same or different tissue. The extracellular matrix of interest and the ECM-derived nanovesicles can be from the same or different species. In specific non-limiting examples, the extracellular matrix of interest and/or the ECM-derived nanovesicles are human or porcine.

The cell can be any cell of interest. In some embodiments, the cell is a stem cell or a progenitor cell. In other embodiments, the cell is a macrophage, myoblast, a perivascular stem cell, or a neuroblastoma cell. The use of the disclosed ECM-derived nanovesicles on scaffolds and devices is disclosed below.

Methods for Treating Tumors

Methods are disclosed herein for reducing the proliferation of tumor cells, either in vivo or in vitro. Methods are also disclosed herein for increasing the apoptosis of tumor cells, either in vivo or in vitro. In addition, methods are disclosed herein for decreasing the migration of tumor cells, either in vivo or in vitro. These methods include contacting the tumor cells with an effective amount of the ECM-derived nanovesicles disclosed herein. In some embodiments, the tumor cells are glioma cells. In other embodiments, the ECM-derived nanovesicles are from urinary bladder. In further embodiments, the tumor cells are glioma cells and the ECM-derived nanovesicles are isolated from urinary bladder ECM. In further embodiments, the tumor cells are esophageal adenocarcinoma cells. In other embodiments, the ECM-derived nanovesicles are isolated from esophageal ECM. In further embodiments, the tumor cells are esophageal adenocarcinoma and the ECM-derived nanovesicles are isolated from esophageal ECM. ECM-derived nanovesicles can also be produced from tumor tissue. The ECM can be human, or from a veterinary subject.

All of the methods disclosed herein can be used for any type of glioma or glioma cell. The glioma can be an ependymoma, astrocytoma, oligodendroglioma, brainstem glioma, optic nerve glioma, or a mixed glioma. The glioma can be WHO grade I, II, III or IV. The glioma can be a low-grade glioma or a high-grade (WHO grade III-IV) glioma. The glioma can be supratentorial, infratentorial or pontine.

Methods are also provided for treating a tumor in a subject. In some embodiments, the methods include treating an existing tumor in a subject. In additional embodiments, methods are disclosed herein for preventing conversion of a benign to a malignant lesion, or preventing metastasis in a subject. In some non-limiting examples, the methods reduce a symptom of the tumor in the subject. In additional non-limiting examples, the tumor is a solid tumor. In some embodiments, the tumor cells are glioma cells. In other embodiments, the ECM-derived nanovesicles are isolated from urinary bladder ECM. In further embodiments, the tumor cells are glioma cells and the ECM-derived nanovesicles are isolated from urinary bladder ECM. In further embodiments, the tumor cells are esophageal adenocarcinoma cells. In other embodiments, the ECM-derived nanovesicles are isolated from esophageal ECM. In further embodiments, the tumor cells are esophageal adenocarcinoma and the ECM-derived nanovesicles are isolated from esophageal ECM.

Generally, the methods include selecting a subject having a tumor, such as a benign or malignant tumor, and administering to the subject a therapeutically effective amount of ECM-derived nanovesicles, as disclosed herein. In some embodiments, methods disclosed herein include selecting a subject in need of treatment, such as a subject with a glioma, and administering to the subject a therapeutically effective amount of the ECM-derived nanovesicles. Additional agents can also be administered to the subject of interest, such as, but not limited to, chemotherapeutic agents. Additional treatments can also be administered to the subject, such as, but not limited to, surgical resection of the tumor.

The tumor can be benign or malignant. The tumor can be a solid tumor or a lymphoproliferative tumor. The tumor can be any tumor of interest, including, but not limited to, glioma. In other embodiments, the tumor is a lymphoma, breast cancer, lung cancer or colon cancer. Additional examples are skin tumors, breast tumors, brain tumors, cervical carcinomas, testicular carcinomas, head and neck tumors, gastrointestinal tract tumors, genitourinary system tumors, gynecological system tumors, breast, endocrine system tumors, skin tumors, a sarcoma of the soft tissue and bone, a mesothelioma, a melanoma, a neoplasm of the central nervous system, or a leukemia. In some embodiments, the tumor is a head and neck tumor, such as tumors of the nasal cavity, paranasal sinuses, nasopharynx, oral cavity, oropharynx, larynx, hypopharynx, salivary glands and paragangliomas. In other embodiments, the tumor is a lung tumor, such as a non-small cell lung cancer or a small cell lung cancer. In further embodiments, the tumor can be a tumor of the gastrointestinal tract, such as cancer of the esophagus, stomach, pancreas, liver, biliary tree, small intestine, colon, rectum and anal region. In yet other embodiments, the tumor can be a tumor of the genitourinary system, such as cancer of the kidney, urethra, bladder, prostate, urethra, penis and testis. In some embodiments, the tumor is a gynecologic tumor, such as cancer of the cervix, vagina, vulva, uterine body, gestational trophoblastic diseases, ovarian, fallopian tube, peritoneal, or breast. In other embodiments, the tumor is an endocrine system tumor, such as a thyroid tumor, parathyroid tumor, adrenal cortex tumor, pancreatic endocrine tumor, carcinoid tumor and carcinoid syndrome. The tumor can be a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of tumors, rhabdomyosarcoma. The tumor can be a lymphoma, comprising non-Hodgkin's lymphomas, cutaneous T-cell lymphomas, primary central nervous system lymphoma, and Hodgkin's disease. The tumor can be a leukemia, such as acute leukemia, chronic myelogenous leukemia and lymphocytic leukemia. The tumor can be plasma cell neoplasms, a cancer of unknown primary site, a peritoneal carcinomastosis, a Kaposi's sarcoma, AIDS-associated lymphomas, AIDS-associated primary central nervous system lymphoma, AIDS-associated Hodgkin's disease and AIDS-associated anogenital cancers, a metastatic cancer to the liver, metastatic cancer to the bone, malignant pleural and pericardial effusions and malignant ascites. In specific non-liming examples, the tumor is melanoma or colon cancer.

Treatment of the tumor is generally initiated after the diagnosis of the tumor, or after the initiation of a precursor condition (such as dysplasia or development of a benign tumor). Treatment can be initiated at the early stages of cancer, for instance, can be initiated before a subject manifests symptoms of a condition, such as during a stage I diagnosis or at the time dysplasia is diagnosed. However, treatment can be initiated during any stage of the disease, such as but not limited to stage I, stage II, stage III and stage IV cancers. In some examples, treatment is administered to these subjects with a benign tumor that can convert into a malignant or even metastatic tumor.

The presence of a tumor can be determined by methods known in the art, and typically include cytological and morphological evaluation. The tumor can be an established tumor.

Treatment initiated after the development of a condition, such as malignant cancer, may result in decreasing the severity of the symptoms of one of the conditions, or completely removing the symptoms, or reducing metastasis, tumor volume or number of tumors. In some example, the tumor becomes undetectable following treatment. In one aspect of the disclosure, the formation of tumors, such as metastasis, is delayed, prevented or decreased. In another aspect, the size of the primary tumor is decreased. In a further aspect, a symptom of the tumor is decreased. In yet another aspect, tumor volume is decreased.

In some examples, the methods are for the treatment of a subject with a tumor. A therapeutically effective amount of the ECM-derived nanovesicles disclosed herein are administered to the subject. In specific non-limiting examples, the ECM-derived nanovesicles are isolated from a urinary bladder. In other non-limiting examples, the ECM-derived nanovesicles are isolated from an esophagus. In some embodiments the administration reduces tumor cell proliferation, increases tumor cell apoptosis and/or decreases tumor cell migration. The administration can be directly to the tumor. In specific non-limiting examples, the tumor is a glioma.

Treatment prior to the development of the condition, such as treatment upon detecting dysplasia or an early (benign) precursor condition, is referred to herein as treatment of a subject that is "at risk" of developing the condition. In some embodiments, administration of a composition, such as ECM-derived nanovesicles, or a pharmaceutical composition comprising the ECM-derived nanovesicles, can be performed during or after the occurrence of the conditions described herein. In some embodiments, the subject does not have Barrett's esophagus. In other embodiments, the subject has Barrett's esophagus.

Pharmaceutical compositions can include the ECM-derived nanovesicles, and optionally one or more additional chemotherapeutic agents. These compositions are of use for threating a tumor. These compositions can be formulated in a variety of ways for administration to a subject to affect the proliferation of cells in the tumor, or to delay, prevent, reduce the risk of developing, or treat, or reduce the incidence of metastasis, of any tumor of interest. The compositions described herein can also be formulated for application such that they prevent metastasis of an initial lesion. In some embodiments, the compositions are formulated for local administration, such as intratumoral administration. Pharmaceutical compositions are thus provided for both local use and for systemic use, formulated for use in human or veterinary medicine. In some embodiments, the composition can be administered by injection or catheter.

While the disclosed methods and compositions will typically be used to treat human subjects they may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen. In some embodiments, the subject is a human, and the ECM-derived nanovesicles are from human tissue.

In some embodiments, when locally administered into cells in an affected area or a tissue of interest, such as a tumor, the disclosed composition reduces tumor cell proliferation, increases tumor cell apoptosis and/or reduces tumor cell migration. The ECM-derived nanovesicles can be administered by any route, including parenteral administration, for example, intravenous, intraperitoneal, intramuscular, intraperitoneal, intrasternal, or intraarticular injection or infusion, or by sublingual, oral, topical, intranasal, or transmucosal administration, or by pulmonary inhalation. The appropriate route of administration can be selected by a physician based on the presentation of the tumor.

When the ECM-derived nanovesicles are provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, such as about 7.2 to about 7.4. Useful buffers include sodium citrate-citric acid and sodium phosphate-phosphoric acid, and sodium acetate-acetic acid buffers.

A form of repository or "depot" slow release preparation may be used so that therapeutically effective amounts of the preparation are delivered into the bloodstream over many hours or days following injection or delivery.

Suitable examples of sustained-release compositions include suitable polymeric materials (such as, for example, semi-permeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release formulations may be administered orally, rectally, parenterally, intracistemally, intravaginally, intraperitoneally, topically (as by powders, ointments, gels, drops or transdermal patch), bucally, or as an oral or nasal spray, depending on the location of the tumor. The pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

The pharmaceutically acceptable carriers and excipients useful in the disclosed methods are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved. Administration may begin whenever the suppression or prevention of disease is desired, for example, at a certain age of a subject, or prior to an environmental exposure.

The exact dose is readily determined by one of skill in the art based on the potency of the specific fraction, the age, weight, sex and physiological condition of the subject. Suitable concentrations include, but are not limited to, about 1 ng/ml-100 gr/ml.

Additional agents can be administered, such as a cytokine, a chemokine, or a chemotherapeutic agent. These can be included in the disclosed pharmaceutical compositions. A cytokine can be administered, such an interleukin (IL) or an interferon, such as interferon (IFN) $\alpha$, $\beta$ or $\gamma$, IL-1, IL-6 and IL-10. In one example, for the prevention and treatment of tumors, surgical treatment can be administered to the subject. In one example, this administration is sequential. In other examples, this administration is simultaneous.

Examples of chemotherapeutic agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Methods for Increasing M2 Macrophages

Macrophages have been shown to be critical regulators of normal healing following injury, and in normal tissue development. The disclosed nanovesicles can recapitulate the effects of whole ECM on macrophage phenotype, leading to an increase in M2-like, regulatory, or pro-remodeling macrophages. Thus, any of the compositions disclosed herein can be used for modifying macrophage phenotype, such as for inducing regulatory M2 macrophages.

In some embodiments, methods are disclosed for inducing M2 macrophages in a subject by administering a therapeutically effective amount of a composition including the ECM-derived nanovesicles, as disclosed herein, thereby inducing M2 macrophages in the subject. In further embodiments, methods are disclosed for decreasing M1 (proinflammatory) macrophages in a subject. The methods include administering a therapeutically effective amount of a composition including the ECM-derived nanovesicles, as disclosed herein, thereby inhibiting the M1 macrophages in the subject. The subject can be any subject of interest, such as a subject with inflammation or a wound. In some non-limiting examples, the subject has an inflammatory disorder, such as, but not limited to, ulcerative colitis or rheumatoid arthritis. In other non-limiting examples, the subject is an organ transplant recipient, a subject with graft versus host disease, a subject with myocardial infarction, or a subject with a wound, such as, but not limited to, a subject with a surgical wound or a non-surgical traumatic wound. Thus, disclosed in a method for accelerating wound healing in an individual in need thereof, comprising administering a therapeutically effective amount of a composition including the ECM-derived nanovesicles, as disclosed herein. The administration can be local, such as to the site of the wound or graft.

Methods are provided for promoting the healing of anastomotic and other wounds caused by surgical procedures in individuals. These methods include administration of an effective amount of a composition including the ECM-derived nanovesicles, as disclosed herein to an individual before, after, and/or during anastomotic or other surgery. Anastomosis is the connecting of two tubular structures, for example, when a mid-section of intestine is removed and the remaining portions are linked together to reconstitute the intestinal tract. Unlike cutaneous healing, the healing process of anastomotic wounds is generally obscured from view. Further, wound healing, at least in the gastrointestinal tract, occurs rapidly in the absence of complications; however, complications often require correction by additional surgery. Thornton, F. and Barbul, A., Surg. Clin. North Am. 77:549 573 (1997).

Methods are also provided for stimulating healing of wounds including surgical wounds, excisional wounds, deep wounds involving damage of the dermis and epidermis, eye tissue wounds, dental tissue wounds, oral cavity wounds, diabetic ulcers, dermal ulcers, *cubitus* ulcers, arterial ulcers, venous stasis ulcers, and burns resulting from heat exposure or chemicals. Methods are also provided for wounds that result from ischemia and ischemic injury, such as chronic venous leg ulcers caused by an impairment of venous circulatory system return and/or insufficiency. A therapeutically effective amount of a composition including the ECM-derived nanovesicles, as disclosed herein can be used to promote dermal reestablishment subsequent to dermal loss. In addition, a therapeutically effective amount of a composition including the ECM-derived nanovesicles, as disclosed herein can be used to increase the tensile strength of epidermis and epidermal thickness. Thus, the disclosed methods are of use in stimulating the healing of different types of wounds in normal subjects and subjects that have impaired wound healing.

Methods are also provided herein to increase the adherence of skin grafts to a wound bed and to stimulate re-epithelialization from the wound bed. Types of grafts include, but are not limited to: autologous skin graft, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The methods include administering to the subject with the graft a therapeutically effective amount of a composition including the ECM-derived nanovesicles, as disclosed herein, thereby increasing the adherence and acceptance of the graft.

Methods are also provided to treat blisters and burns due to abrasion or chemical injury. These methods include the treatment of the skin or internal organs. These methods include treatment of ovary injury, for example, due to treatment with chemotherapeutics or treatment with cyclophosphamide; radiation- or chemotherapy-induced cystitis; or high-dose chemotherapy-induced intestinal injury. The methods include administering to the subject a therapeutically effective amount of a composition including the ECM-derived nanovesicles, as disclosed herein, to promote healing of the blisters or burns.

For treatment of the skin, a therapeutically effective amount of a composition including the ECM-derived nanovesicles, as disclosed herein can be locally administered to the affected area of the skin, such as in the form of an ointment. In one embodiment, the ointment is an entirely homogenous semi-solid external agent with a firmness appropriate for easy application to the skin. Such an ointment can include fats, fatty oils, lanoline, Vaseline, paraffin, wax, hard ointments, resins, plastics, glycols, higher alcohols, glycerol, water or emulsifier and a suspending agent. Using these ingredients as a base, a decoy compound can be evenly mixed. Depending on the base, the mixture can be in the form of an oleaginous ointment, an emulsified ointment, or a water-soluble ointment oleaginous ointments use bases such as plant and animal oils and fats, wax, VASELINE® and liquid paraffin. Emulsified ointments are comprised of an oleaginous substance and water, emulsified with an emulsifier. They can take either an oil-in-water form (O/W) or a water-in-oil-form (W/O). The oil-in-water form (O/W) can be a hydrophilic ointment. The water-in-oil form (W/O) initially lacks an aqueous phase and can include hydrophilic Vaseline and purified lanoline, or it can contain a water-absorption ointment (including an aqueous phase) and hydrated lanoline. A water-soluble ointment can contain a completely water-soluble Macrogol base as its main ingredient.

Pharmaceutically acceptable carriers include a petroleum jelly, such as VASELINE®, wherein the petroleum jelly contains 5% stearyl alcohol, or petroleum jelly alone, or petroleum jelly containing liquid paraffin. Such carriers enable pharmaceutical compositions to be prescribed in forms appropriate for consumption, such as tablets, pills, sugar-coated agents, capsules, liquid preparations, gels, ointments, syrups, slurries, and suspensions. When locally administered into cells in an affected area or a tissue of interest, the composition including the ECM-derived nanovesicles can be administered in a composition that contains a synthetic or natural hydrophilic polymer as the carrier. Examples of such polymers include hydroxypropyl cellulose and polyethylene glycol. A composition including the ECM-derived nanovesicles can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used. A therapeutically effective amount of a composition including the ECM-derived nanovesicles, as disclosed herein can also be incorporated into bandages and dressings for wounds.

Scaffolds and Devices

Devices are also disclosed that include nanovesicles derived from an extracellular matrix, such as a mammalian extracellular matrix, for example a human or a porcine extracellular matrix. Any of the ECM-derived nanovesicles, as disclosed herein, can be coated on, or imbedded in, components of a device. The device can be, without limitation, a surgical mesh, a stent, a pacemaker, a catheter, heart valve, biosensor, a drug delivery device, or an orthopedic implant. The device can be used to repair a damaged or torn tendon or muscle. The scaffold or device can be for the treatment of a temporomandibular joint disorder, see for example, see U.S. Pat. No. 9,277,999, incorporated herein by reference.

Bioscaffolds are disclosed herein that include nanovesicles derived from an extracellular matrix, such as a mammalian extracellular matrix, for example a human or a porcine extracellular matrix. Any of the ECM-derived nanovesicles, as disclosed herein, can be included in a bioscaffold, which is a biologically compatible scaffold. These bioscaffolds can be incorporated into a device.

The polymeric components used to make the devices disclosed herein are preferably biocompatible. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the polymer can sustain a population of cells and/or the polymer composition, device, and degradation products, thereof are not cytotoxic and/or carcinogenic for wild-type (normal, non-cancerous) cells within useful, practical and/or acceptable tolerances. For example, the polymer when placed in a human epithelial cell culture does not adversely affect the viability, growth, adhesion, and number of cells. In one non-limiting embodiment, the compositions, and/or devices are "biocompatible" to the extent they are acceptable for use in a human patient according to applicable regulatory standards in a given jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues from the implanted scaffold.

Scaffolds and devices can be used for a large number of medical applications including, but not limited to, wound healing, tissue remodeling, and tissue regeneration. For example and without limitation, the scaffold can be used for wound healing.

In some embodiments, the device or bioscaffold can include an extracellular matrix. In specific non-limiting examples, the extracellular matrix is from esophageal cells, urinary bladder cells, a small intestinal submucosa, or a dermis.

In a certain embodiment, the ECM can be autologous, so that the ECM and the ECM-derived nanovesicles are from the same subject. Particularly, an ECM from a subject, such as a human, can be harvested and used for the isolation of nanovesicles. These ECM-derived nanovesicles can be used with ECM from the same subject. Thus, a bioscaffold or device is produced containing the ECM and the ECM-derived nanovesicles from the same subject.

In another embodiment, the ECM can be allogenieic, so that the ECM and the ECM-derived nanovesicles are from the different subjects of the same species. Particularly, an ECM from a subject, such as a human, can be harvested and used for the isolation of nanovesicles. These ECM-derived nanovesicles can be used with ECM from a different subject. Thus, a bioscaffold or device is produced containing the ECM and the ECM-derived nanovesicles from the different subjects, but of the same species.

In another embodiment, the ECM can be xenogenic, so that the ECM and the ECM-derived nanovesicles are from the different species. In one non-limiting example, an ECM from a subject, such as a human, can be harvested and used for the isolation of nanovesicles. These ECM-derived nanovesicles can be used with ECM from a different species, such as a pig. In another non-limiting example, an ECM from a subject, such as a pig, can be harvested and used for the isolation of nanovesicles. These ECM-derived nanovesicles can be used with ECM from a different species, such as a human. Thus, a bioscaffold or device is produced containing the ECM and the ECM-derived nanovesicles from the different species.

In a further embodiment, the ECM and the ECM-derived nanovesicles are from the same tissue source. In another embodiment, the ECM and ECM-derived nanovesicles are from different tissue sources. Thus, in some non-limiting examples, both the ECM and the ECM-derived nanovesicles can be produced from esophageal tissue, urinary bladder, small intestinal submucosa, dermis, umbilical cord, pericardium, cardiac tissue, or skeletal muscle, or cells in culture from these tissues. In other non-limiting examples, the ECM-derived nanovesicles are produced from esophageal tissue, urinary bladder, small intestinal submucosa, dermis, umbilical cord, pericardium, cardiac tissue, or skeletal muscle cells, and the ECM is not from this tissue source. In further non-limiting examples, the ECM-is produced from esophageal tissue, urinary bladder, small intestinal submucosa, dermis, umbilical cord, pericardium, cardiac tissue, or skeletal muscle, and the ECM-derived nanovesicles are not from this tissue source.

In one non-limiting embodiment, in addition to ECM-derived nanovesicles, the scaffold (or device) includes other agents, such as bioactive agents. These bioactive agents can be used to facilitate tissue healing, tissue remodeling and/or angiogenesis. In another non-limiting embodiment, the scaffold (or device) includes additional bioactive agents to ward off bacteria and other pathogens, recruit selected cell types, such as stem cells, or induce differentiation of cells. In yet another non-limiting embodiment, the scaffold comprises pores to allow a wound to drain or for cells to pass through and deposit connective tissue.

As noted above, a scaffold or device can include an ECM, in addition to the ECM-derived nanovesicles. In another non-limiting embodiment, combinations of cells and bioactive agents are added to the scaffold or device that includes the ECM-derived nanovesicles before or during implantation at a site in a patient. The disclosed nanovesicles can be applied to, or incorporated into, any of these scaffolds.

A scaffold can include any suitable synthetic polymeric components, biological polymeric components, or combinations thereof. "Biological polymer(s)" are polymers that can be obtained from biological sources, such as, without limitation, mammalian or vertebrate tissue, and extracellular matrix. Biological polymers can be modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, a non-woven mesh formed by electrodeposition.

In some embodiments, the polymeric components suitable for the scaffold can be a polymer that is biodegradable and biocompatible. By "biodegradable", it is meant that a polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage. In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. Non-limiting examples of biodegradeable polymers include poly(ester urethane) urea elastomers (PEUU) and poly(ether ester urethane) urea elastomers (PEEUU). In other non-limiting embodiments, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold. Alternatively, the polymer(s) may contain peptides or biomacromolecules as building blocks which are susceptible to chemical reactions once placed in situ. In one non-limiting example, the polymer is a polypeptide comprising the amino acid sequence alanine-alanine-lysine, which confers enzymatic lability to the polymer. In another non-limiting embodiment, the polymer composition may comprise a biomacromolecular component derived from an ECM. For example, the polymer composition may comprise the biomacromolecule collagen so that collagenase, which is present in situ, can degrade the collagen.

The polymer components may be selected so that they degrade in situ on a timescale that is similar to an expected rate of healing of the wound or tissue. Non-limiting examples of in situ degradation rates include between one week and one year or increments there between for instance, between two weeks and 10 months, and between one month and six month.

The mechanical properties of a biodegradable scaffold can be optimized to operate under the normal strain and stress on the native tissue at the site of implantation. In certain non-limiting embodiments, the mechanical properties of the scaffold are optimized similar to or identical to that of native soft tissue, such as fascia, connective tissue, bone, cartilage, blood vessel, muscle, tendon, fat, etc.

The mechanical properties of the scaffold also may be optimized to be suitable for surgical handling. In one non-limiting embodiment, the scaffold is flexible and can be sutured to the site. In another, the scaffold is foldable and can be delivered to the site by minimally invasive laparoscopic methods.

The physical and/or mechanical properties of the biodegradable scaffold can be optimized according to the intended use. Variables that can be optimized include without limitation, the extent of physical, chemical or photo-oxidative cross-linking in a network comprising polymeric components, the ratio of polymeric components within the network, the distribution of molecular weight of the polymeric components, and the method of processing the polymers. Polymers are typically semicrystalline and their physical properties and/or morphology are dependent upon a large number of factors, including monomer composition, polydispersity, average molecular weight, cross-linking, and melting/crystallization conditions. For example, flow and/or shear conditions during cooling of a polymer melt are known to affect formation of crystalline structures in the composition. In one non-limiting embodiment, the scaffold comprises a polymeric component that provides strength and durability to the scaffold, yet is elastomeric so that the mechanical properties of the scaffold are similar to the native tissue surrounding the wound or site in need of tissue regeneration.

As described herein, according to certain non-limiting embodiments, one or more of the polymeric components of the biodegradable scaffold is elastomeric. In one non-limiting example, the scaffold has physical properties similar to that of cartilage. In certain non-limiting embodiments, the biodegradable scaffold comprises highly distensible polymeric components. Examples of suitable polymers include those that have a breaking strain ranging from about 100% to about 900%, including any increments there between, for example between 200% and 800%, or between 325% and 600%. In other non-limiting embodiments, the breaking strain of the polymer is between 50% and 100% including any increments there between. Further, it is often useful to select polymers with tensile strengths of from 10 kPa to 30 MPa, including increments there between, such as from 5 MPa to 25 MPa, and between 8 MPa and 20 MPa. In certain non-limiting embodiments, the initial modulus is between 10 kPa to 100 MPa and increments there between, such as between 10 MPa and 90 MPa, and between 20 MPa and 70 MPa.

The disclosure is illustrated by the following non-limiting Examples.

EXAMPLES

Example 1

Materials and Methods

Chemicals and Reagents. Pepsin from Porcine Stomach Mucosa was obtained from MP Biomedical (Solon, OH). Collagenase, from *Clostridium histolyticum* was obtained from Sigma Aldrich (St. Louis, MO). Proteinase K solution, Quant-iT PicoGreen dsDNA Assay kit and RNase A were obtained from Thermo Scientific (Waltham, MA). RNase-free DNase was obtained from Qiagen (Valencia, CA).
ECM Bioscaffold Production.

Dermal ECM. Dermal ECM was prepared as previously described. Briefly, full thickness skin was harvested from market weight (~110 kg) pigs (Tissue Source, Inc., Lafayette, IN) and the subcutaneous fat and epidermis were removed by mechanical delamination followed by treatment with 0.25% trypsin (Thermo Fisher Scientific, Waltham, MA) for 6 h, 70% ethanol for 10 h, 3% $H_2O_2$ for 15 min, 1% Triton X-100 (Sigma-Aldrich, St. Louis, MO) in 0.26% EDTA/0.69% Tris for 6 h with a solution change for an additional 16 h, 0.1% peracetic acid/4% ethanol (Rochester Midland, Rochester, NY) for 2 h. Water washes were performed between each chemical change with alternating water and phosphate buffered saline (PBS) washes following the final step. All chemical exposures were conducted under agitation on an orbital shaker at 300 rpm. Dermal ECM was then lyophilized and milled into particulate form using a Wiley Mill with a #40 mesh screen.

Urinary Bladder Matrix (UBM). UBM was prepared as previously described (Wolf et al., Biomaterials 2012 October; 33(29):7028-38). Porcine urinary bladders from market weight animals were acquired from Tissue Source, LLC. (Lafayette, Indiana). Briefly, the tunica serosa, tunica muscularis externa, tunica submucosa, and tunica muscularis mucosa were mechanically removed. The luminal urothelial cells of the tunica mucosa were dissociated from the basement membrane by washing with deionized (DI) water. The remaining tissue consisted of basement membrane and subjacent lamina propria of the tunica mucosa, and was decellularized by agitation in 0.1% peracetic acid with 4% ethanol for 2 hours at 300 rpm. The tissue was then extensively rinsed with phosphate-buffered saline (PBS) and sterile water. The UBM was then lyophilized and milled into particulate form using a Wiley Mill with a #60 mesh screen.

Small Intestinal Submucosa (SIS). Preparation of SIS bioscaffold has been previously described. Briefly, jejunum was harvested from 6-month-old market weight (240-260 lbs) pigs and split longitudinally. The superficial layers of the tunica mucosa were mechanically removed. Likewise, the tunica serosa and tunica muscularis externa were mechanically removed, leaving the tunica submucosa and basilar portions of the tunica mucosa. Decellularization and disinfection of the tissue were completed by agitation in 0.1% peracetic acid with 4% ethanol for 2 hours at 300 rpm. The tissue was then extensively rinsed with phosphate-buffered saline (PBS) and sterile water. The SIS was then lyophilized and milled into particulate form using a Wiley Mill with a #60 mesh screen.

BARD XENMATRIX™ (porcine Dermis), ACELL®MATRISTEM® (porcine UBM) and COOK®

BIOTECH, BIODESIGN® (porcine SIS) were provided by the manufacturers of the respective devices.

Enzymatic digestion of ECM samples. ECM samples were lyophilized to dryness, manually cut into small pieces and ground into a powder using a Wiley Mill with a #60 mesh screen. Enzymatic digestion was performed by digesting 5 mg/ml dry weight of each sample with either 0.1 mg/ml proteinase K in buffer (50 mM Tris-HCl, pH8, 200 mM NaCl) for 24 h at room temperature; 0.1 mg/ml Collagenase in buffer (50 mM Tris pH8, 5 mM $CaCl_2$), 200 mM NaCl) for 24 h at room temperature; or 1 mg/ml pepsin in buffer (0.01M HCl) for 24 h at room temperature. Prior to nucleic acid extraction, pepsin solubilized samples were neutralized to a pH of 8.0 with NaOH. Undigested samples (control) were prepared by resuspension of 5 mg/ml dry weight of each sample in salt buffer (50 mM Tris-HCl, pH8, 200 mM NaCl) or acid buffer (0.01M HCl), without enzyme treatment.

Nucleic acid extraction and profiling. Nucleic acid was extracted from ECM powder samples by the addition of an equal volume of phenol:chloroform, pH8. Samples were briefly vortexed, centrifuged at 12,000×g for 10 minutes, and the aqueous phase transferred to a new tube. Nucleic acid was precipitated by the addition of $\frac{1}{10}^{th}$ volume 3M Sodium Acetate and 3 volumes 100% ethanol, mixed by inversion and centrifuged for 20 minutes at 20,000×g, 4° C. Nucleic acid pellets were washed once with 75% ethanol, and re-suspended in nuclease-free water. The basepair length of recovered nucleic acid was analyzed using the Agilent 2100 Bioanalyzer (Agilent Technologies), or by electrophoresis in 2% (wt/vol) agarose gels and ethidium bromide staining. Quantitation of total nucleic acid was performed by UV absorbance at 260 nm using the Thermo Scientific NanoDrop 1000 Spectrophotometer. Quantitation of dsDNA was performed using the Quant-iT PicoGreen dsDNA Assay kit according to the manufacturers recommended protocol.

RNA isolation. Cellular RNA as well as ECM "free RNA" (entrapped within the ECM bioscaffolds as a consequence of the decellularization process) was isolated using the miRNeasy Mini kit (Qiagen, Valencia, CA) according to the manufacturer's instructions. Nanovesicle RNA was isolated via SeraMir kti (SBI, Mountain View, CA) according to the manufacturer's instructions. Prior to nanovesicle RNA isolation samples were treated with 2 unites (10 ug/mL) of RNase (ABI, Foster City, CA) at 37 degrees for 30 minutes to degrade any contaminating RNA such as remnant RNA ("free RNA") from the decellularization process. Reaction was terminated by the addition of RNase inhibitor (ABI, Foster City, CA). RNA quantity was determined using Nanodrop spectrophotometer (NanoDrop, Wilmington, DE) and its quality determined via Agilent Bioanalyzer 2100 (Agilent Technologies, Santa Clara, CA).

Nanovesicle isolation. Digest was subjected to successive centrifugations at 500 g (10 min), 2,500 g (20 min) and 10,000 g (30 min), to remove collagen fibril remnants. Each of the above centrifugation steps was preformed three times. The fiber-free supernatant was then centrifuged at 100,000 g (Beckman Coulter Optima L-90K ultracentrifuge) at 4° C. for 70 min. The 100,000 g pellets were washed and suspended in 500 μl of PBS. The above procedure was done on digest enzyme with no ECM to serve as a control.

Nanovesicle imaging. Transmission electron microscopy (TEM) imaging was conducted on ECM vesicles loaded on carbon-coated grids and fixed in 4% paraformaldehyde. Grids were imaged at 80 kV with a JEOL 1210 transmission electron microscope with high-resolution AMT digital camera. Size of MVs was determined from representative images using JEOL TEM software.

Gel electrophoresis and Western blotting. Nanovesicle protein concentration was determined using Pierce's bicinchoninic acid protein quantitation assay kit (Pierce Chemical, Rockford, IL) and resuspended in lamellae buffer (R&D Systems, Minneapolis, MN) containing 5% B-mercaptoethanol (Sigma, St. Louis, MO). Equal concentrations of the proteins were then loaded in wells of 5%-15% gradient SDS-PAGE (Bio-Rad, Hercules, CA). The gels were run using Mini-Protean electrophoresis module assembly (Bio-Rad) at 150 mV in running buffer (25 mM Tris base, 192 mM glycine, and 0.1% SDS) in double-distilled water, followed by semi dry transfer to polyvinylidene difluoride membranes (Millipore, Bedford, MA) for 45 min at 280 mA in transfer buffer (25 mM Tris, pH 7.5, 192 mM glycine, 20% methanol, and 0.025% sodium dodecyl sulfate). The membranes were then blocked for 45 min with Pierce protein-free blocking buffer (Pierce Chemical, Rockford, IL) and incubated overnight with the following primary antibodies: CD63 and CD81 (SBI, Mountain View, CA). Membranes were washed three times for 15 min each before and after they were incubated with appropriate secondary antibody. The washed membranes were exposed to chemiluminescent substrate (Bio-Rad) and then visualized using chemidoc touch instrument (Bio-Rad).

Nanovesicle size determination. Nanovesicles were diluted in particle-free PBS and their size determined using Nanoparticle Tracking Analysis (NTA) as described (Webber, J. & Clayton, A. How pure are your vesicles?). Briefly, NTA measurements were performed by using a NanoSight LM10 instrument (NanoSight NTA 2.3 Nanoparticle Tracking and Analysis Release Version Build 0025). Size distribution of Nanovesicles were analyzed by measuring the rate of Brownian motion with a NanoSight LM10 system (Nano-Sight, Wiltshire, United Kingdom) equipped with fast video capture and particle-tracking software. Nanovesicles were diluted in particle-free PBS and injected into a NanoSight sample cubicle. The mean±standard error (SD) size distribution was determined.

RNA sequencing. Small RNA libraries were prepared using Ion Total RNA Seq Kit v 2 and according to manufacturer's instructions. Briefly, following bead based size selection of RNA in the 10-200 nt range, cDNA was created by hybridization and ligation of indexed sequencing adapters followed by reverse transcription and PCR. Amplified library was again size selected using a bead based method and run on a bioanalyzer to verify library size distribution was as expected. The Ion One Touch 2 System was used to perform automated emulsion PCR of the prepared libraries and templated Ion Sphere™ Particle (ISP) enrichment. Sequencing was performed on an Ion Proton using a single PI sequencing chip. Quality filters were removed so that all sequence data would be reported. Sequences were analyzed for quality control (FASTQC) and aligned to the Human genome (HG19) using the Torrent Suite. Output files (.bam) were uploaded, mapped to miRBase V.20 and further analyzed using CLC Genomic (Qiagen, Valencia, CA)). Reads were normalized to reads per million reads (RPM).

Ingenuity pathway analysis. miRNAs identified via RNA sequencing were analyzed by Ingenuity Pathway Analysis (IPA) to determine a miRNA signaling pathway signature.

qPCR. Sybr Green gene expression assays (ABI, Foster City, CA) were used to determine the relative expression levels of iNOS, TNFa, STAT1, STAT2, STAT5A, STAT5B, IRF3, IRF4, IRF5, IL1RN, CD206, TGM2, STAT3, STAT6, KLF4, PPARg. Results were analyzed by the ΔΔCt method using β-glucuronidase (β-GUS) control to normalize the results. Fold change was calculated using nanovesicles control as the baseline.

Cell culture. Perivascular stem cells (PVSC) were isolated as previously described (Timothy et al., Biomaterials. 2013 September; 34(28): 6729-6737). Isolated cells were cultured in high-glucose Dulbecco's modified Eagle's medium (DMEM, Invitrogen) containing 20% fetal bovine serum (FBS, Thermo fisher), 100 U/mL penicillin, and 100 ug/mL streptomycin (Sigma Aldrich) at 37° C. in 5% CO2.

C2Cl2 muscle myoblast cells were obtained from the American Type Culture Collection (ATCC, Manassas, VA) and cultured following ATCC guidelines, in DMEM (Invitrogen) supplemented with 10% FBS and 1% penicillin/streptomycin (Sigma Aldrich) THP-1 human monocytes were obtained from ATCC and maintained in RPMI, 10% FBS, 1% penicillin/streptomycin and 0.05 mM B-mercaptoethanol in a humidified atmosphere at 37° C. with 5% CO2. Two million THP-1 cells per well were plated with 320 nM phorbol 12-myristate 13-acetate (PMA) for 24 hours to induce differentiation into macrophages. Adherent macrophages were washed in PBS and placed in fresh media, followed by 72 hour incubation in fresh media to rest. THP1 macrophages differentiated with PMA and rested have been shown to exhibit nearly indistinguishable activity from human peripheral blood macrophages (Diagneault et al., PLOS One 2010 Jan. 13; 5(1): e8668). Murine bone marrow derived macrophages (BMDM) were isolated and characterized as previously described (Sicari et al., Biomaterials 2014 October; 35(30):8605-12). Briefly, bone marrow was harvested from 6-8-week old C57bl/6 mice. Using aseptic technique, the skin from the proximal hind limb to the foot was removed, the tarsus and stifle disarticulated and the tibia isolated. Similarly, the coxafemoral joint was disarticulated for isolation of the femur. Bones will be kept on ice and rinsed in a sterile dish containing macrophage complete medium consisting of DMEM, 10% fetal bovine serum (FBS), 10% L929 supernatant, 0.1% beta-mercaptoethanol, 10 mm non-essential amino acids, and 10 mm hepes buffer. The ends of each bone were then transected and the marrow cavity flushed with complete medium using a 30-gauge needle. Harvested cells were washed and plated at 106 cell/ml, and allowed to differentiate into macrophages for 7 days with complete media changes every 48 h. NIE-115 cells, a mouse neuroblastoma cell line, were grown in Dulbecco's modified Eagle's medium (DMEM) supplemented with heat-inactivated 10% fetal bovine serum. One million cells were plated in a 6 well plate before addition of nanovesicles.

Nanovesicles fluorescence labeling. Nanovesicles were labeled using Exo-glow (SBI, Mountain View, CA) according to the manufacture instruction. Briefly, 500 µL of resuspended nanovesicles were labeled with Exo-glow and incubate in 37° C. for 10 minutes. 100 µl ExoQuick-TC were added to stop the reaction and samples were placed on ice for 30 minutes. Samples were then centrifuged for 10 minutes at 14,000. Supernatant was removed and pellet was resuspended with 500 µl of 1×PBS. In-vitro cells were then exposed to labeled nanovesicles for four hours and imaged via Axio Observer Z1 microscope.

In-vitro scratch assay. Cells were cultured as described above in six-well plates. When culture was confluent (24 h post seeding) nanovesicles were added to the culture media. A p-200 pipette tip was used to score two vertical lines through the confluent cell layer simulating a "wound". Images were acquired every 20 minutes by Axio Observer Z1 microscope.

Migration assay. Nanovesicles ability to effect cell function was evaluated via 8 mm CytoSelect cell migration assay (Cell Biolabs, San Diego, CA) upon perivascular stem cells (PVSC). PVSC were starved and treated with nanovesicles for 14-17 h in media with no added growth factors containing 0.5% heat inactivated FCS. Starved cells were harvested with trypsin, resuspended in serum-free media at a concentration of 4105 cells=mL, and preincubated for 1 h in a humidified 95% air=5% CO2 37 C incubator. The 96-well membrane chamber insert was placed onto the feeder tray, and 100 uL of cell suspension was added to each well of the membrane chamber, for a final concentration of 40,000 cells per well. The plate was covered and incubated for 4 h at 37 C under a humidified atmosphere in 95% air=5% CO2. One hundred and fifty microliters of cell detachment solution was added to each well of a clean harvesting tray. The 96-well membrane chamber was separated from the feeder tray, remaining cells on the topside of the membrane chamber were removed by aspiration, and the membrane chamber was placed onto the harvesting tray containing cell detachment solution and incubated in a cell culture incubator for 1 h, rinsing any cells from the bottom of the membranes into the harvesting tray wells. CyQuant GR Dye=cell lysis solution was prepared by diluting the dye in lysis buffer (1:75), the membrane chamber was removed from the harvesting tray, and 50 mL of dye=cell lysis solution was added to each well of the harvesting tray. The tray was incubated at room temperature for 20 min in order to lyse the cells and stain the nucleic acids. One hundred and fifty microliters of the contents of each well was then transferred to a plate suitable for fluorescence measurement. Fluorescence was measured with a SpectraMax M2 Plate Reader (Molecular Devices, Sunnyvale, CA) at 480-520 nm. Each experimental condition was tested in triplicate, and the average number of migrated cells was determined for each condition. Two paired t-test was used to detect significant differences between nanovesicles treated cells and control. P-values<*0.05 were considered significant Macrophage immunolabeling. ECM degradation products have shown to effect macrophage phenotype. Macrophage immunolabeling was preformed to evaluate if ECM embedded microvesicles have a similar effect upon macrophage phenotype. Primary mouse bone marrow derived macrophages (BMDM) were isolated and two markers (iNOS and Fizz-1) that are strong indicators of the pro-inflammatory "M1-like" and anti-inflammatory "M2-like" (respectively) phenotypes were used. The primary antibodies used for immunofluorescent staining were: (1) monoclonal anti-F4/80 (Abcam, Cambridge, MA) at 1:200 dilution for a pan-macrophage marker, (2) polyclonal anti-iNOS (Abcam, Cambridge, MA) at 1:100 dilution for an M1 marker, and (3) polyclonal anti-Fizz1 (Peprotech, Rocky Hill, NJ) for an M2 marker. Cells were incubated in blocking solution consisting of PBS, 0.1% Triton-X, 0.1% Tween-20, 4% goat serum, and 2% bovine serum albumin to prevent non-specific binding for 1 h at room temperature. Blocking solution was removed and cells were incubated in primary antibodies for 16 h at 4° C. After washing in PBS, cells were incubated in fluorophore-conjugated secondary antibodies (Alexa Fluor donkey anti-rat 488 or donkey anti-rabbit 488, Invitrogen, Carlsbad, CA) for 1 h at room temperature. After washing again with PBS, nuclei were counterstained with 4'6-diamidino-2-phenylindole (DAPI) prior to imaging. Images of three 20× fields were taken for each well using a live-cell microscope. Light exposure times for ECM-treated macrophages were standardized based upon those set for cytokine-treated macrophages, which served as a control. Images were quantified using a CellProfiler pipeline for positive F4/80, iNOS, and Fizz-1 percentages.

Example 2

Quantitation of Nucleic Acids in ECM Bioscaffold Materials

Figure 1B:
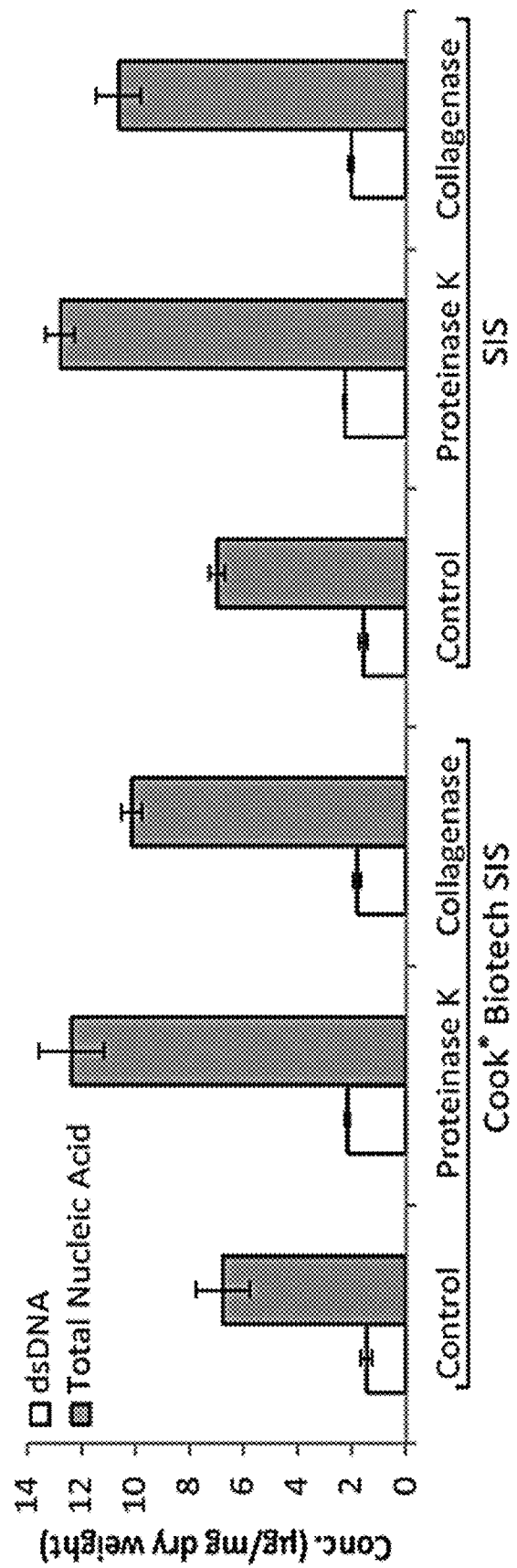
Figure 1C:
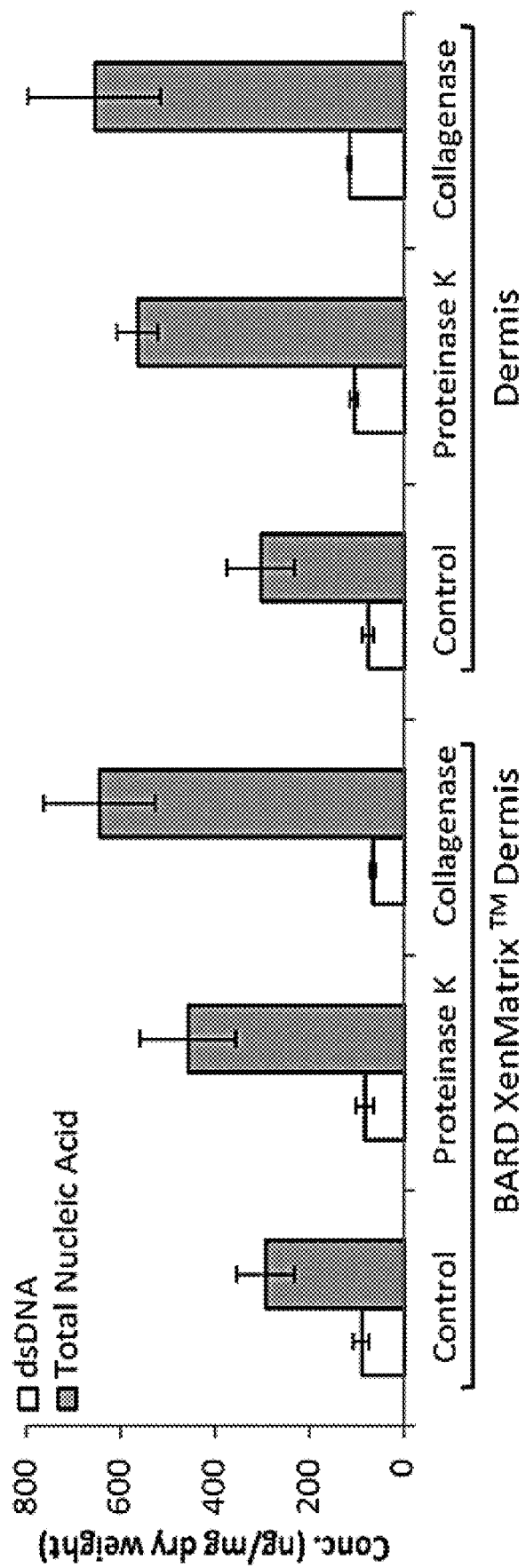

The discovery of ECM-nanovesicles was an unexpected result of studies to evaluate bioscaffolds for the presence of alternate forms of nucleic acid as a remnant of the decellularization process. Although the quantitation of double stranded DNA (dsDNA) is commonly used as a metric to assess decellularization efficiency, the quantitation of other forms of nucleic acid, such as RNA or single stranded DNA (ssDNA) is neglected in these analyses. To determine if alternative forms of nucleic acid were present in ECM bioscaffolds, nucleic acid was extracted from comminuted (acellular) ECM-scaffold materials using the phenol:chloroform method. Quantitation of dsDNA was performed using the PicoGreen assay, and quantitation of total nucleic acid was performed by UV absorbance at 260 nm, which detects all forms of nucleic acid present, including RNA. The results showed that the amount of dsDNA represented only a fraction of the total nucleic acid present in decellularized ECM-scaffold materials (FIG. 1). Surprisingly, it was observed that if these ECM-scaffolds were first enzymatically digested with various proteases prior to nucleic acid extraction, the amount of total nucleic acid significantly increased compared to undigested (control) samples. Importantly, this increase in total nucleic acid was not due to an increase in dsDNA, implying that alternate forms of nucleic acid were somehow encapsulated within and protected by the ECM. This pattern was observed for all forms of ECM-scaffold materials tested which included laboratory produced and commercially available equivalents of urinary bladder matrix (UBM) and ACELL® MATRISTEM™ (FIG. 1A); small intestinal submucosa (SIS) and SIS manufactured by COOK BIOTECH® (FIG. 1B); dermis and Bard® XENMATRIX™ (FIG. 1C). Additionally, nucleic acid concentrations between laboratory produced scaffolds and their commercially available equivalents were similar, thereby demonstrating that these results were not an artifact of our standard laboratory decellularization protocols.

Example 3

Enzymatic Digestion of Biologic Scaffolds Releases Small RNA Molecules

Figure 2B:
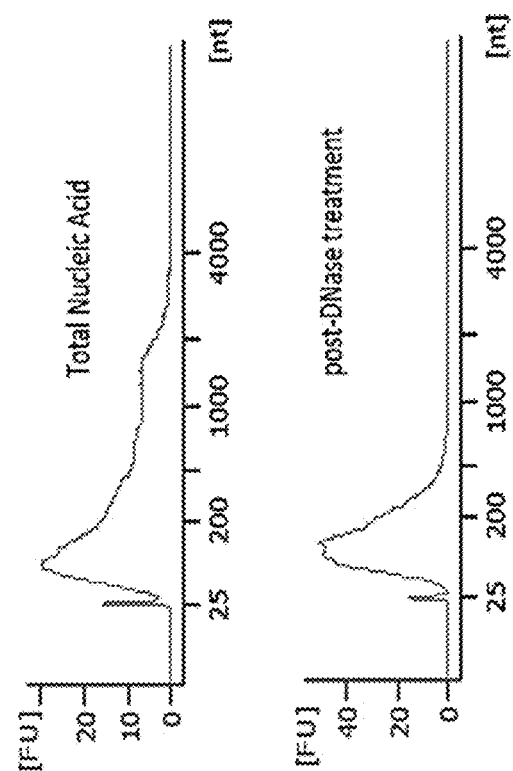
FIGS. 2A-2D. Enzymatic digestion of decellularized ECM scaffolds releases small RNA molecules. (A) Agarose gel electrophoresis of RNase A, DNase I or untreated nucleic acid extracted from undigested UBM (control) and Proteinase K or Collagenase digestions. (B) Electropherogram depicting the small RNA pattern of nucleic acid extracted from collagenase digested UBM before (top panel) and after (bottom panel) DNase I treatment. (C) Electropherogram depicting small RNA pattern from collagenase digested samples after DNase I treatment. (D) Small RNA molecules in biologic scaffolds are protected from nuclease degradation.
Figure 2A:
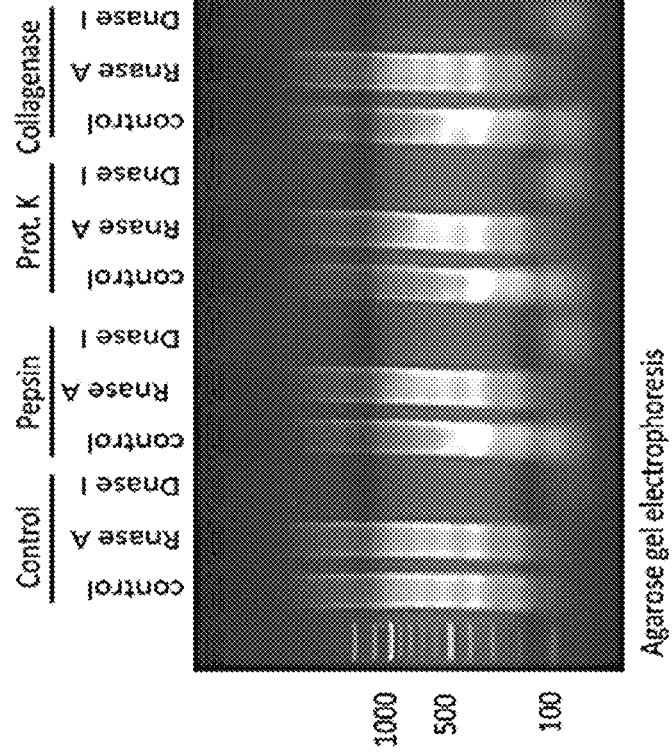
Figure 2C:
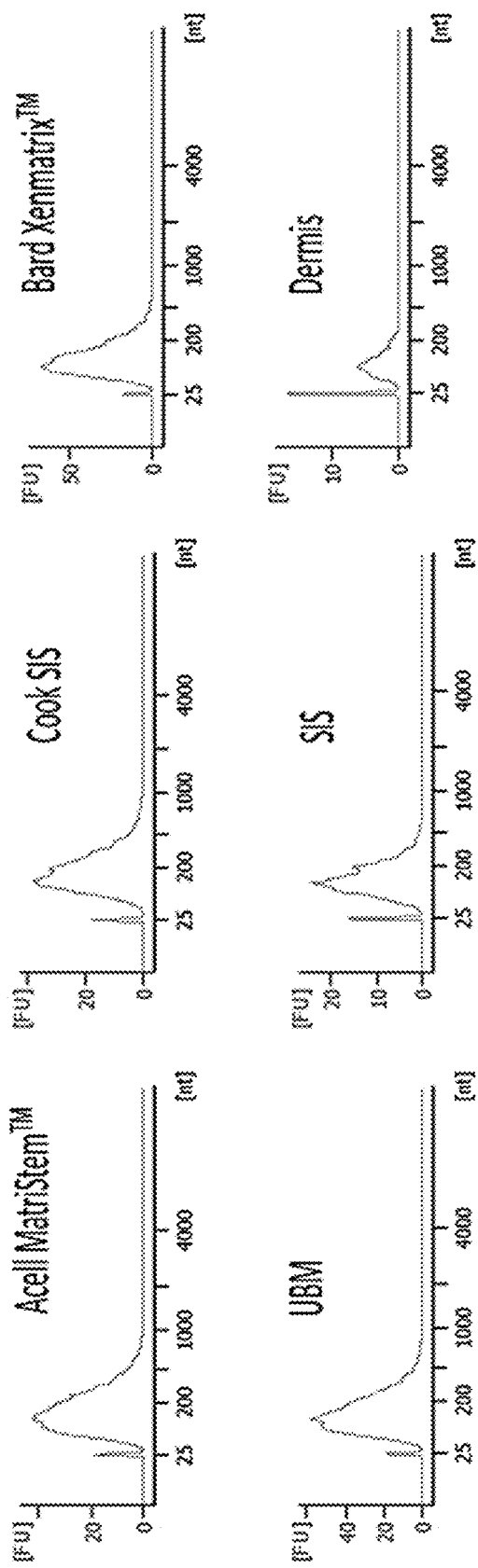
Figure 2D:
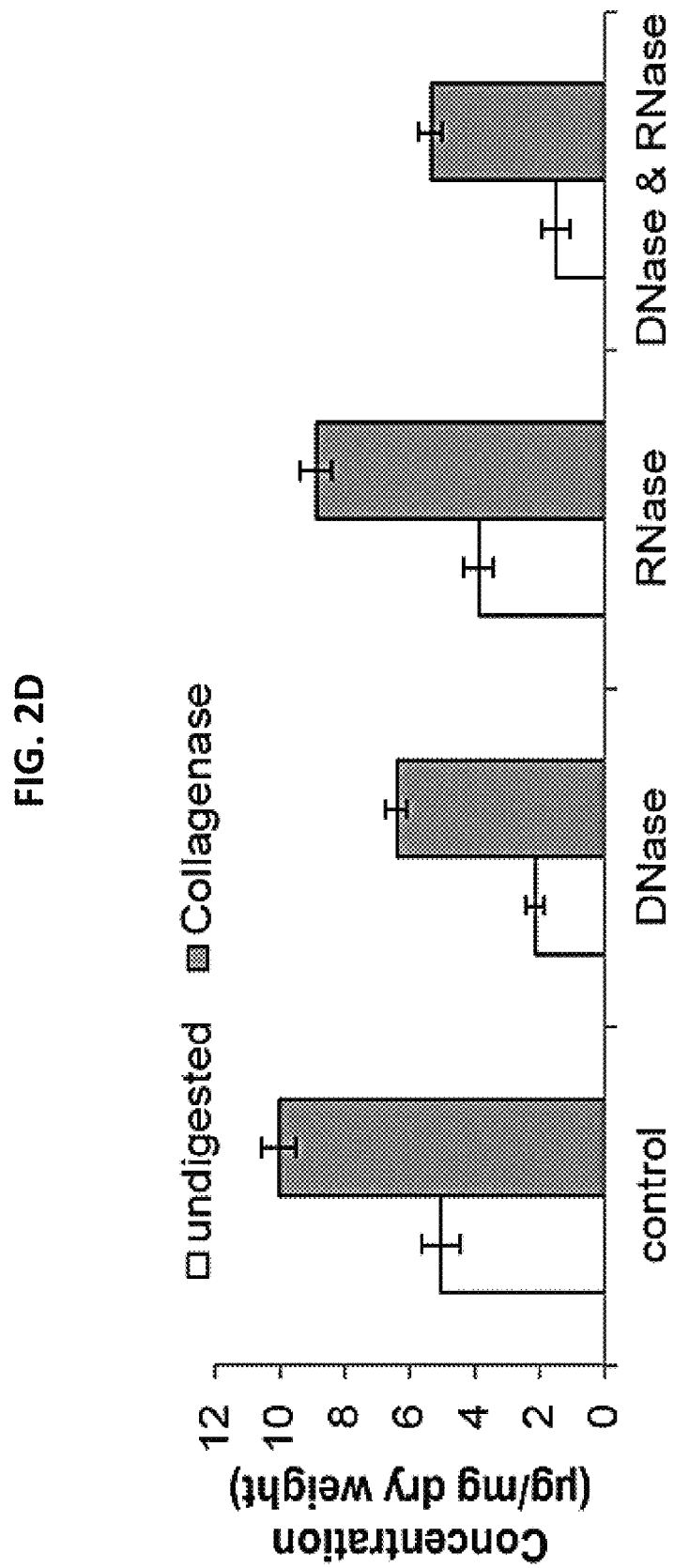

To determine if RNA was present in ECM-scaffolds, the nucleic acid extractions were exposed to DNase I or RNase A nucleases, and the products were analyzed by agarose gel electrophoresis (FIG. 2A). Results show that DNase I treatment removed all nucleic acid material except for a smeared band that ran between ~25-200 bp. Reciprocally, RNase A treatment removed this small nucleic acid fraction, indicating that these short length nucleic acid molecules were, in fact, small RNA molecules. Furthermore, in comparison to undigested control samples, these small RNA molecules could only be efficiently extracted after the ECM-scaffolds were enzymatically degraded (FIG. 2A), a result which paralleled the increase in total nucleic acid observed in FIG. 1. The nucleic acid preps were further analyzed using the Agilent 2100 Bioanalyzer (FIG. 2B). Results show that compared to samples not exposed to nuclease (FIG. 2B, upper panel), DNase I treatment removed all nucleic acid material except for the small RNA molecules within the 25-200 bp range (lower panel), thereby confirming the presence of small RNA molecules in ECM scaffolds. Although the results shown in FIGS. 2A and 2B were obtained using laboratory produced UBM scaffolds, these small RNA molecules were subsequently identified in all biologic scaffolds tested (FIG. 2C). Interestingly, pre-treatment of enzymatically digested ECM-scaffolds with RNase A nuclease, prior to the nucleic acid extraction, failed to remove the small RNA molecules (FIG. 2D). The inability of RNase A to remove the small RNA molecules from enzymatically digested forms of ECM indicated that the RNA was being protected from nuclease degradation, possibly by their incorporation into nanovesicles, which protect RNA cargo from nuclease activity (Koga et al., J Gastrointest Oncol. 2011; 2(4): 215-222).

Example 4

Identification of ECM-Embedded Nanovesicles

Figure 3B:
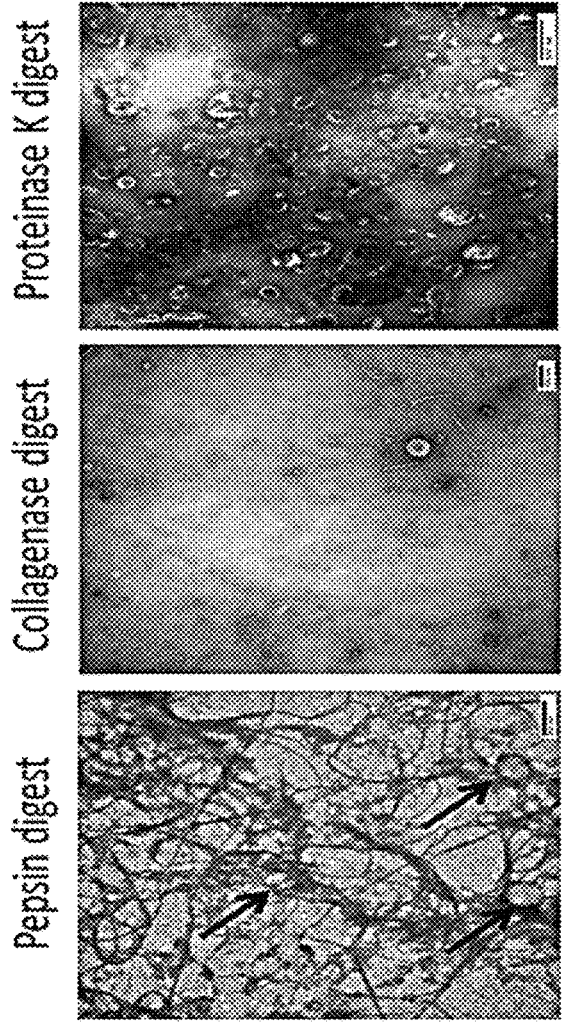
FIGS. 3A-3F. Identification of ECM-embedded nanovesicles. TEM imaging of hydrated UBM stained positive with osmium as rounded structures were identified (A). Enzymatic digestion with Pepsin protease resulted in partial digestion as MBVs are trapped within the fibers. Complete digestion with Collagenase or Proteinase K resulted in complete separation of MBVs from ECM fibers as evident in TEM images (B). Proteinase-K digested ECM (100 mg) from three commercial and laboratory-produced products (C) reveals the presence of MBVs embedded within the ECM in all samples. MBVs protein cargo signature was evaluated using SDS-page Silverstain for ECM products. Protein signature was different for each sample (D). Western blot analysis was performed on two exosomal surface markers CD-63 and CD-81. Expression levels were not detectable as compared to human bone marrow derived mesenchymal stem cells and human serum controls (E). Validation of MBVs size was measured via Nanosight. Particle size was consistent with MBVs (F). Data are presented as means±s.d., n=1.
Figure 3A:
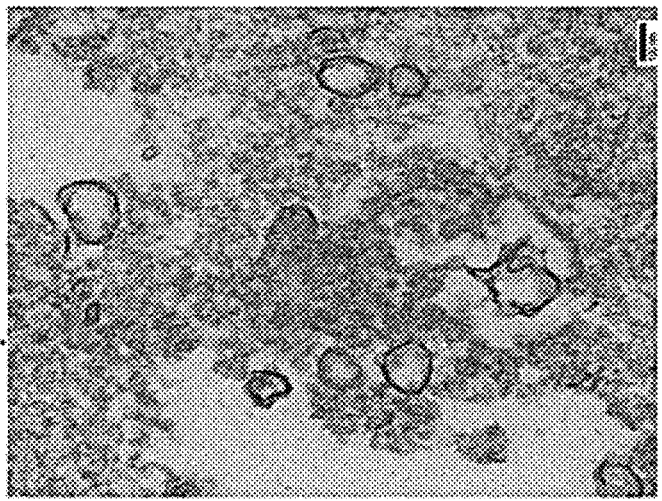
Figure 3C:
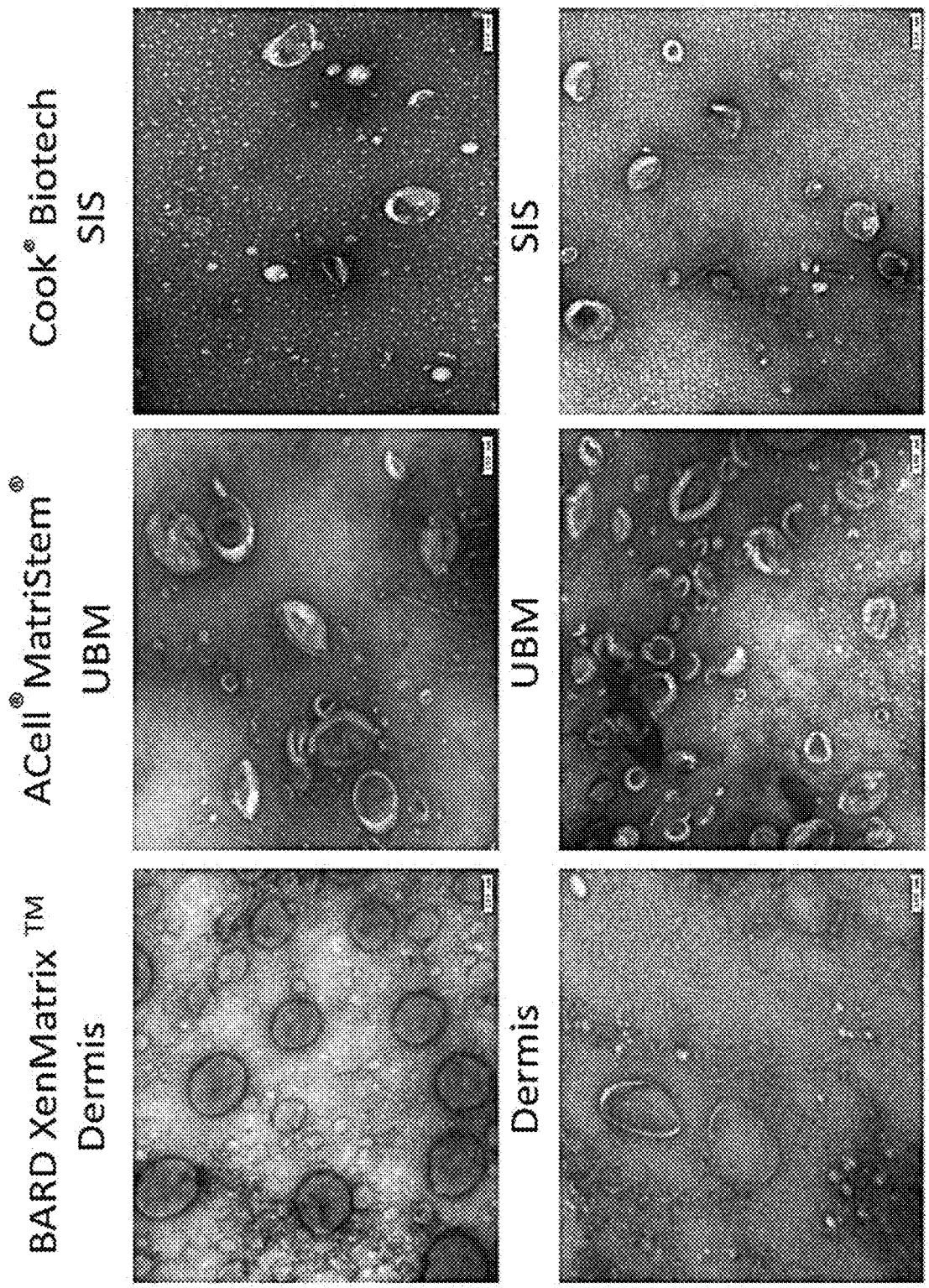

The first evidence of nanovesicles embedded within ECM was obtained using transmission electron microscopy (TEM) on an osmium tetroxide fixed UBM sheet. Rounded structures were identified that stained positive for osmium, indicating the presence of lipid membranes (FIG. 3A). This observation was followed by demonstrating that these nanovesicles could be separated from the matrix only after enzymatic digestion of the ECM-scaffold material. Enzymatic digestion with Pepsin protease (FIG. 3B, left panel), which only partially digests the ECM-scaffold, revealed that these nanovesicles are literally woven into the collagen network of the matrix itself. However, after complete digestion of the ECM-scaffold with Collagenase or Proteinase K (FIG. 3B, right panels), these nanovesicles could be completely separated from the fiber network. The structure, composition and size of these vesicles are compatible with what would be expected from nanovesicles and exosomes. By utilizing a strategy of enzymatic digestion coupled with ultracentrifugation, these nanovesicles were isolated and purified from all tested forms of ECM-scaffold materials including commercially available products (FIG. 3C). These results represent the first identification of nanovesicles embedded within the extracellular matrix.

Figure 3E:
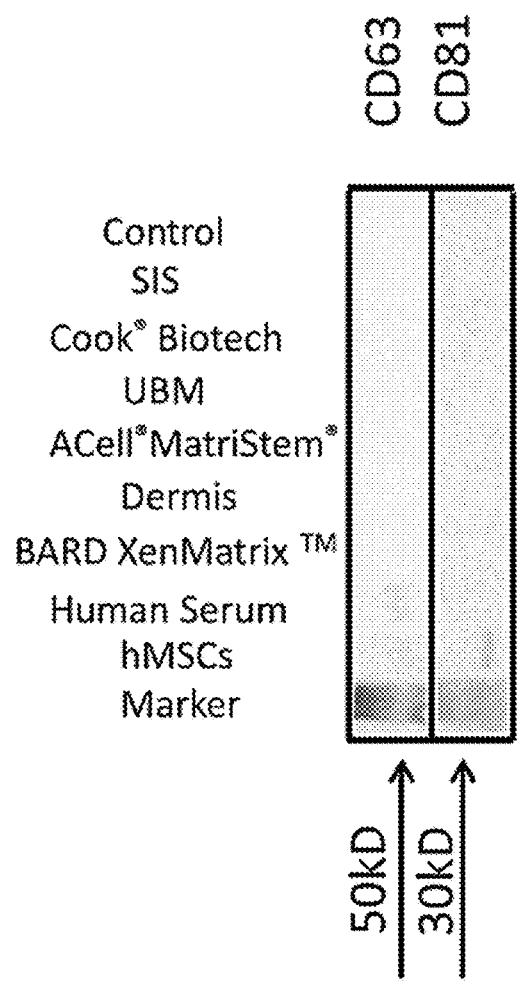
Figure 3D:
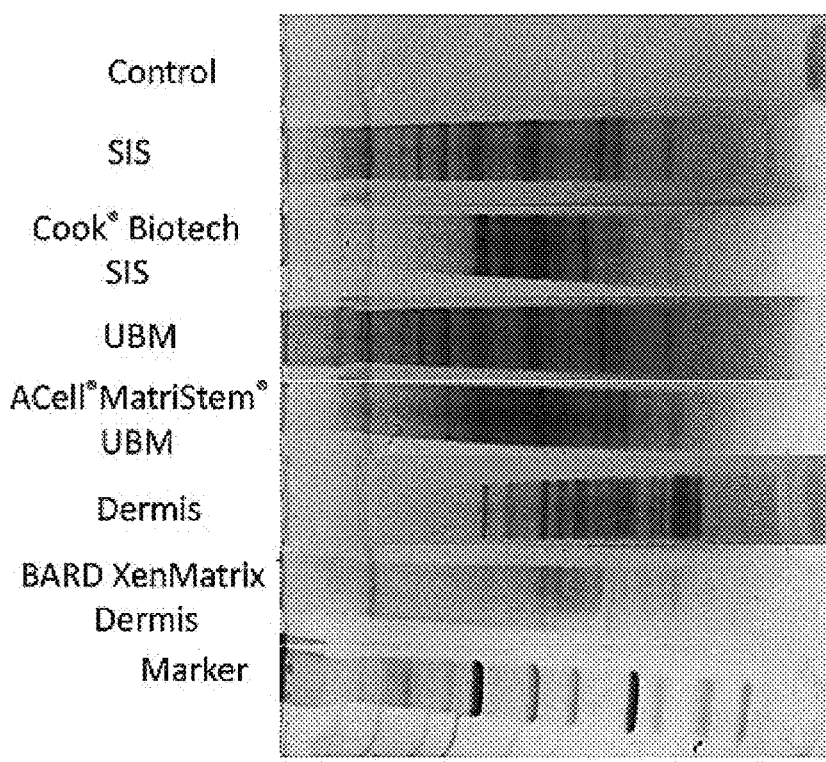

It was then assessed the nanovesicle protein cargo between the different products via SDS PAGE and Silver-stain. The band pattern across the different commercial products and their parallel in-house products was found to be distinctively different. Interestingly, both of the in-house, UBM and SIS, products presented with a similar banding patterns (FIG. 3D).

CD63 and CD81 are amongst the most commonly used validation surface markers for exosomes. Using Western blot analysis (FIG. 3E) no positive bands were detected in all samples for CD63 or CD81. The positive control, human bone marrow-derived mesenchymal stem cell exosomes was positive for both markers, whereas the human pooled serum exosomes were positive only for CD63. This indicates that nanovesicles and exosomes embedded within the ECM have different characteristics then circulating exosomes.

Figure 3F:
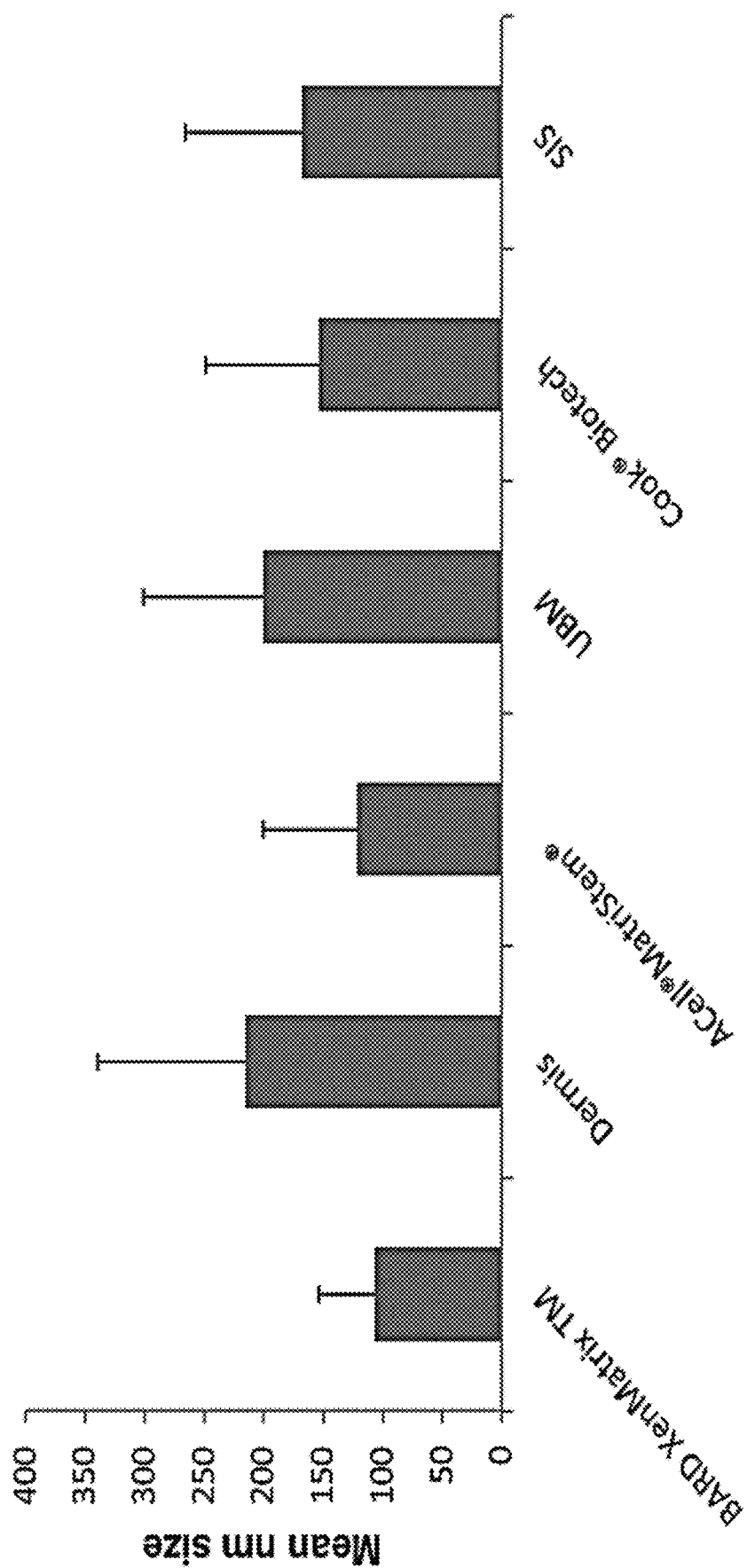

Nanoparticle Tracking Analysis (NTA) was preformed to determine the mean size of nanovesicles for each sample. All samples were found to be consistent with nanovesicles size, ranging from 107 nm-216 nm (FIG. 3F).

Example 5

NGS Discovers a Unique miRNA Signature in Nanovesicles Cargo

Isolated ECM nanovesicles from the different commercial products and the parallel in-house were treated with RNAse for 30 minutes to degrade any remnant RNA from the decellulraizain process ("free RNA") prior to the RNA isolation step. This step was preformed to secure that RNA sequencing data will represent only RNA within the nanovesicles. Interestingly, nanovesicles were able to protect their RNA cargo and no notable changes were found in RNA concentration. RNA sequencing was performed to determine the distinct small RNA profile in each sample. Sequencing data underwent a quality check using fastQC prior to alignment to the human genome (HG19). Samples were then normalized for further analysis and mapped to miRBase (release 21). 33-240 miRNAs were identify per sample and confirms that MIRNA are abundantly present in ECM embedded nanovesicles (FIG. 4A). While the in house dermis sample showed the least amount different miRNAs (33), in house UBM had the most (240). Notably, there were over 50% mutual miRNAs between the commercial and the in house products, and almost 80% overlap between ACELL®MATRISTEM® and UBM (FIG. 4A). Ingenuity pathway analysis (IPA) was used to identify pathways, cell and physiological functions. Remarkably, all samples were found to be significantly involved in cellular development, cellular growth and proliferation, cell death and survival, cellular movement and cell cycle (FIG. 4B). Additionally, identify miRNAs were found to play a role in connective tissue development and function (except for in house UBM), organismal development (except for in house dermis and COOK® Biotech) and organ development (except for BARD XENMATRIX™) (FIG. 4C). miRNAs from all samples were found to also be involved in organismal injury and abnormalities. In addition, in house UBM was the only one sample associated with skeletal and muscular disorders. These results can partially explain the signaling by which ECM achieves its effects downstream.

Example 6

Exposure to ECM Embedded Nanovesicles can Alter Cell Behavior

Figure 5A:
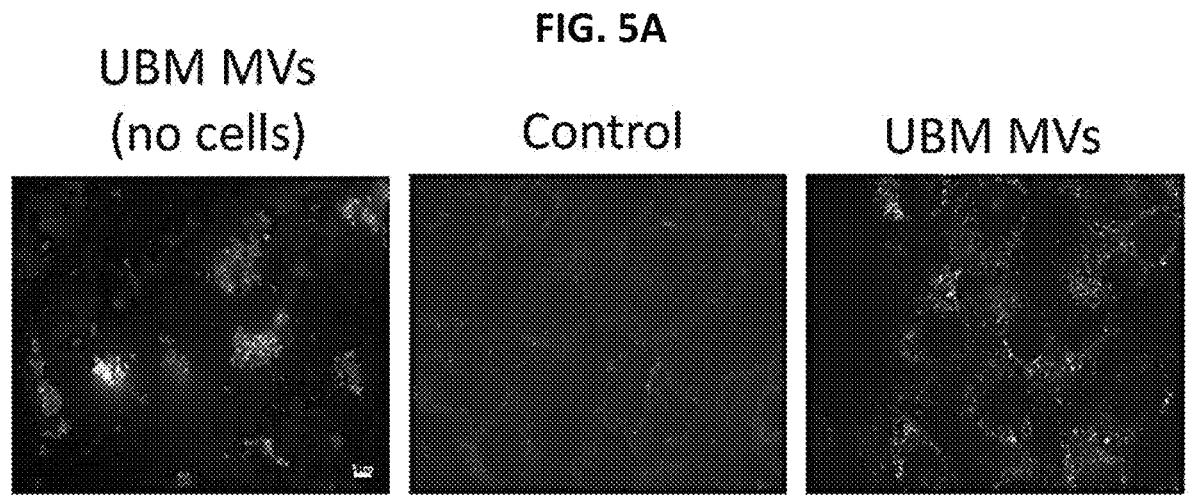
FIGS. 5A-5F. Nanovesicle uptake in C2C12 (A). Neurite extension assays using NIE-115 cells (B). PVSC (n=3) had a significant change in morphology effecting their mobility as seen by the scratch assay (C). Hemocytometer was used to quantify the increase observed in cell number (D). Nanovesicle isolated from UBM bioscaffolds promote a constructive, M2 macrophage phenotype. (E) Bone marrow was isolated from C57bl/6 mice and cultured in media supplemented with macrophage-colony-stimulating-factor (MCSF) to derive macrophages. Macrophages were treated with 20 ng/ml IFNγ and 100 ng/ml LPS to derive M1 macrophages, 20 ng/ml IL-4 to derive M2 macrophages and 5 ug/ml (protein/volume) of isolated exosomes from a UBM source. Macrophages were fixed and immunolabeled for the pan-macrophage marker (F4/80), and strong indicators of the M1 (iNOS) and M2 (Fizz1) phenotype. Nanovesicle treated macrophages are predominantly F4/80+Fizz1+indicating an M2 "like" phenotype. (F) Gene expression in THP-1 is altered by UBM exosome transduction. A: THP-1 were transduced with UBM isolated exosomes (n=3), and gene expression was evaluated 24 hrs later by qPCR for both M1 and M2 associated markers (iNOS, TNFa, STAT1, STAT2, STAT5A, STAT5B, IRF3, IRF4, IRF5, IL1RN, CD206, TGM2, STAT3, STAT6, KLF4, PPARg). Nanovesicles exposure dose for all of the above experiments was 50 ug/ml (protein/volume).

Nanovesicles isolated from UBM were labeled based on Orange Acridine chemistry. In FIG. 5A, red fluorescence represent RNA whereas green DNA. Successful nanovesicles content labeling was demonstrated, as well as nanovesicles cargo engulfed by muscle myoblat C2Cl2 cells. This experiment is a proof of concept that isolated nanovesicles content can integrate with target cells.

Figure 5B:
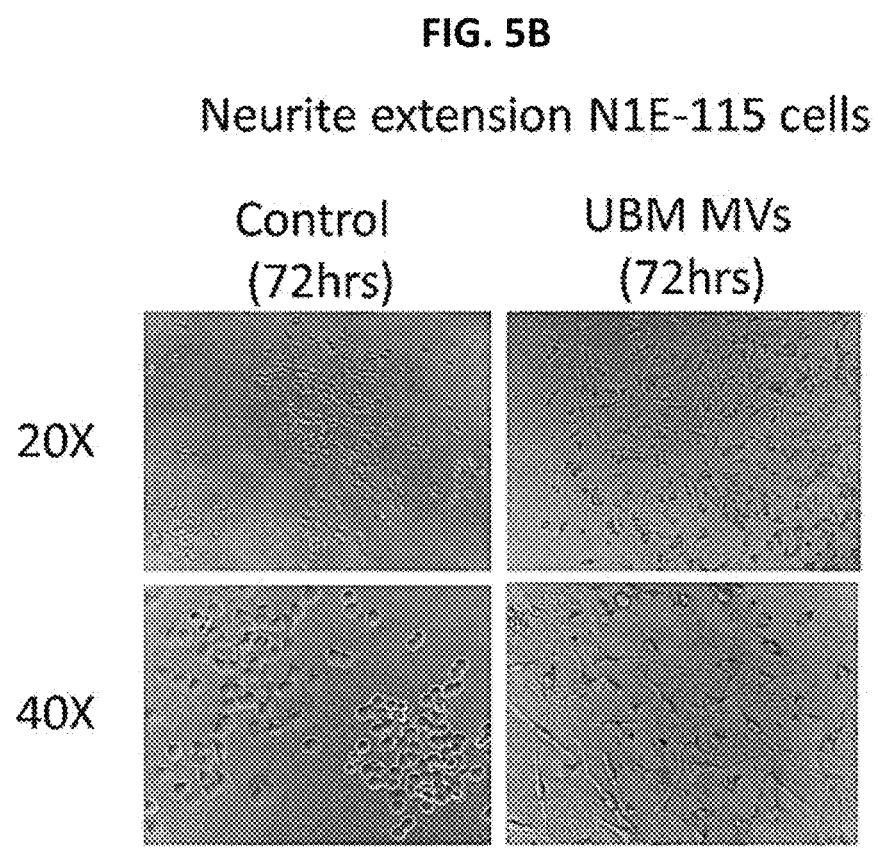

Neuroblastoma cells (NIE-115) were found to have Neurite extension 5 days post UBM-ECM degradation products treatment. That effect was mimicked using only nanovesicles which were isolated from collagenase digested UBM. Impressively, within 3 days post exposure to UBM nanovesicles the NIE-115 cells showed Neurite extension, whereas no change was evidence in the control group (FIG. 5B).

Figure 5C:
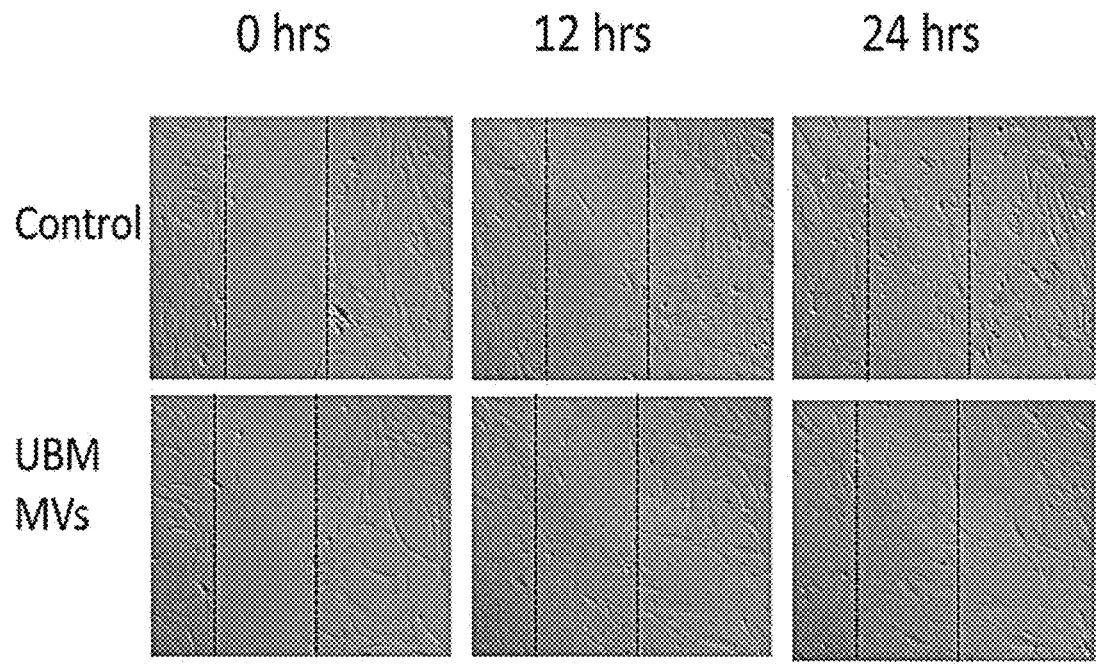
Figure 5D:
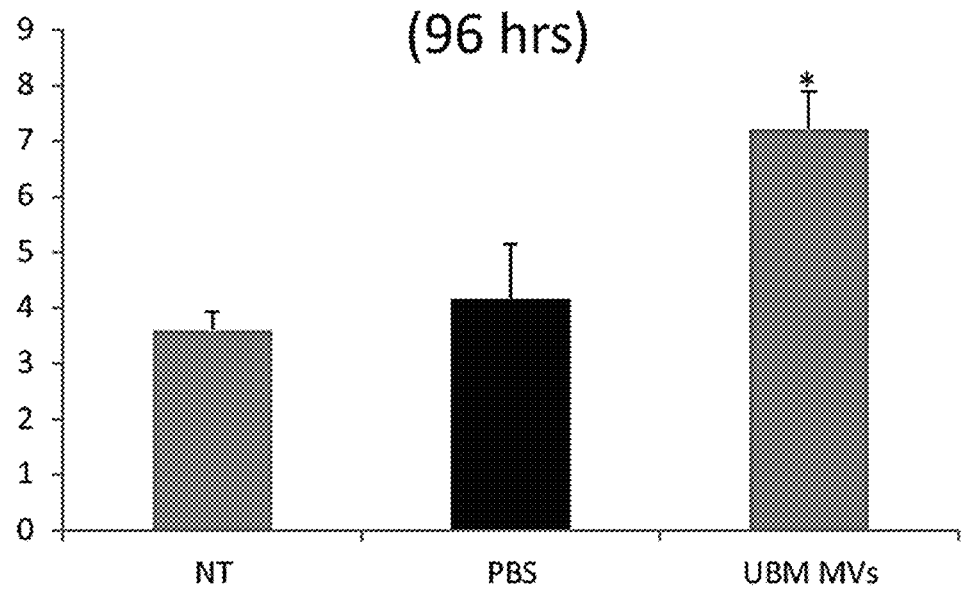
Figure 5E:
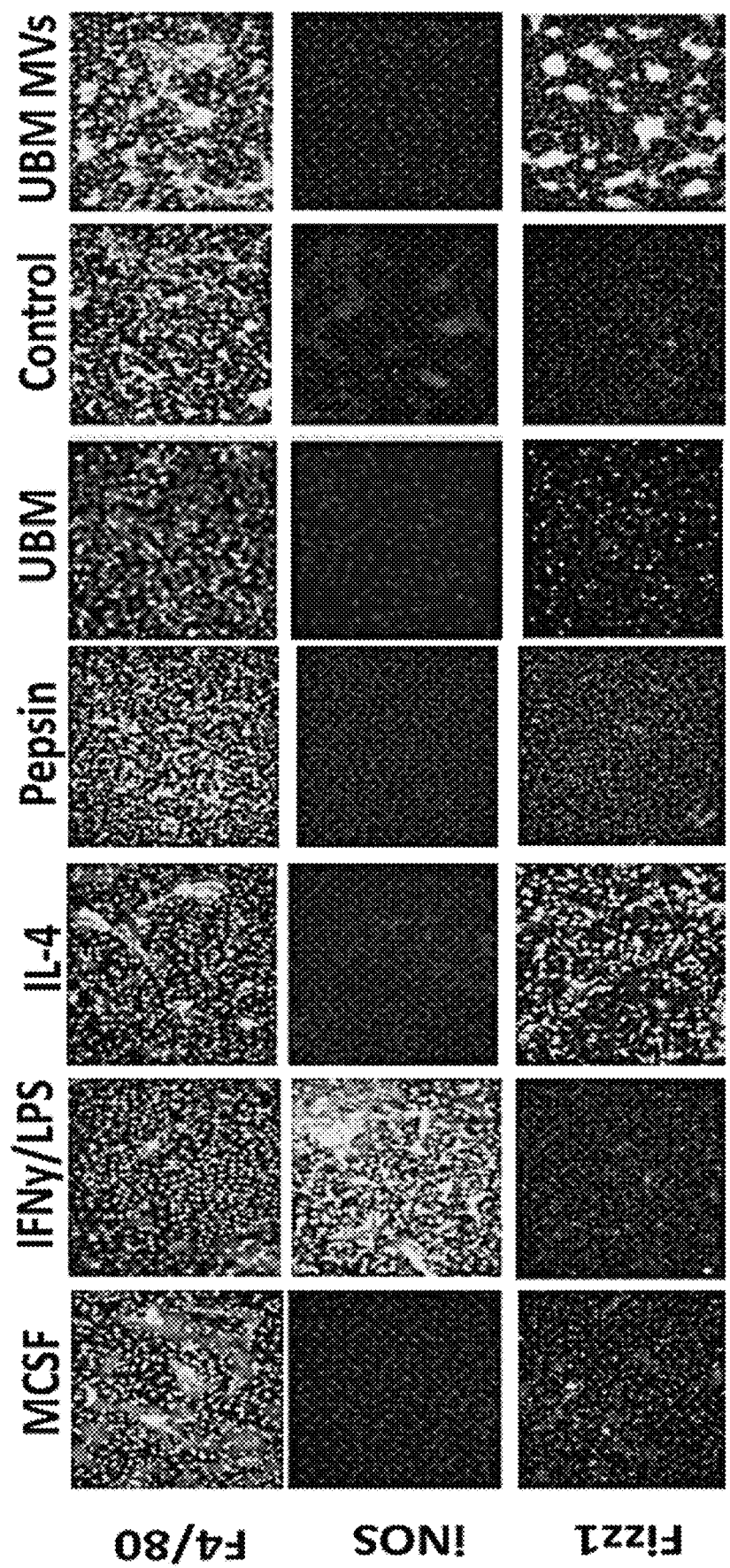
Figure 5F:
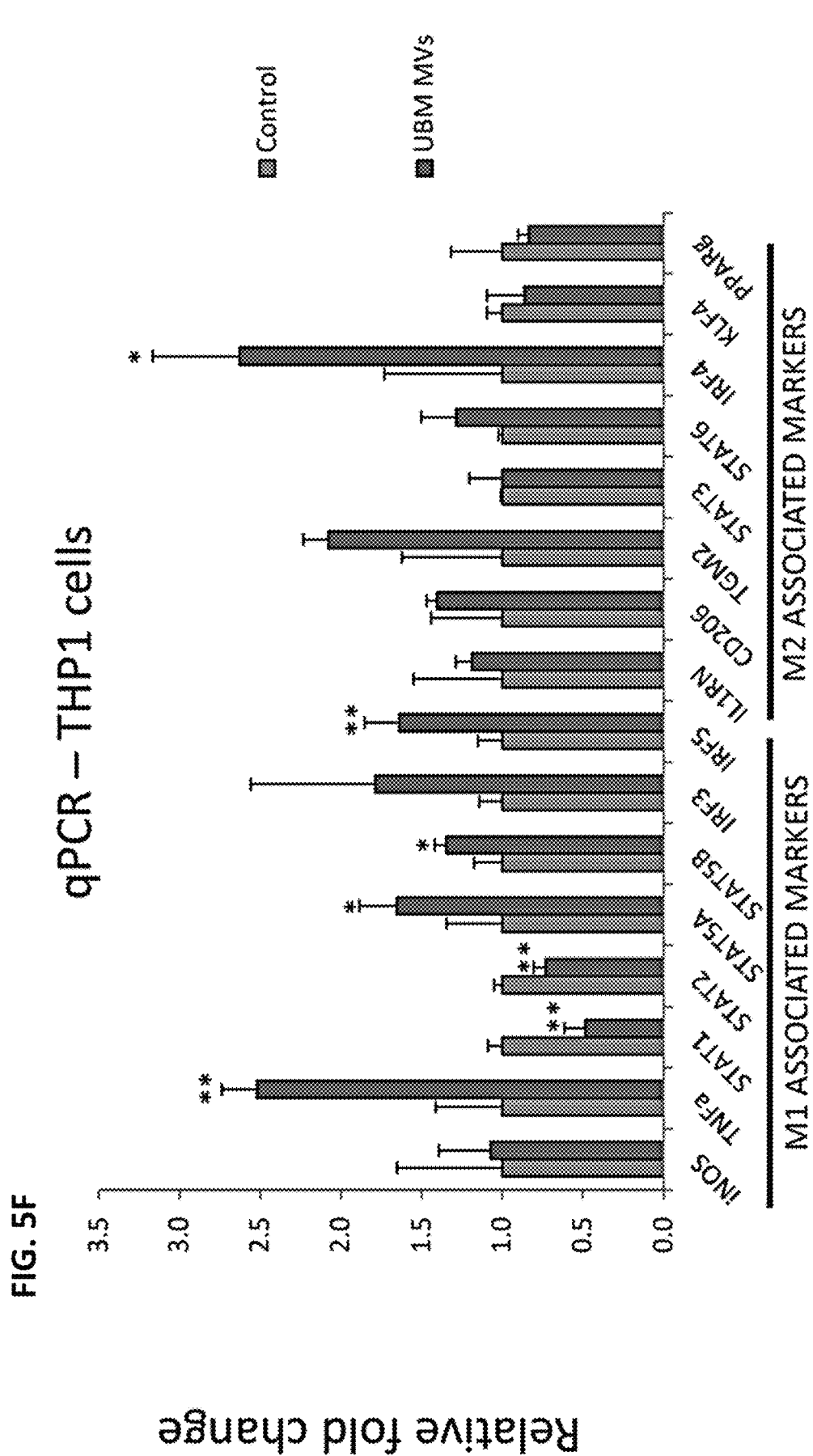
Figure 7:
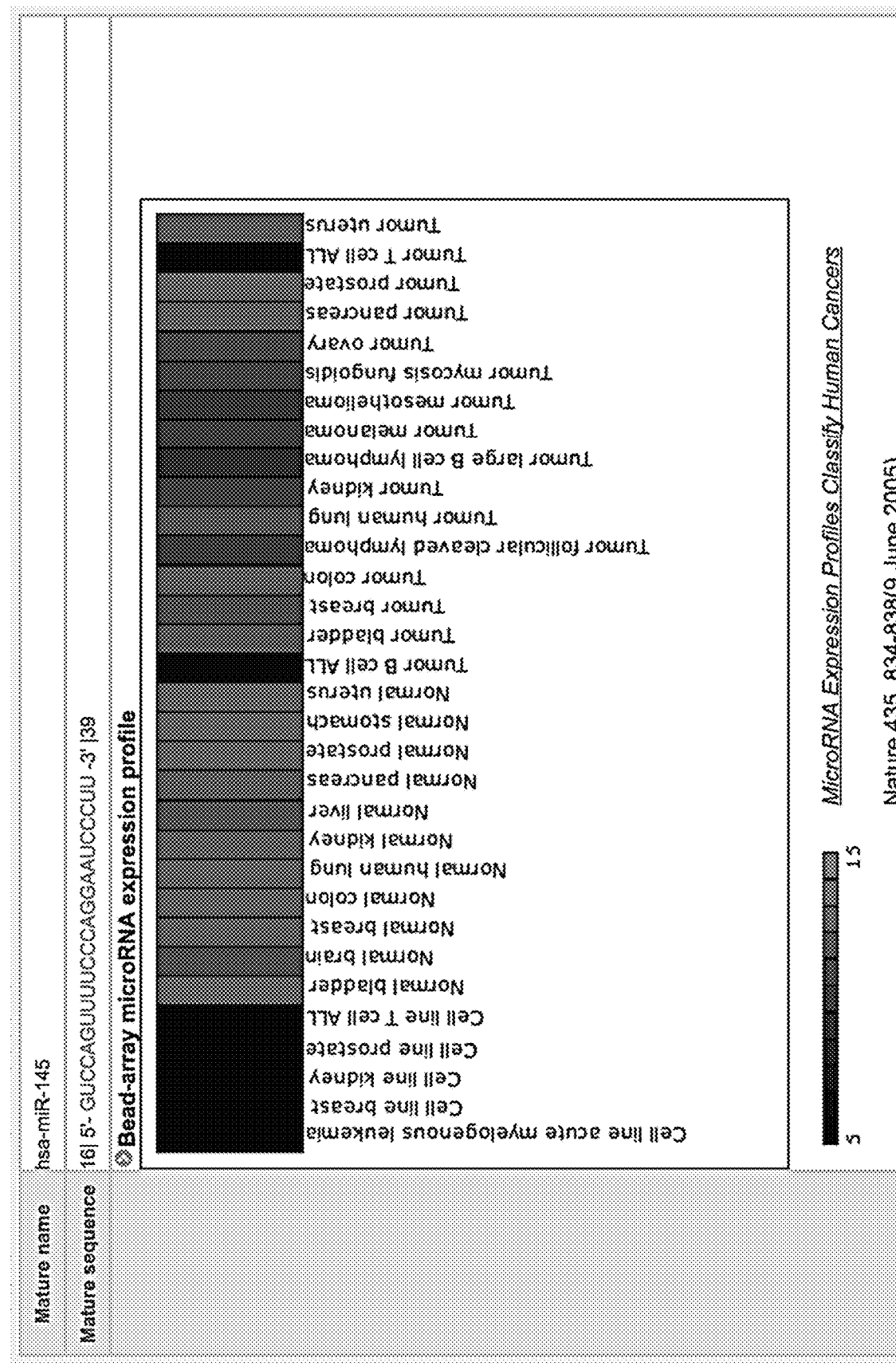
FIG. 7. Mir-145 expression profile amongst different tissues and cell lines. Mir-145 is highly expressed in normal tissues. It is expressed to a lesser degree in tumors. It is not expressed in T or B-Cell tumors, nor in specific cell lines. SEQ ID NO: 3 is shown.

It was then determined whether Perivascular stem cells (PVSC) exposure to nanovesicles can affect their ability to repopulate a scratched area in a confluent culture. As depicted in FIG. 5C, PVSC exposed to nanovesicles were faster to regain full confluence over a wounded area in the scratch assay 24 hours post exposure. Additionally, an increase in cell count was noted 96 hours post exposure to nanovesicles compared to control (FIG. 5D).

The effect of ECM embedded nanovesicles was assessed on macrophage polarization. It has been shown that ECM degradation products (such as UBM and SIS) can promote an M2 "like" phenotype (Sicari et al., Biomaterials 2014 October; 35(30):8605-12). BMDM were exposed to nanovesicles isolated from UBM for 24 hours. Exposure to nanovesicles promoted an M2 "like" macrophage activation similar to IL-4 exposure control. The M2 macrophage phenotype was confirmed using Fizz-1 immunofluorescence staining. Notably, no changes were noticed in the M1 marker iNOS.

Using qPCR, gene expression was examined for both M1 and M2 associated markers following nanovesicles exposure in THP-1 cells for 24 hours. Significant changes were noted in the M1 markers. While an increase in TNF-α, STAT5A/B and IRF5 gene expression levels was observed, STAT1/2 expression levels were decreased. In the M2 associated markers panel, TGM2 and IRF4 both showed an increase post nanovesicles exposure but only IRF4 was found to be statistical significant.

Example 7

Additional Isolation Methods

Figure 8A:
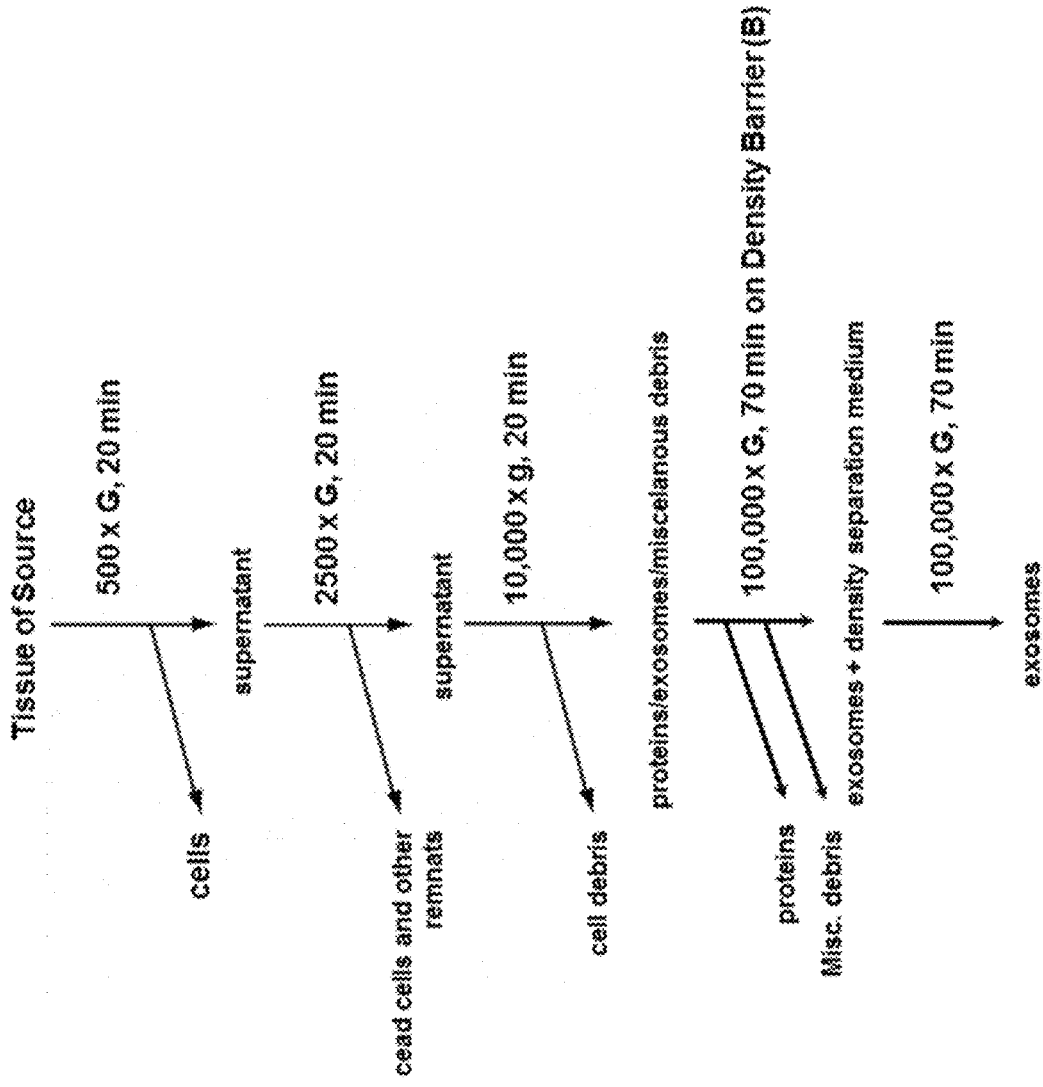
FIGS. 8A and 8B. Schematic diagrams showing an additional isolation method. Additional details of this method are provided in Example 7.
Figure 8B:
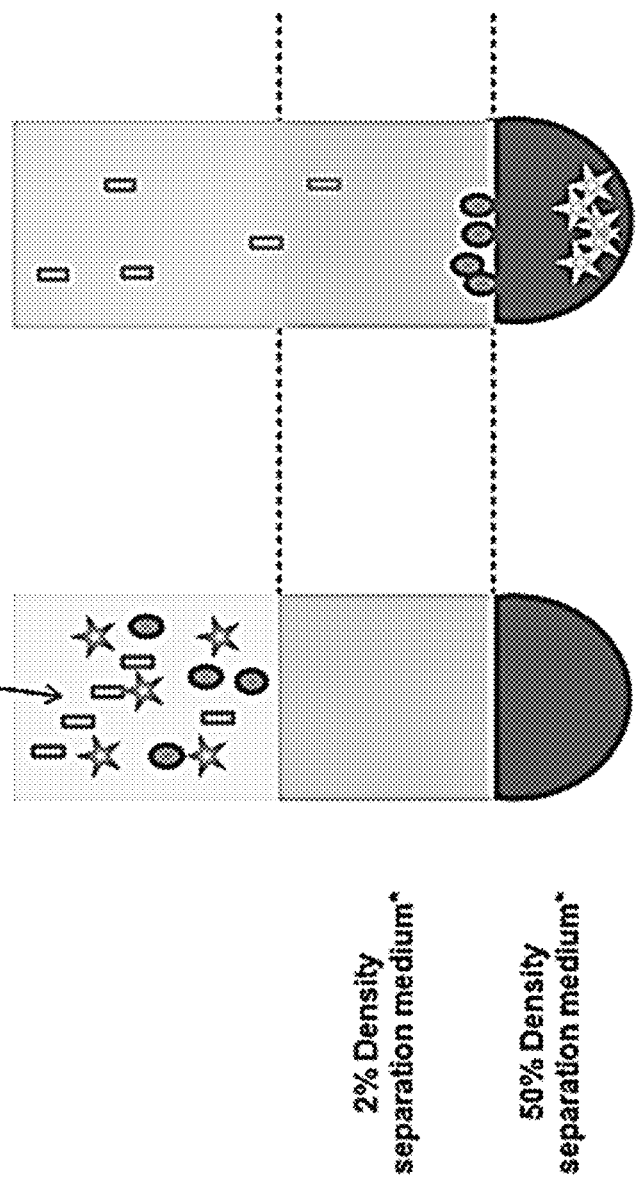

The protocol shown in FIGS. 8A and 8B allows for the isolation of the exosomes within a tissue. A piece of tissue (which might be pretreated, lyophilized, frozen, taken from a biopsy, necropsy or other source) is first enzymatically digested and then it is run by differential centrifugation in order to remove cells, cell remnants and other contaminants that might not be desired in the final sample. After these centrifugation steps, the supernatant is placed on top a gradient that includes a density barrier which can be made of iodixanol, sucrose or other density gradient mediums. The concentration of this medium can be varied according to the tissue and profile of exosomes to be isolated. The gradient is then ultracentrifuged, the fraction at the density barrier is collected and ultracentrifuged one more time to wash the density gradient medium and other undesired remnants. The final conserved pellet are the exosomes isolated from the initial piece of tissue.

The exosomes collected from the tissue can be used in any of the methods disclosed herein. These methods are also of use for profiling, treatment of cells, and the further characterization of the exosomes present in tissue samples.

Example 8

Use of ECM-Nanovesicles to Recruit Cells, Promote Cell Growth, and Promote Cell Differentiation Previous studies have shown that (acellular) ECM bioscaffold materials can facilitate constructive, functional skeletal muscle repair and regeneration (Mase et al., Orthopedics. 2010; 33(7):511; Sicari et al., Tissue Eng Part A. 2012; 18(19-20): 1941-1948). ECM-nanovesicles can recapitulate the functional muscle remodeling response observed with intact ECM-scaffolds. A murine model of volumetric muscle loss is used. It has been shown that placement of an ECM scaffold at the site of muscle injury results in a significant deviation from the default response of scar tissue deposition toward a constructive remodeling outcome (Sicari et al., Tissue Eng Part A. 2012; 18(19-20): 1941-1948). ECM-nanovesicles facilitate many of the effects attributed to intact biologic scaffolds including the recruitment and differentiation of endogenous stem/progenitor cells, regional angiogenesis, innervation and modulation of the innate immune response.

a. Murine model of volumetric muscle loss: The αSMA-GFP mouse model (C57BL6) expressing GFP under the control of the αSMA promoter is used in these studies. This transgenic mouse model (Yokota et al., Stem Cells. 2006; 24(1): 13-22; Kalajzic et al., Bone. 2008; 43(3):501-510), allows tracking of the fate of infiltrating progenitor cells during skeletal muscle regeneration. A critical size defect is created in the quadriceps muscle of the mouse. Briefly, a 0.5-1.0 cm incision running parallel to the proximal-distal axis of the thigh is made directly over the quadriceps muscle. A sterile biopsy punch is used to remove a section of the muscle approximately 3 mm$^2$ (approximately 70% defect). The defect is replaced with one of the following test articles: 1) ECM hydrogel, 2) ECM-nanovesicles suspended in sterile PBS, or 3) PBS vehicle control. Unrepaired defects serve as a control group. The ECM-hydrogel test article is layered within the defect, covered with a sheet of the same ECM, and non-degradable polypropylene sutures will be placed to clearly identify the injury and/or implantation site at the time of tissue harvest. ECM-nanovesicles and the PBS control treatments are administered by direct injection into the wound edges at the border of the injury site. Nanovesicle quantitation and dose response experiments are used as a guideline to determine appropriate concentrations to be used for the in vivo study. Animals receiving ECM-nanovesicle treatment are randomly divided into two separate groups: group 1 receives a single injection at the time of injury, and group 2 receives additional injections on days 4, and 7 post-injury. Mice are sacrificed at designated time points which include early (3, 6, 12 and 24 hours), and late time points (4, 7, 14 and 28 days) post-surgery. At each time, the defect site is explanted with a small portion of the surrounding native tissue. Sample sizes are determined by power analysis to achieve a significance of <0.05, and statistical analysis performed.

Histomorphologic Analysis. Explanted specimens are fixed in formalin and stained with hematoxylin and eosin. Histologic sections are evaluated using previously validated quantitative criteria for aspects of inflammatory and tissue remodeling response (Valentin et al., J Bone Joint Surg Am. 2006; 88(12):2673-86). Criteria include the density of cellular infiltration, the phenotype of infiltrating cells, vascularity, connective tissue organization, encapsulation, and the presence of muscle cells within the site of implantation. The suture sites re avoided in the morphologic evaluation.

Determination of Macrophage Phenotype by Immunolabeling. Immunolabeling is performed on sections of the implant sites as previously described (Brown et al., Acta Biomater. 2012; 8:978, 2012). Each explant specimen is exposed to antibodies to a pan-macrophage marker (CD68), an M1 macrophage phenotype marker (CCR7), and an M2 macrophage phenotype marker (Fizz1). The immunolabeled specimens are examined and imaged using a Nikon e600 microscope equipped with a Nuance multi-spectral imaging system. Fluorescence images are subjected to spectral unmixing and re-coloring for autofluorescence removal and quantitative analysis. The images are evaluated in a blinded fashion to determine the ratio of the number of M2 (Fizz1+) cells to M1 (CCR7+) cells.

Functional assessment. The functionality of the remodeled tissue is assessed by in vitro muscle contraction studies. An in vitro organ bath system is used to study the contractile force generated by isolated quadriceps muscle strips from both remodeled muscle and uninjured muscle in response to electrical field stimulation. The optimal voltage and tissue length to produce maximal twitch response is determined and recorded. Functional innervation of the regenerated tissue also is assessed using labeled alpha-bungarotoxin and immunolabeling for beta-tubulin 3 to identify nerve fibers and functional motor endplates. The combination of muscle contraction and neuronal labeling facilitates the evaluation of muscle strength and function.

Migration of perivascular cells. Infiltration of perivascular progenitor cells to the injury site is assessed through detection of the GFP-signal co-localized with positive staining for CD146 and NG2. The contribution of the perivascular cells to the tissue remodeling of skeletal muscle defects over time is assessed histologically using markers for skeletal muscle (MyoD, skeletal muscle actin, myosin and calsequestrin), nerve (beta-tubulin 3, neurofilament, GFAP) and blood vessels (CD31, von Willebrand factor). Co-localization of these markers with the GFP label is used to identify the differentiation of these cells into key structures of skeletal muscle tissue remodeling. In addition, immuno-markers for perivascular cells i.e. CD146, NG2, and CD133 is used to confirm the presence of undifferentiated perivascular cells within the remodeled tissue. Muscle sections also are immunohistochemically stained for multiple markers of cell proliferation (e.g. Ki67, PCNA) in order to morphologically assess the shift in regeneration from proliferation to differentiation.

The addition of ECM-nanovesicles isolated from bioscaffolds promotes an immunomodulatory response towards a constructive M2-like macrophage phenotype, and an increased differentiation of migrating perivascular cells into new muscles fibers accompanied by increased innervation. However, although improvement is achieved, there is not complete restoration of all muscle functions.

Thus, ECM-embedded nanovesicles represent a unique class of exosomes with biologic properties and functions distinct from circulating exosomes, and mediate many of the inductive properties of ECM scaffolds associated with constructive, functional remodeling.

Example 9

ECM-Derived Nanovesicles can be Isolated by Re-Suspending the ECM in PBS with the Addition of Salt (KCl)

100 mg of lyophilized ECM from Urinary Bladder (UBM) were resuspended in PBS, hydrated for 30 mins at 37 C, and then KCl at different concentrations was added into the UBM-PBS suspension. The suspension with KCl was incubated for 1 hr at 4 C. The sample was centrifuged for 30 minutes at 4,500G, to remove the ECM components, the supernatant was collected, passed through a 0.2 uM filter and transferred into an ultracentrifuge tube, where it was ultracentrifuged at 100,000G for 2 hours to pellet and obtain MBVs.

The quantity of ECM-derived nanovesicles, also called membrane bound vesicles (MBVs) in Examples 9-14) was compared by determining the amount of RNA after RNase treatment. The final sample was treated with RNase A at a concentration of 0.5 ug/uL for 20 minutes at 37 C, then RNA was isolated and quantified from the sample. Since extracellular vesicles, such as MBVs are known to protect RNA from degradation by RNases, the amount of RNA obtained, relates to the amount of MBVs since any unprotected RNA would have been degraded by the RNase and not been quantifiable.

Figure 9A:
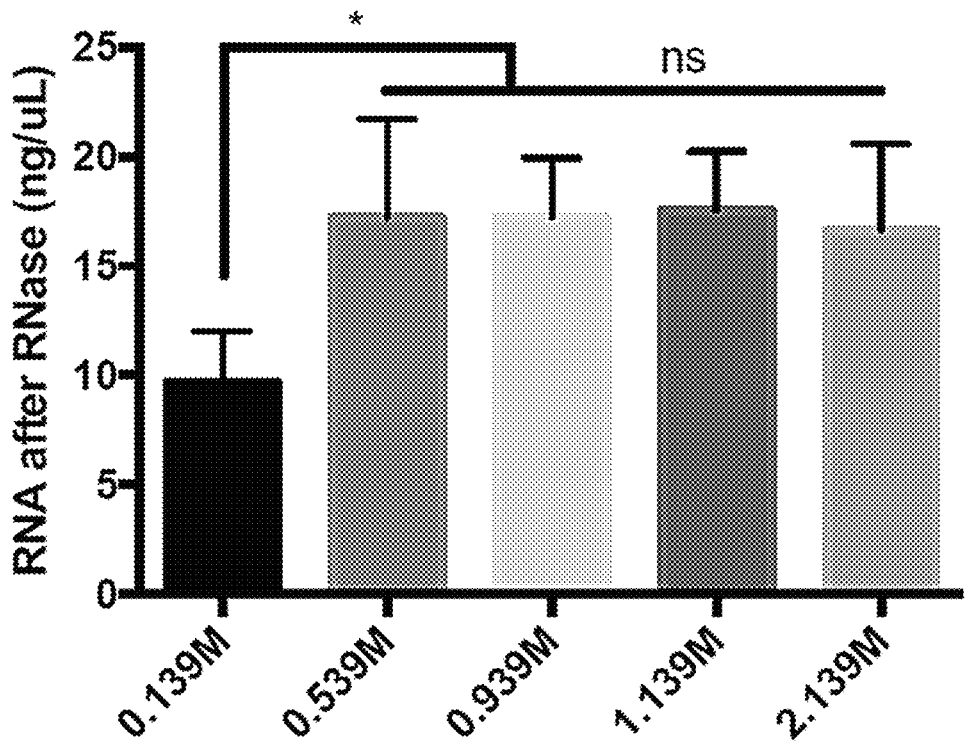
FIGS. 9A and 9B. A. KCl isolation. The addition of KCl allows for the isolation of matrix bound nanovescicles (MBVs) from the ECM with ultracentrifugation, however no differences or benefit is seen when increasing the KCl concentration. (ns=no significant differences, *=p<0.05) B. TEM of MBVs isolated with the addition of 0.2M KCl to PBS.
Figure 9B:
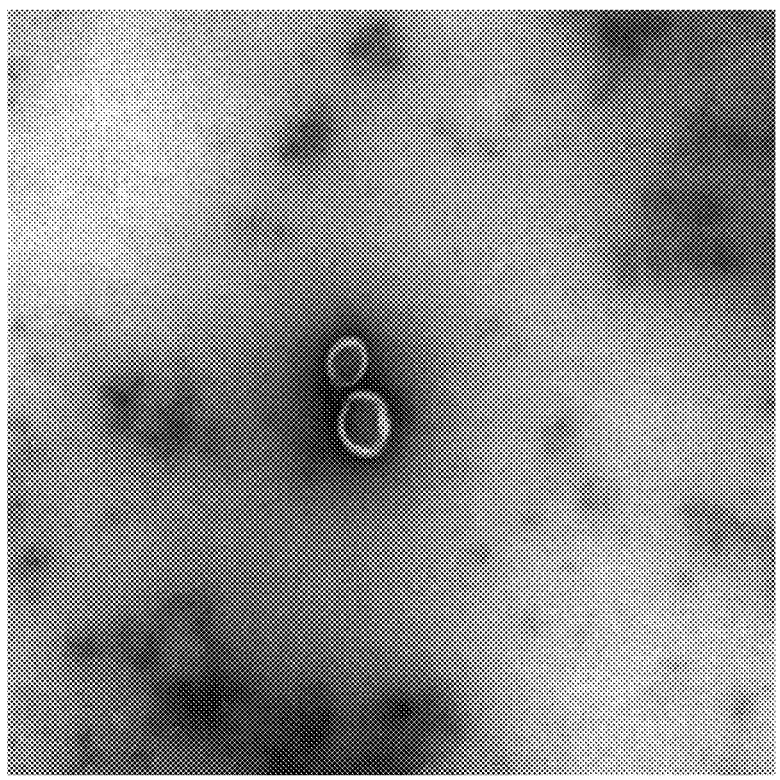

Through this method it was determined that the addition of KCl to PBS increased the amount of RNase resistant RNA, which represents the amount of MBVs, however the additional concentration of KCl above 0.4M did not increase the amount of MBVs that could be isolated (FIG. 9A). Transmission Electron Microscopy shows the characteristic morphology and size of MBVs isolated using KCl (FIG. 9B).

Example 10

Salt Isolation of MBVs Yields Comparable Number of MBVs to Enzyme-Isolation

To compare the amount of MBVs obtained with the different methods, MBVs were isolated using two enzyme-based methods (Collagenase and Proteinase K) and salt-isolation with KCl. MBVs were then quantified based on the RNA quantity after and before RNase treatment.

No significant differences were found between the RNA quantity before and after RNase treatment suggesting that the amount of RNA outside vesicles is minimal for Proteinase K and KCl. There was a higher difference before and after RNase treatment of Collagenase-isolated MBVs. This suggests an outside source of RNA. It is possible that since collagenase is purified from bacteria it could include additional remnant RNA from the Collagenase. Being able to remove the use of enzymes prevents the introduction of foreign undesired elements to the preparation such as those that can be included with the enzyme preparations.

Figure 10:
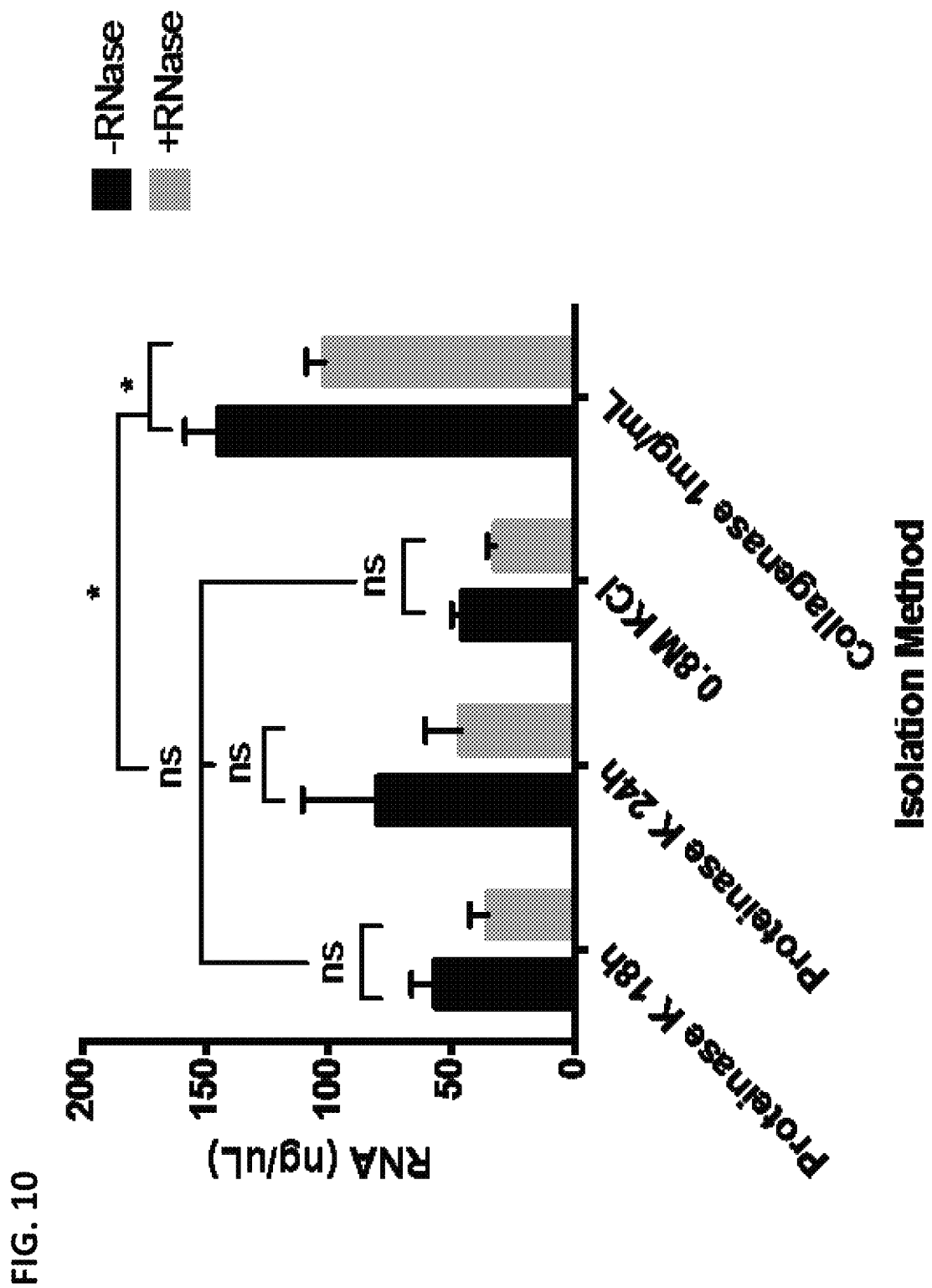
FIG. 10. RNA quantitation. The amount of RNA before and after RNase treatment was quantified for matrix bound nanovessicles (MBVs) isolated by three different methods. There was no difference between the amount of MBVs when using Proteinase K (enzyme based) and KCl (salt isolation) however there was a larger yield when collagenase was used.

There were no differences of the amount of MBVs isolated after Proteinase K treatment for 18 and 24 hour suggesting the maximum amount of MBVs obtainable by this method was reached. The same quantity was obtained from KCl isolated MBVs showing these methods have similar efficiencies. Collagenase at a concentration of 1 mg/mL for 24 hours yields a higher amount of MBVs than both Proteinase K and the use of salt (KCl) (FIG. 10).

Example 11

The Higher Purity of KCl Isolated MBVs Allows for the Use of Efficient Methods for Isolating Extracellular Vesicles Like Ultrafiltration Ultracentrifugation is the most commonly used method for isolating extracellular vesicles as it provides an adequate balance between yield and purity. Methods such as ultrafiltration that are used for concentration of proteins provide a higher yield, at the expense of purity as they co-isolate proteins present in the samples. Ultrafiltration, despite its higher yield, is not feasible for enzyme-based MBV isolation as enzymes generate small fragments from digestion of ECM components that ultrafiltration would not be able to separate from MBVs. In addition, because ultrafiltration is a method that concentrates proteins, it would concentrate the enzyme used for the digestion of the ECM in the final MBV preparation. The use of salt for the dissociation of MBVs does not generate any fragments from the matrix and keeps the ECM in suspension. The ECM can then be removed with a regular centrifugation step while the MBVs are kept in the supernatant. This supernatant with the MBVs can be ultrafiltrated to isolate the MBVs.

Figure 11A:
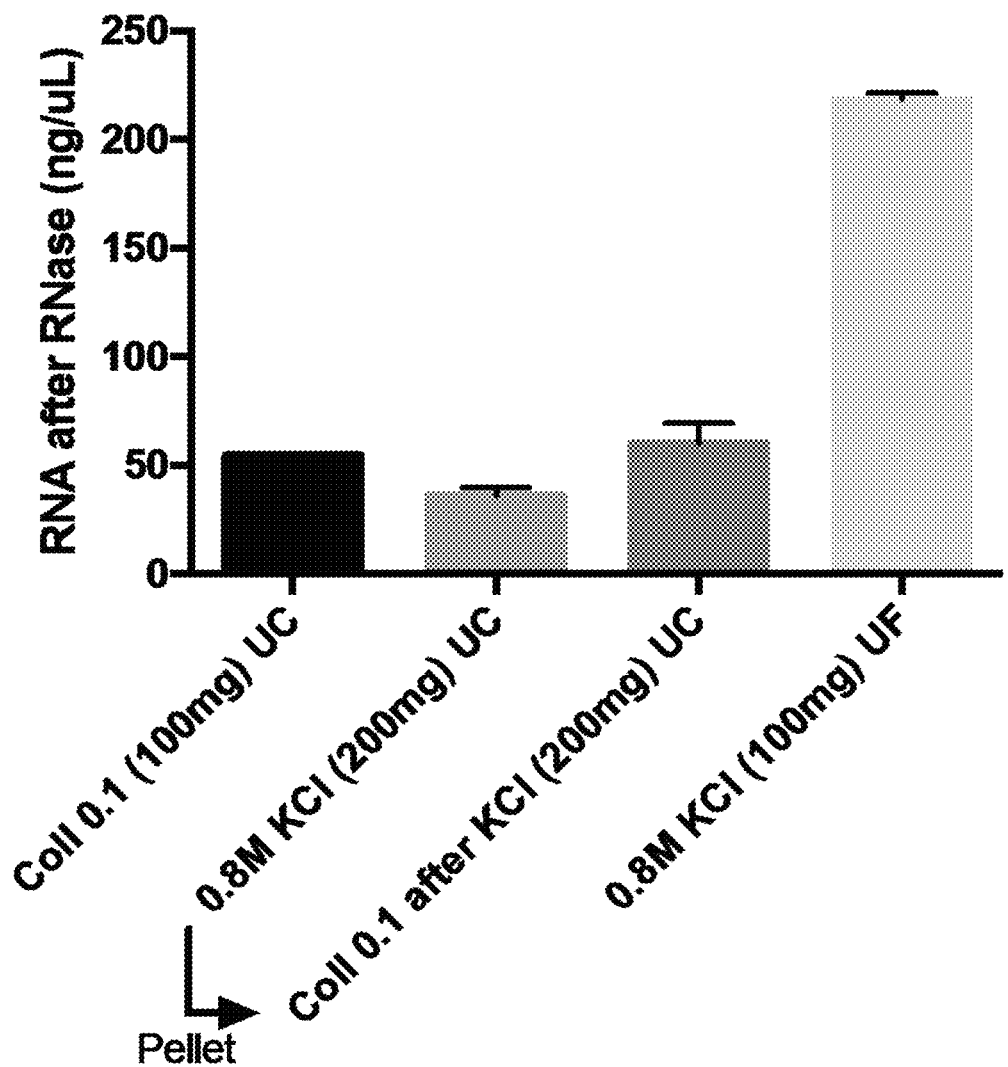
FIGS. 11A-11B. Salt and Ultrafiltration. A. Quantity of Ultracentrifugation (UC) isolated MBVs with Collagenase 0.1 was compared with MBVs isolated with KCl both with UC and Ultrafiltration (UF). The pelleted ECM after exposure to 0.8M KCl was then digested with Collagenase at 0.1 mg/mL, showing there are still MBVs left in the ECM after KCl treatment. KCl and Ultrafiltration provided the highest yield of MBVs, with 4× more than other methods. In parenthesis, starting amount of ECM material B. Size particle distribution of MBVs isolated with 0.8M KCl and Ultrafiltration measured with Nanosight shows particles from 10-300 nm in size.
Figure 11B:
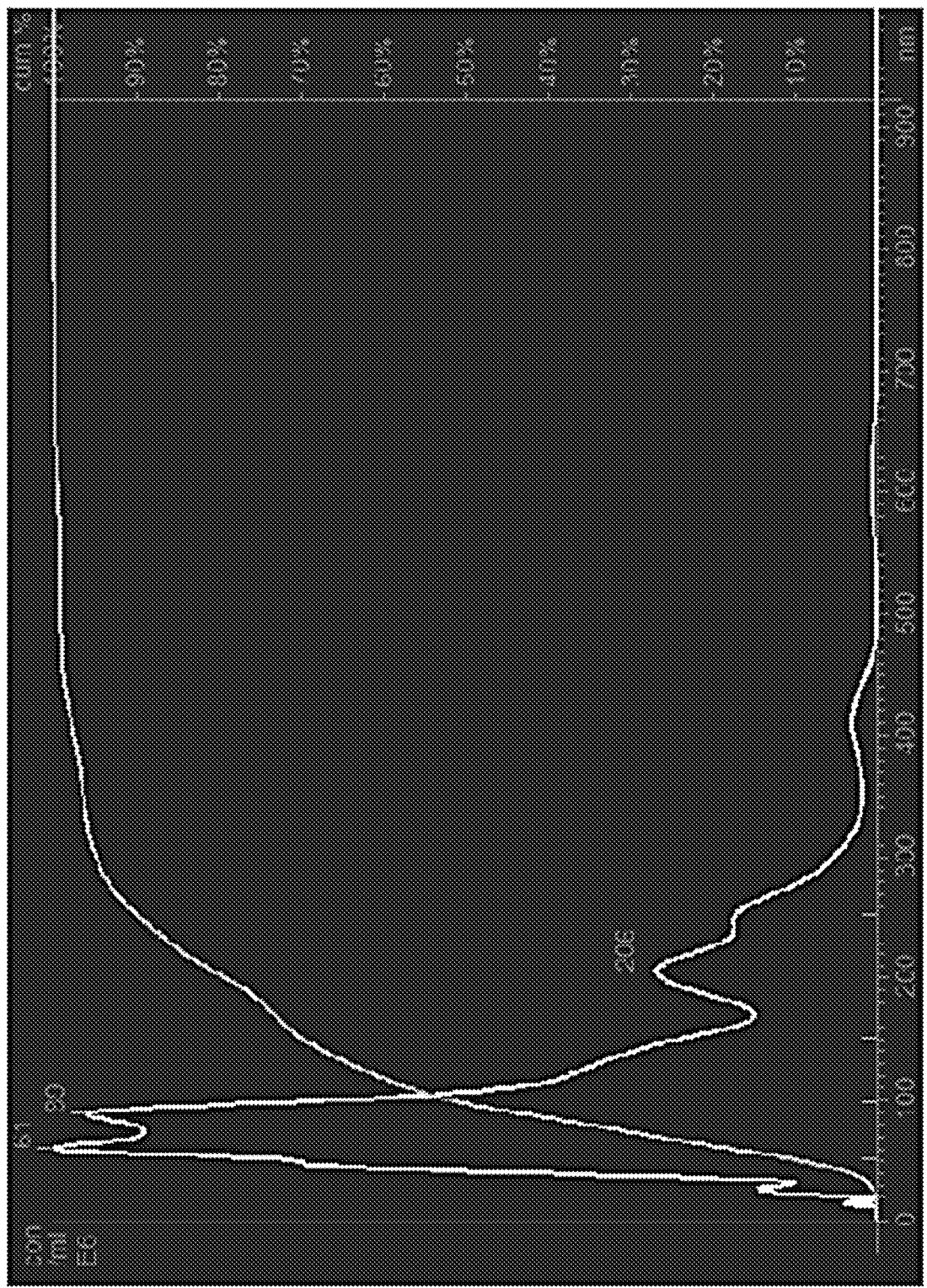
Figure 12A:
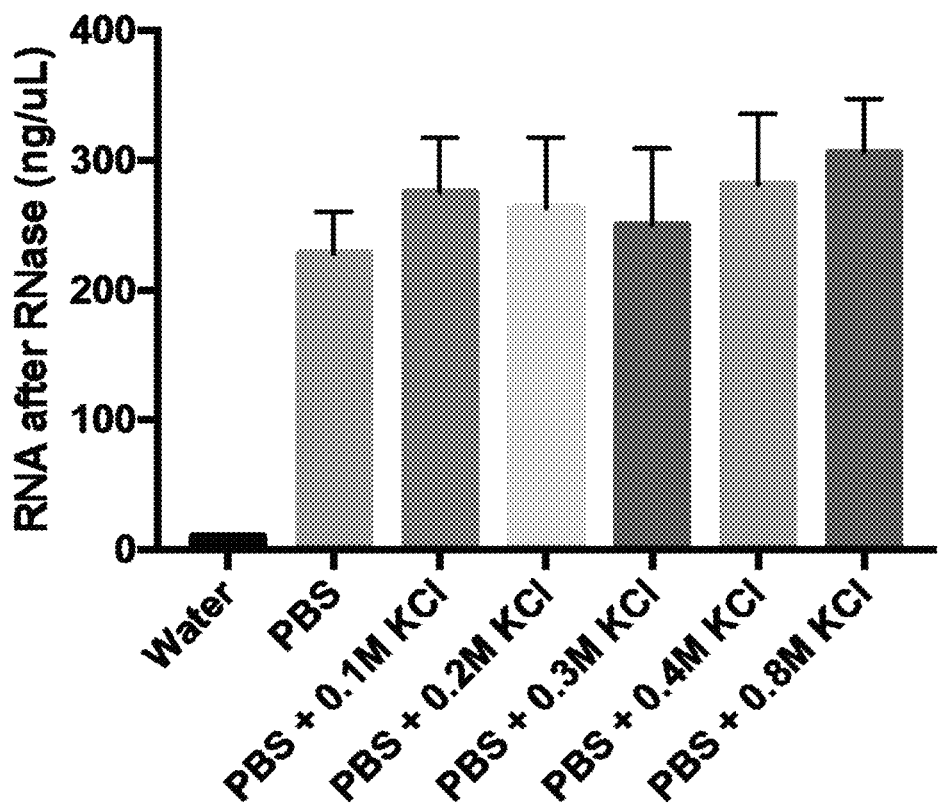
FIGS. 12A-12B. Effect of KCl. A. MBVs were isolated by resuspending the ECM in water, PBS, and PBS with increasing concentration of KCl. Ultrafiltration was used to isolate the final pellet. MBVs could be isolated with PBS and PBS with KCl, however resuspending the ECM in water PBS did not yield any MBVs. B. MBVs were isolated by resuspending ECM in PBS, $KH_2PO_4$ Buffer and $KH_2PO_4$ Buffer with 0.4M KCl. PBS isolated MBVs were suspended in both PBS and water with the same amount of MBVs showing that MBVs are viable and do not burst in water. No MBVs can be isolated with $KH_2PO_4$ buffer by itself however the addition of KCl yielded MBVs showing that it is the addition of salt that is responsible for the isolation.
Figure 12B:
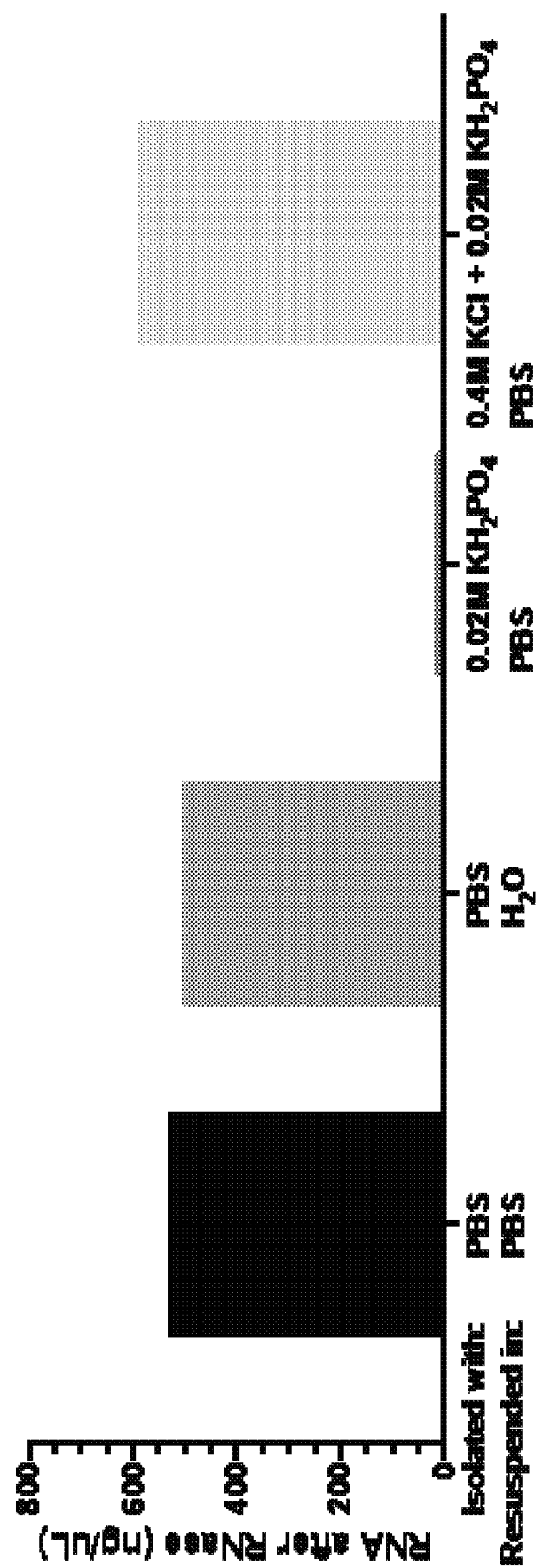
Figure 13A:
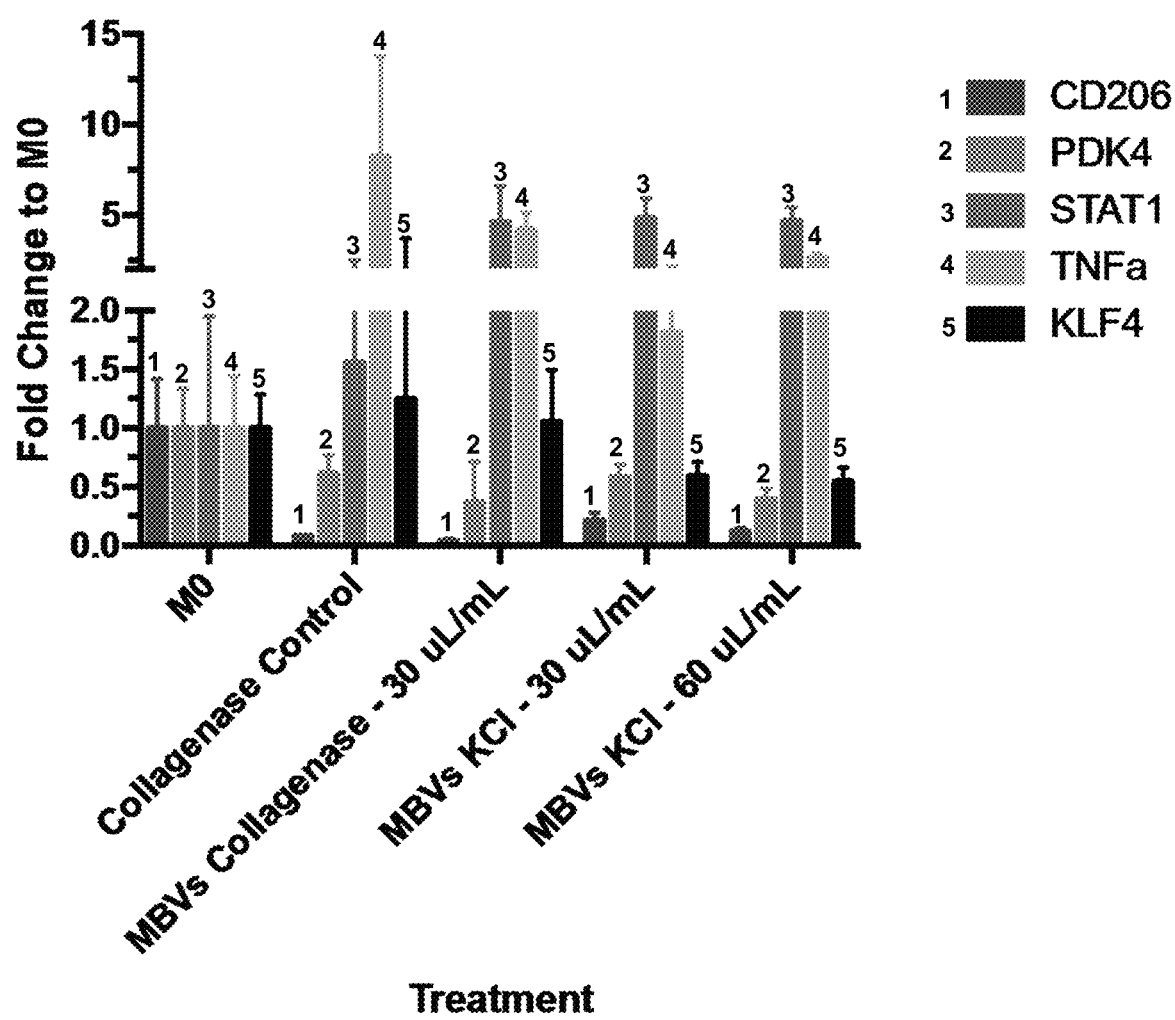
FIGS. 13A-13B. Gene expression of Bone marrow derived macrophages after 24 hour exposure to MBVs from Collagenase and KCl at 30 and 60 uL per mL. Collagenase isolated MBVs and KCl isolates MBVs showed a similar gene expression pattern A. However, collagenase isolated MBVs showed a higher ARG and INOS expression B.
Figure 13B:
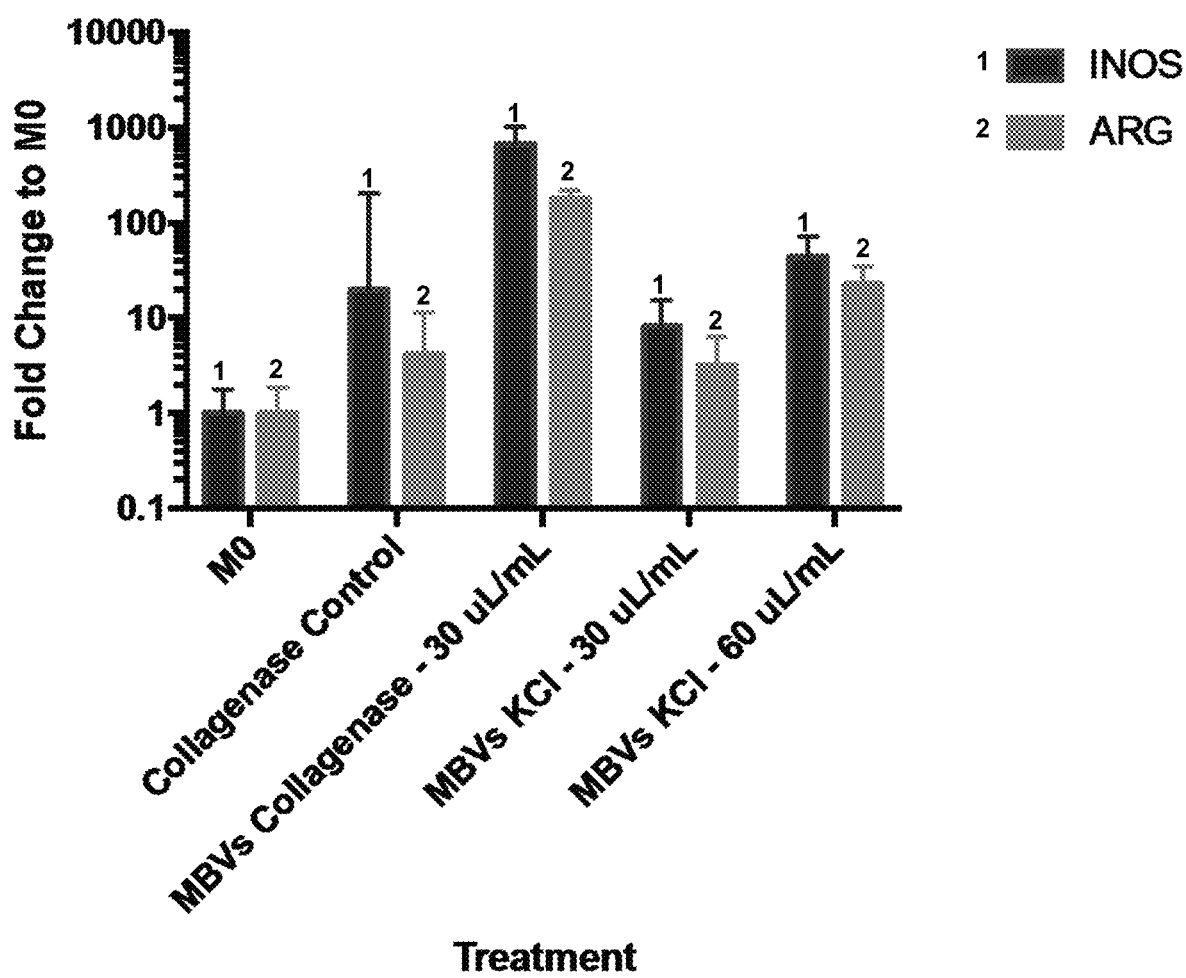

The quantity of Ultracentrifugation (UC) isolated MBVs with collagenase 0.1 mg/mL was compared with MBVs isolated with KCl both with UC and ultrafiltration (UF). To determine if KCl could dissociate all the MBVs present in the ECM, the pelleted ECM after exposure to 0.8M KCl was digested with collagenase at 0.1 mg/mL, showing there are still MBVs left in the ECM after KCl treatment. The use of KCl and ultrafiltration yielded the highest amount of MBVs of all methods compared, showing four times higher yield (FIG. 11A). These MBVs obtained with ultrafiltration were then analyzed with the use of NANOSIGHT® to validate that Ultrafiltration was preserving the vesicles (FIG. 11B).

Example 12

The Use of Ultrafiltration Allows Isolating MBVs with the Use of PBS

Phosphate buffered saline is composed of 0.01 mM $PO_4^{3-}$, 0.137 M NaCl, and 0.0027 M KCl. The combination of NaCl and KCl amount to a total concentration of salt of 0.139 M. Despite being low, given that Ultrafiltration allows for a higher yield of MBVs to be isolated, MBVs can be isolated just with the use of PBS (FIG. 4A). To demonstrate it is an effect of salt inside the PBS and not the resuspension of the ECM, a sample was resuspended in water, yielding no MB Vs.

The use of water for resuspension could also lead to asking the question whether placing the ECM in hypotonic medium, such as water, could lead to the bursting of the MBVs, this being the cause of no MBVs in the water preparation described above. To answer this question, MBVs isolated with PBS underwent a medium exchange in the ultrafiltration column so that PBS-isolated MBVs were resuspended in water. MBVs were still detectable in the mixture as shown in FIG. 4B. Furthermore, to show more definitively that the MBVs were isolated by the use of salt, the ECM was resuspended in Potassium Phosphate ($KH_2PO_4$) Buffer with and without KCl. No MBVs could be isolated with just the $KH_2PO_4$ Buffer. However, when KCl was added, MBVs were obtained (FIG. 4B).

Example 13

Salt-Isolated MBVs have Comparable Biological Activity to Enzyme-Isolated MBVs

To test whether MBVs dissociated and isolated from the ECM with the use of salt had the same biological properties as MBVs isolated with the use of enzymes, murine bone marrow derived macrophages were exposed to MBVs isolated by both methods for 24 hours. The same volume of MBVs was used for enzyme-isolated and salt-isolated (30 uL per mL of BMDM media) MBVs and a high amount of salt-isolated MBVs was also tested (60 uL/mL). After the 24-hour exposure, RNA was collected from the cells, RT-PCR was performed and quantitative PCR was used to analyze gene expression for CD206, PDK4, STAT1 TNFa KLF4, ARG1, INOS). Results show that at the exposure to the same volume and time, MBVs isolated by enzyme use of collagenase and salt have similar effects on gene expression, however the salt-isolated MBVs elicited a lower INOS and ARG1 expression than Collagenase isolated MBVs and the Collagenase Control (FIG. 5B). This could be due to the ECM fragments that are generated by enzymatic digestion that are co-isolated with enzyme based methods. Since collagenase was used as an enzyme for isolation of these MBVs, BMDMs were also treated with a sample that was obtained from using the same amount of collagenase used to isolate MBVs, run through the same isolation protocol, but without the addition of ECM (collagenase Control). As the results show, remnant collagenase enzyme can also affect's gene expression on cells.

Example 14

Effect of MBVs on Tumor Cells

FIGS. 14 and 15 provide results showing the effect of matrix-bound nanovesicles on tumor cells. Shown in the effect on two exemplary types of tumors, glioma and esophageal cancer.

Example 15

Matrix-Bound Nanovesicles Recapitulate Extracellular Matrix Effects on Macrophage Phenotype It was demonstrated that recently described ECM derived nanovesicles, also called matrix bound vesicles (MBVs), are capable of recapitulating the macrophage-activation effects of an ECM bioscaffold from which they are derived. Inhibition of specific miRNAs, miRNA125b-5p, 143-3p, and 145-5p, resulted in an opposite gene expression profile and protein expression when compared to their MBV-treated counterparts, implicating their potential role in the promotion of a regulatory macrophage phenotype. Thus MBVs and their miRNA cargo play a significant role in the macrophage response to ECM bioscaffolds and the constructive remodeling process as a whole.

Figure 16A:
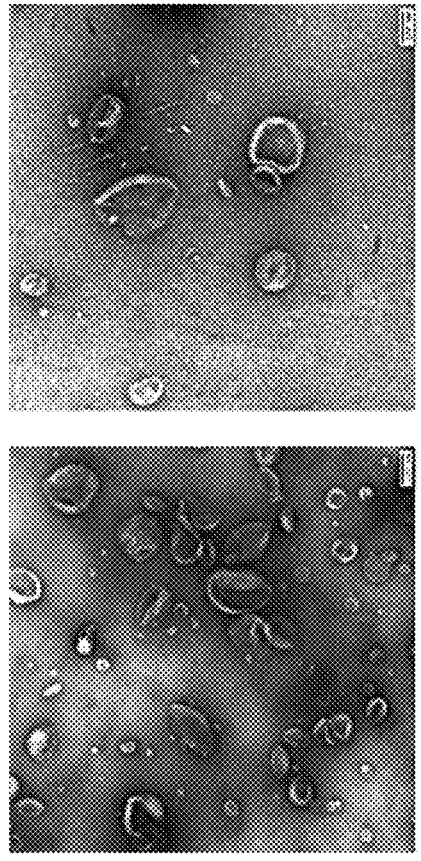
FIGS. 16A-16C. (A) 100 mg of powdered UBM-ECM and SIS-ECM were subjected to 16 hour digestion with 0.1 mg/ml collagenase solution. The resulting degradation products were then subjected to progressive centrifugation to isolate MBV. The resultant purified MBVs were then imaged at 100,000 fold magnification by transmission electron microscopy. (B) The nucleic acid content of isolated MBVs were labeled using Exo-Glow. Labeled particles were then incubated with bone marrow derived macrophages for 4 hours and imaged using fluorescence microscopy. Labeled MBVs in the absence of cells was used to establish exposure times as a control. (C) A representative heat map displaying gene expression fold changes in response to treatment. Cells were treated with 1 ml of media as well as one of the following: (1) 20 ng/ml IFNγ and 100 ng/ml LPS to promote an $M_{IFNg+LPS}$ phenotype (M1-like), (2) 20 ng/ml IL-4 to promote an $M_{IL-4}$ phenotype (M2-like), (3) 250 ug/ml of UBM-ECM, or SIS-ECM to promote an MECM phenotype, or (4) 25 ug/ml of UBM-MBVs, or SIS-MBVs to promote an $M_{MBV}$ phenotype. Pepsin (1 mg/ml) and Collagenase (0.1 mg/ml) were used as baseline controls for ECM and MBVs, respectively.
Figure 16B:
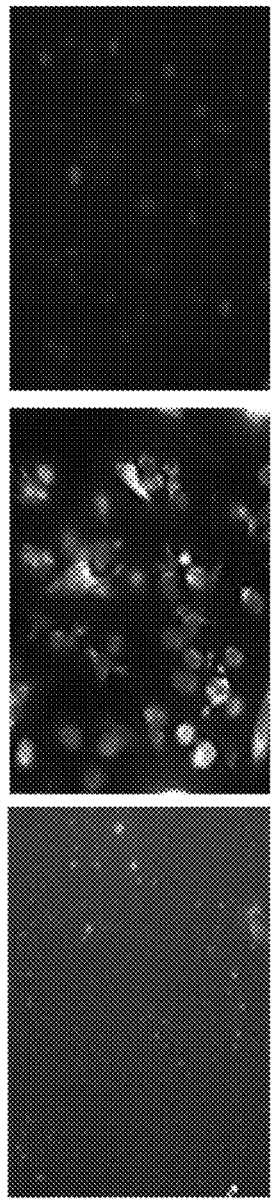
Figure 16C:
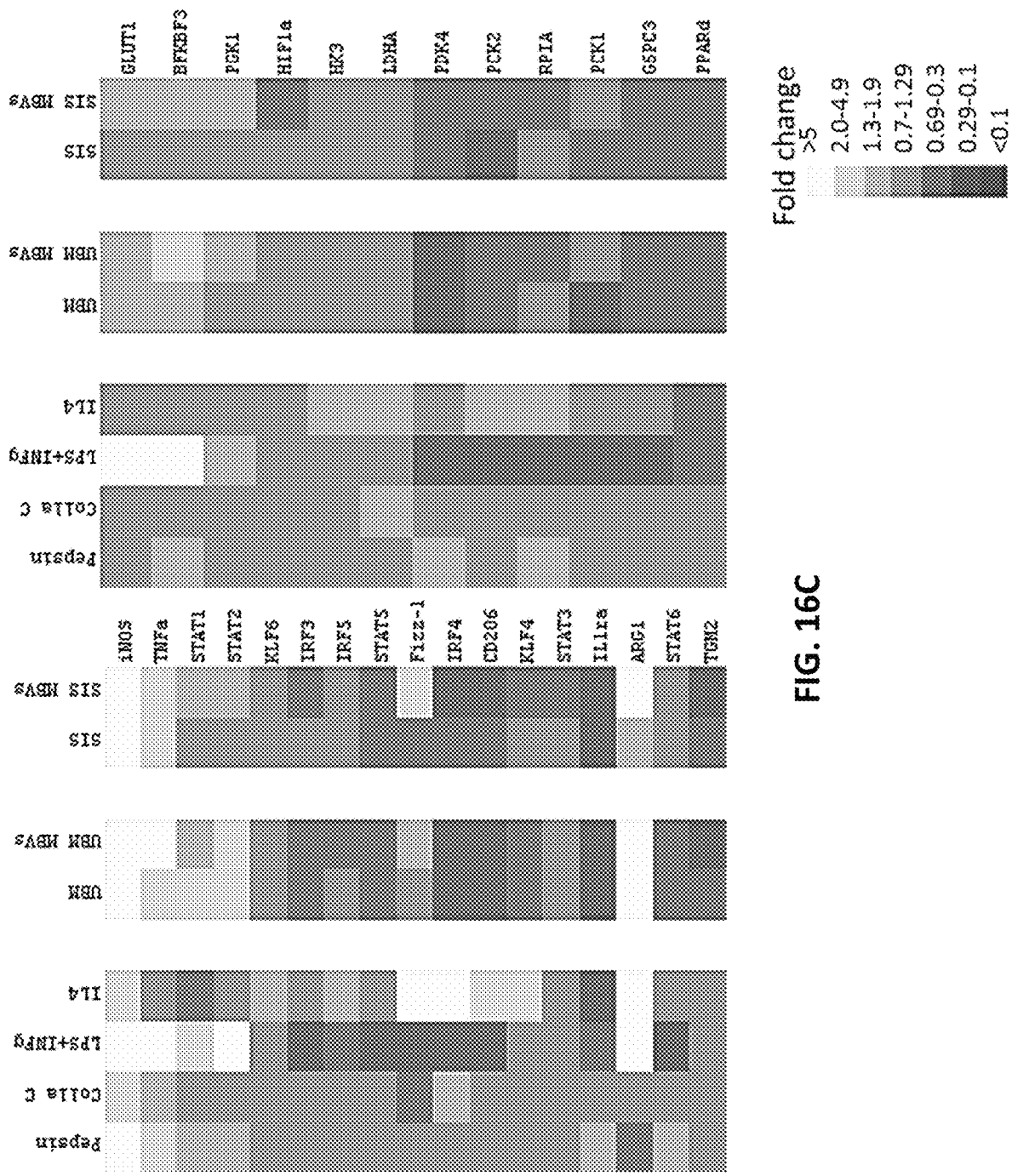

Particulate UBM-ECM or SIS-ECM was enzymatically digested for 16 hours at room temperature with 0.1% collagenase solution. The resulting ECMs were subjected to centrifugation at increasing g forces to extract MBVs. MBVs were visualized at 100,000× magnification using transmission electron microscopy (TEM) (FIG. 16A). Cellular uptake of MBVs was determined by labeling MBVs with acridine orange. Labeled MBVs were visible within BMDMs 2 hours after their addition to the culture media (FIG. 16B). The effect of MBVs on macrophage activation was evaluated by qPCR analysis of over 25 commonly used markers of macrophage activation, including surface markers, cytokines, transcription factors, and metabolic markers. The gene expression profile of macrophages treated with MBVs was almost identical to the gene expression profile of macrophages treated with ECM (FIG. 16C). Little to no effect on gene expression was observed after exposing the macrophages to pepsin or collagenase indicating that these enzymes, which are used to digest ECM prior to extraction of MBVs, are not responsible for macrophage activation. Exposure of BMDMs to IFNγ+LPS ($M_{IFN\gamma+LPS}$) or IL-4 ($M_{IL-4}$) led to distinctive changes in gene expression with contrasting profiles.

Figure 17:
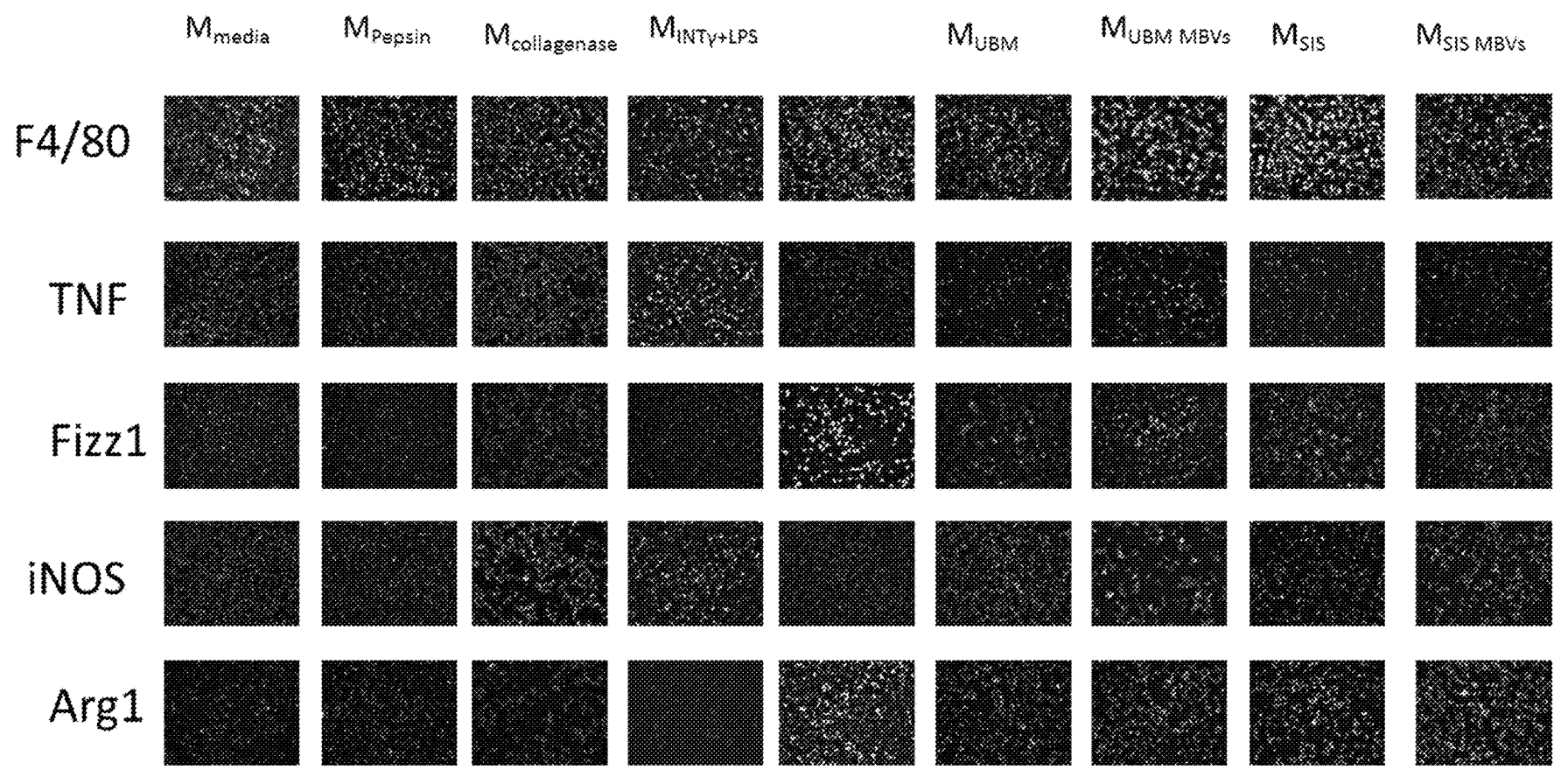

As shown in FIG. 17, immunolabeling was performed to evaluate protein expression of BMDMs. Similar to the gene expression results, MBV treated groups had an almost an identical protein expression profile as the ECM treated groups. However, in contrast to the gene expression data, both ECM groups as well as their corresponding MBV groups had protein expression profiles similar to the IL-4 treated group rather than the IFNγ+LPS treated group. Macrophage treatment with SIS-ECM and UBM-ECM and their corresponding MBVs resulted in positive expression of Fizz-1 and Arg-1 (markers that are associated with the $M_{IL-4}$ phenotype). iNOS expression was only slightly detected in the SIS-MBV group. TNF-α was detectable only in the UBM-MBV group. Both TNF-α and iNOS are markers associated with the $M_{IFN\gamma+LPS}$ phenotype. No expression of these proteins was noted in the control groups. More than 99% of cells expressed F4/80, confirming their macrophage differentiation state.

As shown in FIG. 18, secreted products of macrophages treated with MBV-SIS significantly decreased the growth of S. aureus when compared to tryptic soy broth control (p=0.033). Conditioned media of macrophages treated with each of the inhibitors of miR-125, miR-143, and miR-145, or their combination (Mix) did not decrease the growth of S. aureus. In contrast, secreted products of macrophages treated with the scramble control (Scr) significantly decreased the growth of S. aureus when compared to tryptic soy broth control (p=0.018).

Naïve and IL-4-treated macrophages produced no nitric oxide. Macrophages treated with IFN-γ/LPS produced a significant increase in nitric oxide. MBVs derived from UBM were the only treatment group to significantly increase nitric oxide production, suggesting UBM MBVs potentially have an effect on macrophage pro-inflammatory responses or anti-microbial activity. No miR treatment resulted in an increase in nitric oxide activity.

A basal level of phagocytosis as measured by uptake of FITC-E. Coli particles was shown by all macrophages. Treatment with IFN-γ/LPS resulted in a significant increase in phagocytic activity. ECM and ECM-derived MBV treatment resulted in significant increases in phagocytic uptake. The data indicated MBVs could be more potent in inducing phagocytosis or become more active when released from ECM scaffolds. There was no significant difference in phagocytosis between macrophages treated with UBM or SIS. However, MBVs from UBM caused a significant increase in macrophage phagocytosis compared to macrophages treated with SIS-MBVs.

Figure 19A:
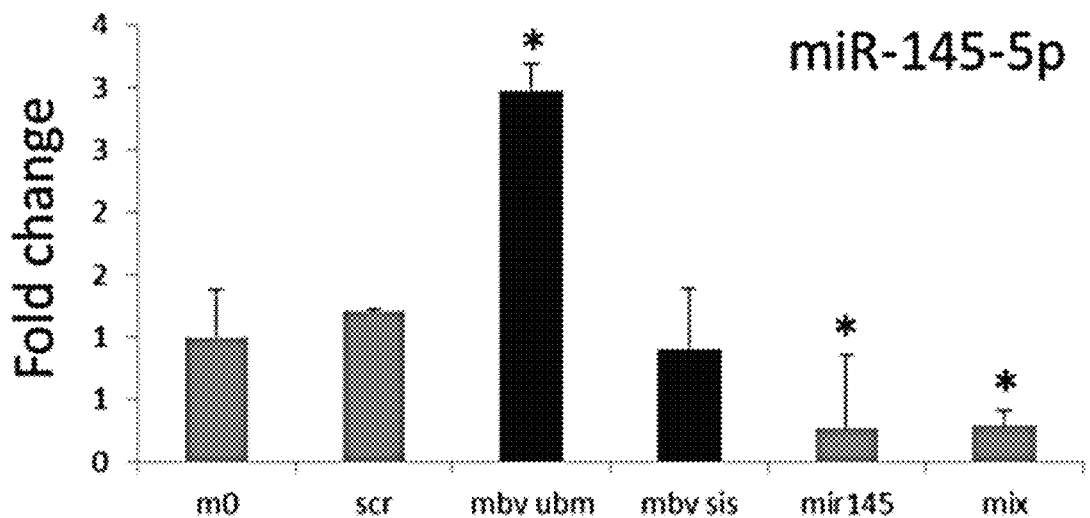
FIG. 19A-19E. Macrophage miRNA inhibition (A-C) Selective inhibition of specific miRNAs, miR-145-5p, miR-145-3p, and miR-125-b-5p using 50 nM of inhibitor for each. Relative abundance of miRNA levels following inhibition was determined by TaqMan miRNA qPCR assays. (D) Gene expression analysis of cells exposed to MBVs, or transfected with scrambled control miRNA inhibitor, mmu-miR-145-5p inhibitor, mmu-miR-143-3p inhibitor, mmu-miR-125b-5p inhibitor, or a combination of all three inhibitors was evaluated using qPCR. Results are presented in a heatmap form using Tree-view software; all fold changes are with respect to media control. Scale bar scoring system is demonstrated as follows: less than 0.1 fold change (−3), 0.1-0.29 fold change (−2), 0.3-0.69 (−1), 0.7-1.29 (0), 1.3-1.9 (+1), 2.0-4.9 (+2), greater than 5.0 (+3). (E) BMDM were exposed for 4 h to 50 nM of one of the following: scrambled control, mmu-miR-125b-5p inhibitor, mmu-miR-143-3p inhibitor, mmu-miR-145-5p, or a combination of all three (mix). Treatment media was then changed to normal growth media for additional 18 hours. Cells were then fixed with 4% PFA. The cells were then incubated with anti-murine antibody for markers of the M1-like phenotype TNFα and iNOS, or markers of the M2-like phenotype Fizz1 and Arginase1. Exposure times were established based upon a negative isotype control and cytokine-treated controls and kept constant for each marker tested. Cell nuclei was stained with DAPI. Images were taken at 200× magnification. The results show that miRNA inhibition is capable of impacting the expression of several probed proteins, implicating the role of miR-125b-5p, miR-143-3p, and miR-145-5p in the formation of the $M_{MBV}$ phenotype.
Figure 19B:
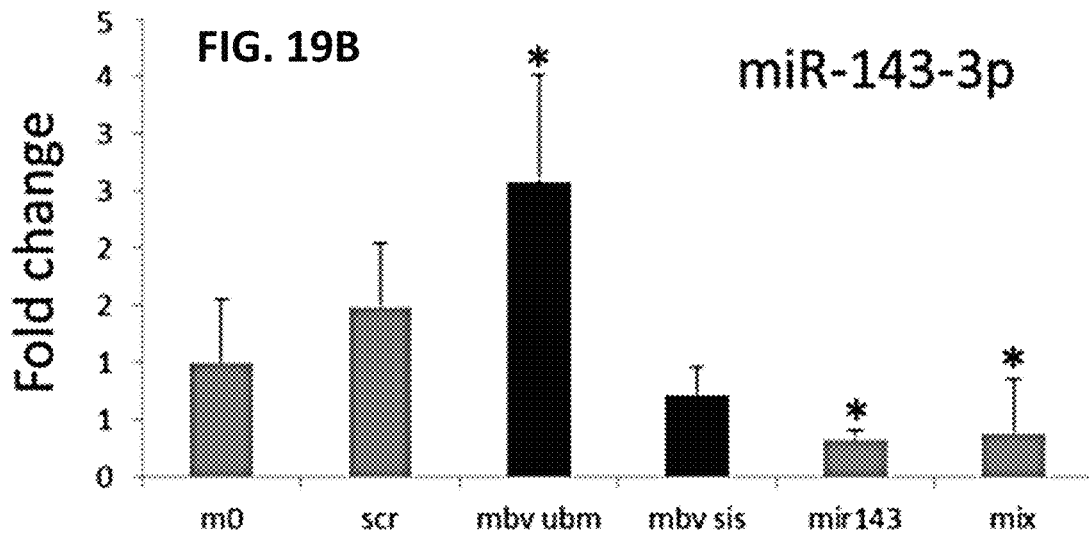
Figure 19C:
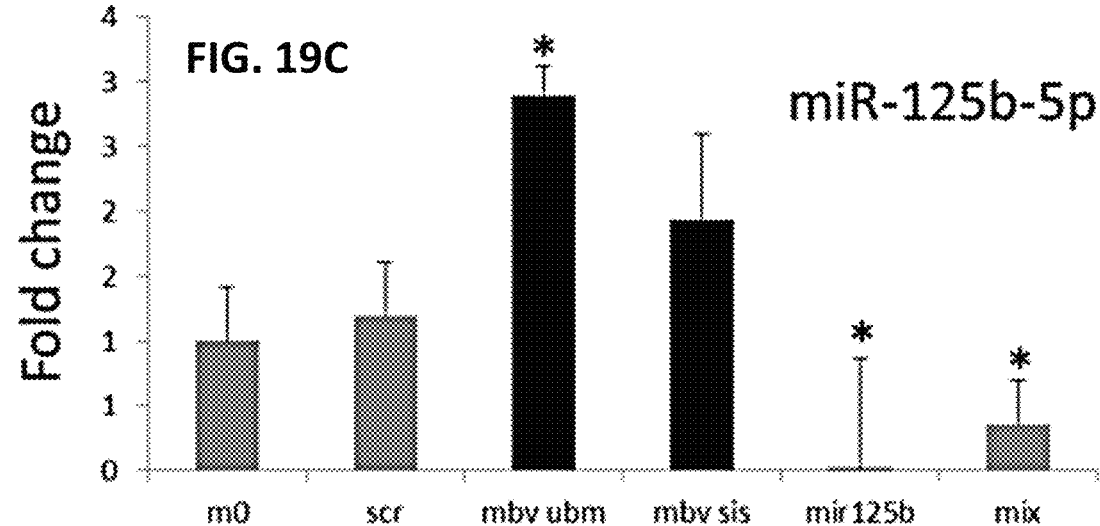
Figure 19D:
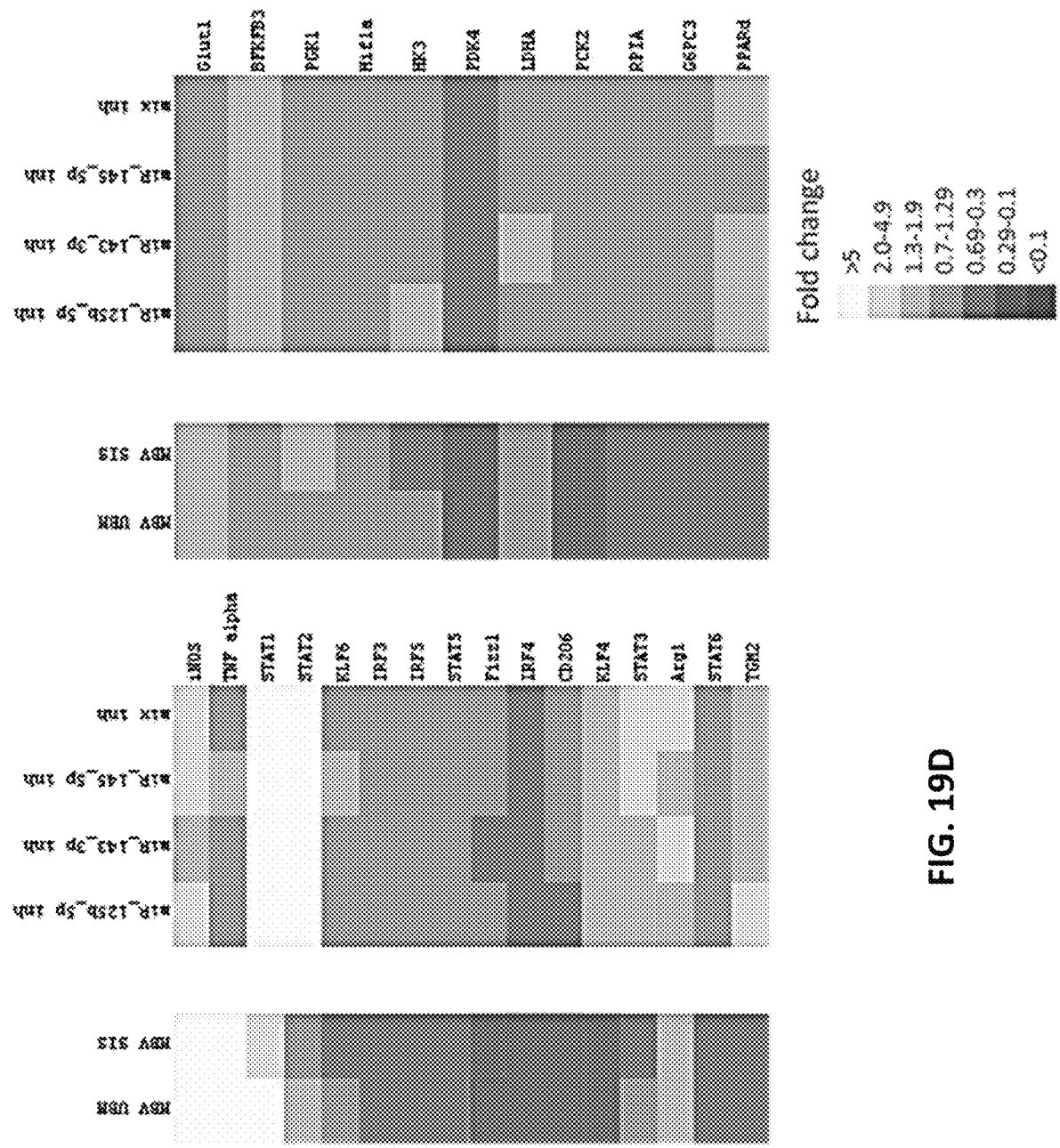
Figure 19E:
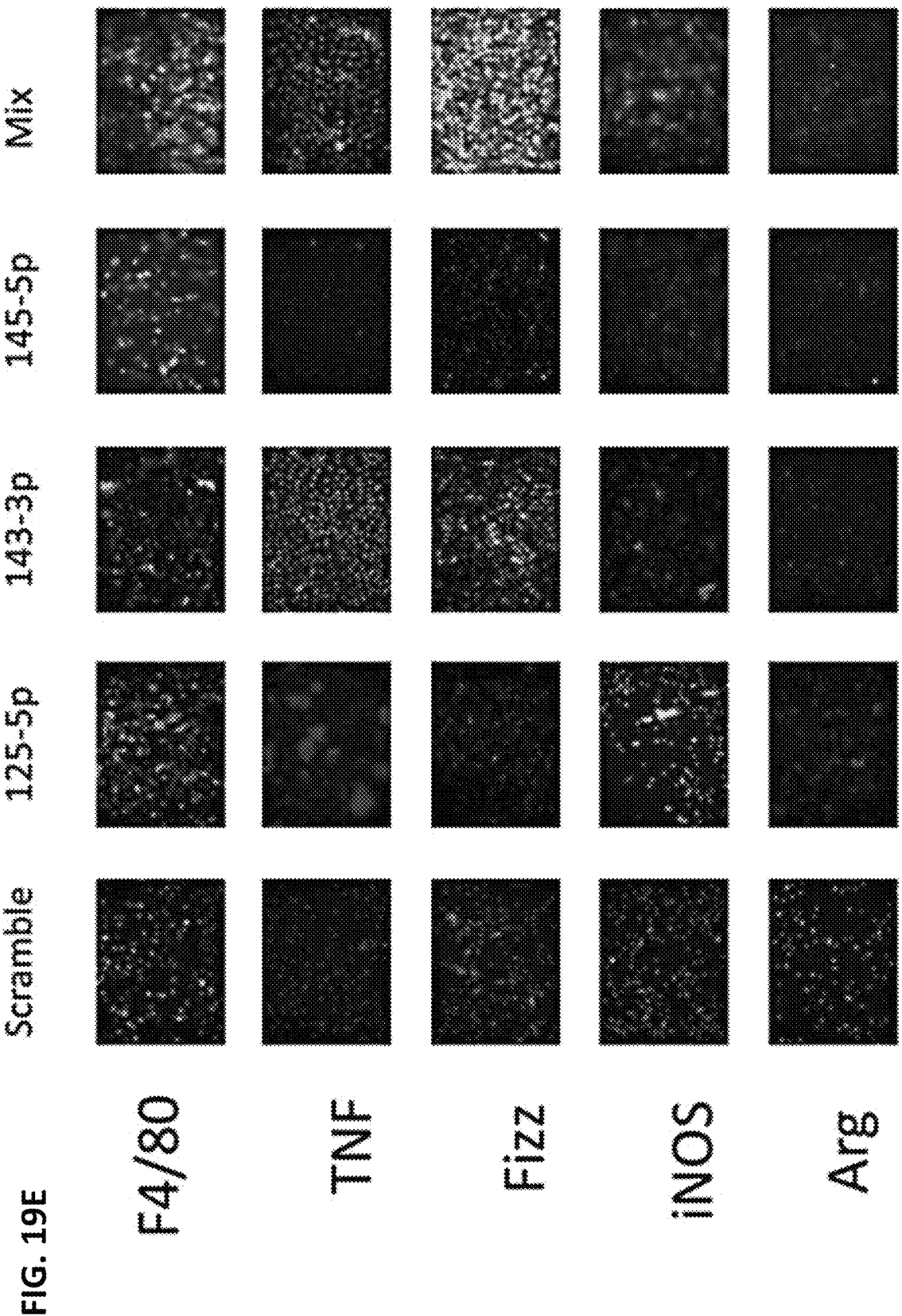

UBM-MBVs and SIS-MBVs were treated with RNase for 30 minutes to degrade any remnant RNA that could have accumulated during the ECM decellularization process or the MBV isolation process. The RNase reaction was then stopped and RNA was isolated from the MBVs. Small cDNA libraries were constructed from the RNA extracted from MBVs. The libraries were read with the Ion Proton platform. Sequencing data were trimmed on the basis of size and Phred score before alignment with the human genome. More than 34% of the small RNA reads were mapped to known sequences within the human genome. Reads were annotated to miRBase (release 21). The miRNA sequences that were most frequently identified in UBM-MBVs and SIS-MBVs are shown in the table below:

|  | UBM_MBVs | SIS_MBVs |
| --- | --- | --- |
| mir-145 | 3266.20782 | 36.2228968 |
| mir-143 | 906.527531 | 11.8118142 |
| mir-23b | 89.920071 | 0.78745428 |
| mir-27b | 75.2664298 | 1.57490856 |
| mir-23a | 74.8223801 | 0 |
| let-7b | 72.8241563 | 9.0557242 |
| mir-125a | 72.1580817 | 1.57490856 | miRNA highlighted were selected for downstream analysis because they are involved in macrophage activation. (Chaudhuri et al., J Immunol, 2011. 187(10): p. 5062-8; Banerjee et al., J Biol Chem, 2013. 288(49): p. 35428-36;

Zang et al., Int J Mol Med, 2013. 31(4): p. 797-802). To investigate the mechanism by which MBVs activate macrophages, miR-145-5p, miR-143-3p and miR-125b-5p were inhibited in BMDMs. Successful inhibition of miRNAs was shown by qPCR (FIG. 19A). miR-145 expression levels were reduced by more than 70%, miR-143 expression levels were reduced by 65% and miR-125b expression levels were reduced by more than 95%.

Macrophages have been shown to be critical regulators of normal healing following injury, and in normal tissue development. It is disclosed herein that MBVs can largely recapitulate the effects of whole ECM upon macrophage phenotype. Thus, MBVs, like ECM, can be used for modifying macrophage phenotype, such as for inducing regulatory macrophages.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

2. The method of claim 1, wherein the subject has an ulcer, a burn or a blister due to abrasion or chemical injury, and wherein the method accelerates healing of the ulcer, burn or blister.

3. The method of claim 1, wherein the nanovesicles are isolated from extracellular matrix by:
   (a) digesting the extracellular matrix with an enzyme to produce digested extracellular matrix;
   (b) centrifuging the digested extracellular matrix to remove collagen fibril remnants, thereby producing a fibril-free supernatant;
   (c) centrifuging the fibril-free supernatant to isolate solid materials; and
   (d) suspending the solid materials in a carrier,
thereby isolating the nanovesicles from the extracellular matrix.

4. The method of claim 1, wherein the method increases a remodeling response of the macrophages in the subject.

5. The method of claim 1, wherein the method reduces pro-inflammatory macrophages in the subject.

6. The method of claim 1, wherein the method increases the proliferation and/or differentiation of the macrophages.

We claim:

1. A method of increasing M2 macrophages in a subject, comprising administering to a subject a therapeutically effective amount of a composition comprising isolated nanovesicles derived from an extracellular matrix, and a pharmaceutically acceptable carrier, wherein the nanovesicles do not express CD63 or CD81, or are $CD63^{lo}CD81^{lo}$, and wherein the nanovesicles are derived from urinary bladder matrix (UBM) extracellular matrix or small intestinal submucosa (SIS) extracellular matrix, thereby increasing M2 macrophages in the subject.

7. The method of claim 1, wherein the subject has a wound involving damage to dermis or epidermis, an eye wound, a dental tissue wound, or an oral cavity wound.

8. The method of claim 1, wherein the subject is an organ transplant recipient, a subject with graft versus host disease, or a subject with myocardial infarction.

9. The method of claim 1, wherein the subject has a surgical or non-surgical wound and the method promotes wound healing.

10. The method of claim 9, wherein the subject has impaired wound healing.

11. The method of claim 9, wherein the nanovesicles are administered locally to the site of the wound.

12. The method of claim 1, wherein the nanovesicles are $CD63^{lo}CD81^{lo}$ as measured by flow cytometry or Western blot.

13. A method of increasing M2 macrophages in a subject, comprising administering to a subject a therapeutically effective amount of a composition comprising isolated nanovesicles derived from an extracellular matrix, and a pharmaceutically acceptable carrier, wherein the nanovesicles do not express CD63 or CD81, or are $CD63^{lo}CD81^{lo}$, and wherein the nanovesicles comprise miR-145 and/or miR-181, thereby increasing M2 macrophages in the subject.

14. The method of claim 13, wherein the subject has an ulcer, a burn or a blister due to abrasion or chemical injury, and wherein the method accelerates healing of the ulcer, burn or blister.

15. The method of claim 13, wherein the nanovesicles are isolated from extracellular matrix by:
   (a) digesting the extracellular matrix with an enzyme to produce digested extracellular matrix;
   (b) centrifuging the digested extracellular matrix to remove collagen fibril remnants, thereby producing a fibril-free supernatant;
   (c) centrifuging the fibril-free supernatant to isolate solid materials; and
   (d) suspending the solid materials in a carrier,
thereby isolating the nanovesicles from the extracellular matrix.

16. The method of claim 13, wherein the method increases a remodeling response of the macrophages in the subject.

17. The method of claim 13, wherein the method reduces pro-inflammatory macrophages in the subject.

18. The method of claim 13, wherein the method increases the proliferation and/or differentiation of the macrophages.

19. The method of claim 13, wherein the subject has a wound involving damage to dermis or epidermis, an eye wound, a dental tissue wound, or an oral cavity wound.

20. The method of claim 13, wherein the subject is an organ transplant recipient, a subject with graft versus host disease, or a subject with myocardial infarction.

21. The method of claim 13, wherein the subject has a surgical or non-surgical wound and the method promotes wound healing.

22. The method of claim 21, wherein the subject has impaired wound healing.

23. The method of claim 21, wherein the nanovesicles are administered locally to the site of the wound.

24. The method of claim 13, wherein the nanovesicles are derived from urinary bladder matrix (UBM) extracellular matrix or small intestinal submucosa (SIS) extracellular matrix.

25. The method of claim 13, wherein the nanovesicles are CD631CD811° as measured by flow cytometry or Western blot.

26. The method of claim 13, wherein the nanovesicles are derived from dermis extracellular matrix.

27. The method of claim 13, wherein the nanovesicles are derived from intestine, liver, heart, esophagus, spleen, stomach, umbilical cord, pericardium, cardiac tissue, or skeletal muscle extracellular matrix.

* * * * *

UNITED STATES PATENT AND TRADEMARK OFFICE
CERTIFICATE OF CORRECTION

PATENT NO. : 12,161,778 B2
APPLICATION NO. : 17/072651
DATED : December 10, 2024
INVENTOR(S) : Badylak et al.

Page 1 of 1

It is certified that error appears in the above-identified patent and that said Letters Patent is hereby corrected as shown below:

On the Title Page

Item (57) ABSTRACT, Line 3:
"Methods are producing the ECM-derived nanovesicles are also disclosed" should read --Methods of producing the ECM-derived nanovesicles are also disclosed--.

Signed and Sealed this
Seventeenth Day of June, 2025

Coke Morgan Stewart
*Acting Director of the United States Patent and Trademark Office*

SEQUENCE LISTING

<160> NUMBER OF SEQ ID NOS: 3

<210> SEQ ID NO 1
<211> LENGTH: 88
<212> TYPE: RNA
<213> ORGANISM: Homo sapiens

<400> SEQUENCE: 1
caccuugucc ucacggucca guuuucccag gaaucccuua gaugcuaaga uggggauucc      60
uggaaauacu guucuugagg ucaugguu                                        88

<210> SEQ ID NO 2
<211> LENGTH: 110
<212> TYPE: RNA
<213> ORGANISM: Homo sapiens

<400> SEQUENCE: 2
agaagggcua ucaggccagc cuucagagga cuccaaggaa cauucaacgc ugucggugag      60
uuugggauuu gaaaaaacca cugaccguug acuguaccuu gggguccuua               110

<210> SEQ ID NO 3
<211> LENGTH: 24
<212> TYPE: RNA
<213> ORGANISM: Homo sapiens

<400> SEQUENCE: 3
guccaguuuu cccaggaauc ccuu                                            24